(12) United States Patent
Oreper

(10) Patent No.: US 8,270,565 B2
(45) Date of Patent: Sep. 18, 2012

(54) DUAL ENERGY IMAGING SYSTEM

(75) Inventor: Boris Oreper, Newton, MA (US)

(73) Assignee: L-3 Communications Security and Detection Systems Inc., Woburn, MA (US)

( * ) Notice: Subject to any disclaimer, the term of this patent is extended or adjusted under 35 U.S.C. 154(b) by 351 days.

(21) Appl. No.: 12/776,042

(22) Filed: May 7, 2010

(65) Prior Publication Data

US 2010/0284509 A1 Nov. 11, 2010

Related U.S. Application Data

(60) Provisional application No. 61/176,783, filed on May 8, 2009.

(51) Int. Cl.
*G01N 23/04* (2006.01)
(52) U.S. Cl. .......................................... 378/57; 378/19
(58) Field of Classification Search ................. 378/9, 10, 378/19, 57
See application file for complete search history.

(56) References Cited

U.S. PATENT DOCUMENTS

| | | | |
|---|---|---|---|
| 4,131,798 A | 12/1978 | Reddy et al. | |
| 4,245,158 A | 1/1981 | Burstein et al. | |
| 4,366,382 A | 12/1982 | Kotowski | |
| 4,823,371 A | 4/1989 | Grady | |
| 4,958,080 A | 9/1990 | Melcher | |
| 5,040,199 A | 8/1991 | Stein | |
| 5,044,002 A | 8/1991 | Stein | |
| 5,490,193 A | 2/1996 | Kuroda et al. | |
| 5,642,393 A | 6/1997 | Krug et al. | |
| 5,665,969 A | 9/1997 | Beusch | |
| 5,974,111 A | 10/1999 | Krug et al. | |
| 6,081,580 A | 6/2000 | Grodzins et al. | |
| 6,118,125 A | 9/2000 | Carlson et al. | |
| 6,248,990 B1 | 6/2001 | Pyyhtiä et al. | |
| 6,421,420 B1 | 7/2002 | Grodzins et al. | |
| 6,628,745 B1 | 9/2003 | Annis et al. | |

(Continued)

FOREIGN PATENT DOCUMENTS

EP 0 455 177 A2 11/1991

(Continued)

OTHER PUBLICATIONS

International Search Report and Written Opinion for International Application No. PCT/US2007/020542 dated Jul. 17, 2008.

(Continued)

*Primary Examiner* — Courtney Thomas
(74) *Attorney, Agent, or Firm* — Wolf, Greenfield & Sacks, P.C.

(57) ABSTRACT

A dual energy inspection system that generates X-rays with an electron beam scanned over targets. A switchable voltage source that can be change its voltage output may cause X-rays to be generated at different energies. This X-ray generation subsystem is controlled by a sequencer that provides beam steering and shaping control inputs that may be dependent on the voltage provided by the voltage source. In another aspect, the dual energy inspection system may use multiple types of detectors, each sensitive to X-rays of a different energy. A relatively small number of detectors sensitive to one energy level is provided. Nonetheless, dual energy measurements may be made on objects within an item under inspection by identifying points that, for each object of interest, provide a low interference path to one of those detectors. Measurements made with radiation emanating from those points are used for dual energy analysis of those objects.

29 Claims, 46 Drawing Sheets

U.S. PATENT DOCUMENTS

| | | | |
|---|---|---|---|
| 7,016,459 | B2 | 3/2006 | Ellenbogan et al. |
| 7,233,644 | B1 | 6/2007 | Bendahan et al. |
| 7,672,427 | B2 | 3/2010 | Chen et al. |
| 2002/0094059 | A1 | 7/2002 | Grodzins |
| 2006/0233302 | A1 | 10/2006 | Might et al. |
| 2008/0043917 | A1 | 2/2008 | Oreper |
| 2008/0170655 | A1 | 7/2008 | Bandahan |

FOREIGN PATENT DOCUMENTS

| | | |
|---|---|---|
| WO | WO 92/03837 A1 | 3/1992 |
| WO | WO 2004/095060 A3 | 11/2004 |

OTHER PUBLICATIONS

International Search Report for International Application No. PCT/US04/012110 dated Feb. 8, 2005.

International Search Report for International Application No. PCT/US2006/044195 dated Mar. 18, 2008, 5 pages.

Baron "A Refractive Collimator for Synchrotron Radiation" Spring-8 Instrumentation & Techniques; 1999; pp. 51-52.

Caria, Mario, Ed., "Radiation Imaging Detectors," Proceedings of the 3rd International Workshop on Radiation Imaging Detectors, Orosei, Sardinia, Italy, Sep. 23-27, 2001, Table of Contents.

Fischer, P., et al., "Single Photon Counting X-ray Imaging with Si and CdTe Single Chip Pixel Detectors and Multichip Pixel Modules," 3rd Int'l Workshop on Radiation Imaging Detectors, Orosei, Sardinia, Sep. 24-27, 2001.

Forth "Design and Fabrication of Compound Refractive X-ray Lenses for CHESS" Dept. of Physics, Oberlin College, Ohio; 2000; pp. 1-9.

Graeme, Jerald G., "Photodiode Amplifiers: Op Amp Solutions," McGraw-Hill, 1995, pp. v-31.

Kuyumchyan et al. "Study of optical properties of x-ray system based on two zone plates" IMT RAS Chernogolovka, Moskow District, Russia; Jul. 2005; 5 pages.

Melcher, C.L., et al., "A promising new scintillator: cerium-doped lutetium oxyorthosilicate," Nuclear Instruments and Methods in Physics Research, A314 (1992) pp. 212-214.

Pereira et al. "Large Aperture X-ray refractive Lens from Lithium" Dept. of Physics, University of Michigan; Nov. 2004; pp. 174-184; vol. 5539.

Pereira et al. "Lithium X-ray Refractive Lenses" Dept. of Physics, University of Michigan, Dec. 2002; 2 pages.

Pereira et al. "Parabolic lithium refractive optics for x-rays" Review of Scientific Instruments, Jan. 2004, pp. 37-41; vol. 75.

Schirato, R.C., et al., "Development of monolithic $Cd_{1-x}Zn_xTe$ arrays with improved energy and spatial resolution," *SPIE*, vol. 2278 X-Ray and UV Detectors (1994), pp. 47-56.

Turchetta, R., et al., "High Spatial Resolution Silicon Read-Out System for Single Photon X-Ray Detection," *IEEE Trans. Nuclear Science* 41(4):1063-1068 (1994).

Van Eijk, C.W.E., "New inorganic scintillators—aspects of energy resolution," Nuclear Instruments and Methods in Physics Research, A471 (2001) pp. 244-248.

International Search Report and Written Opinion for International Application No. PCT/US2010/001353 dated Dec. 17, 2010.

"Nuclear Instruments and Methods in Physics Research Section A: Accelerators, Spectrometers, Detectors Table of Contents of and Associated Equipment," vol. 491, Issues 1-2, pp. 1-350 (Sep. 21, 2002), from Science Direct website http://www.sciencedirect.com/science, pp. 1-5, printed out Mar. 5, 2004.

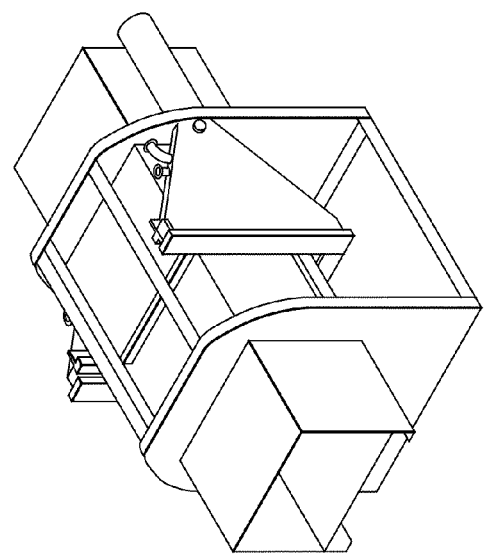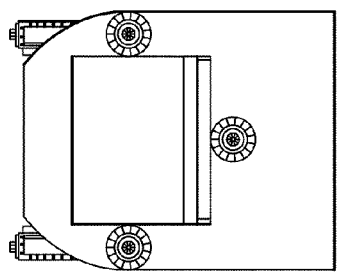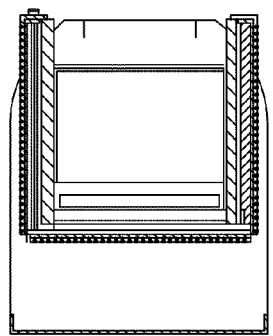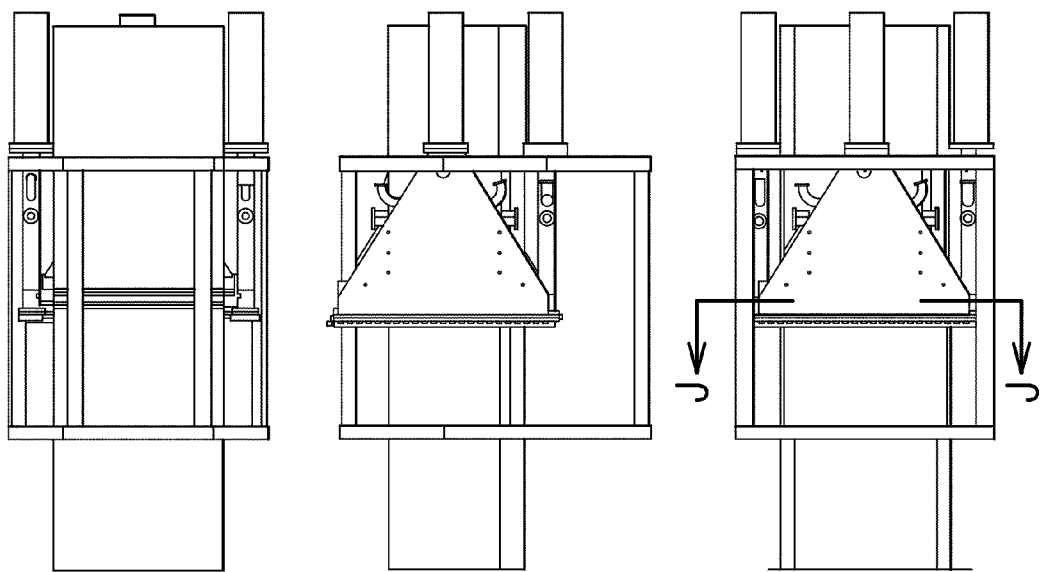
FIG. 15

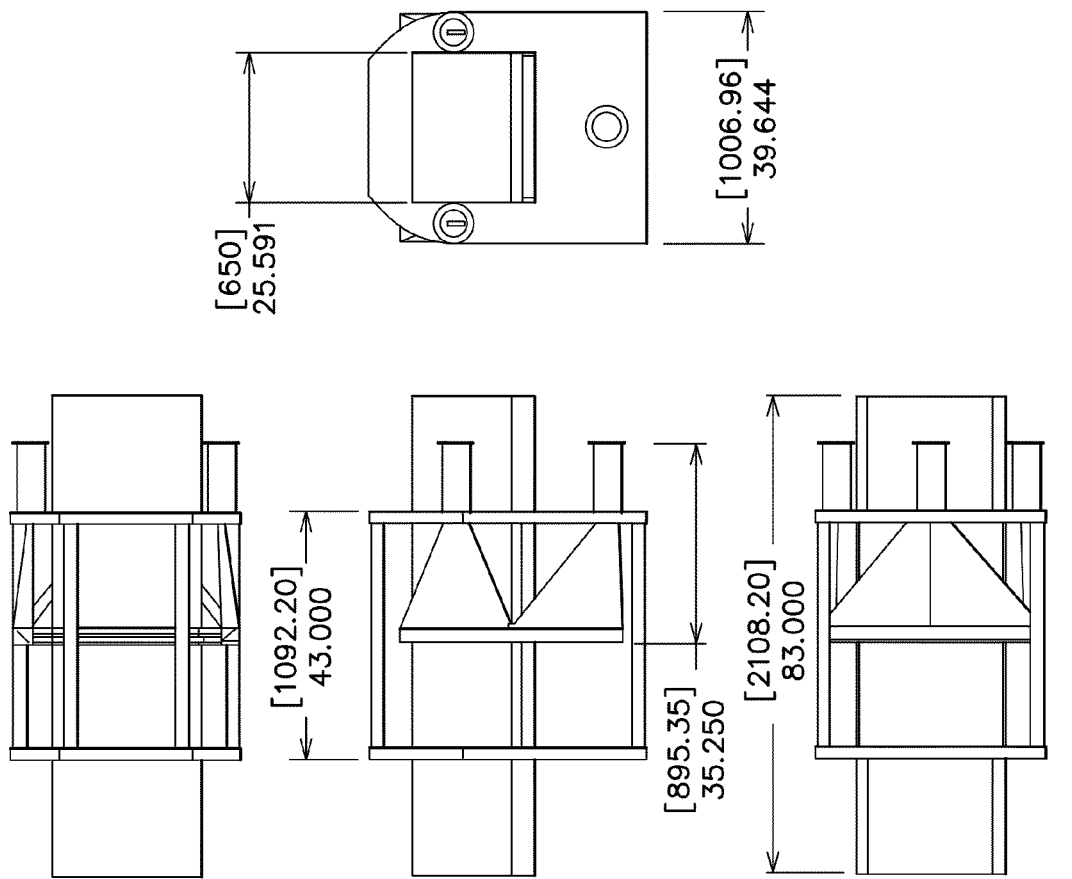
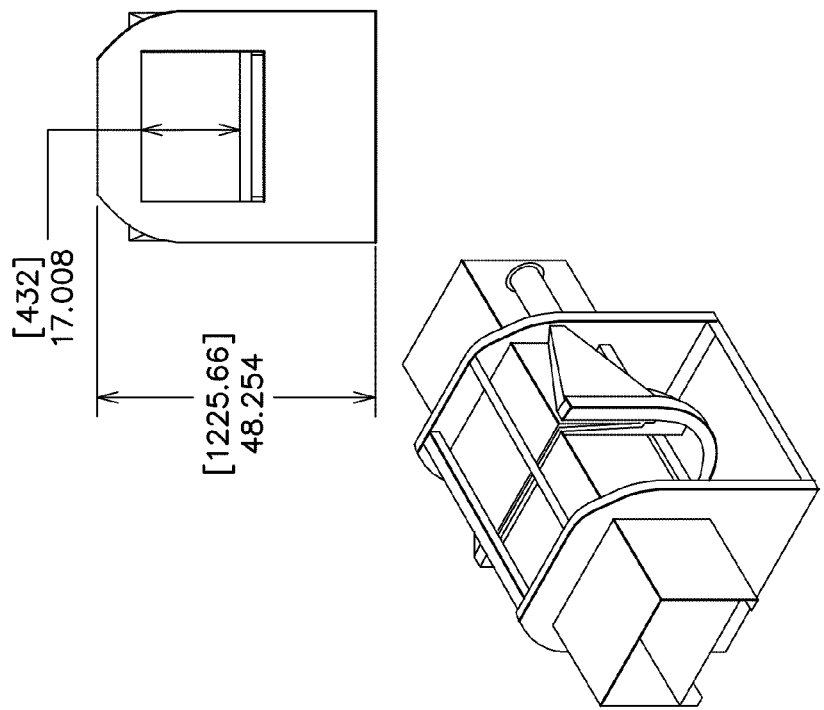
FIG. 16

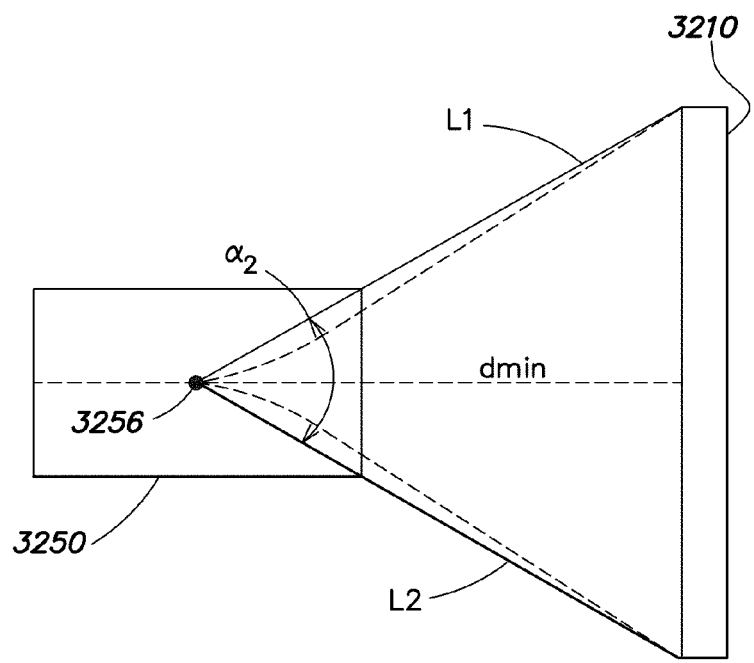
FIG. 32A
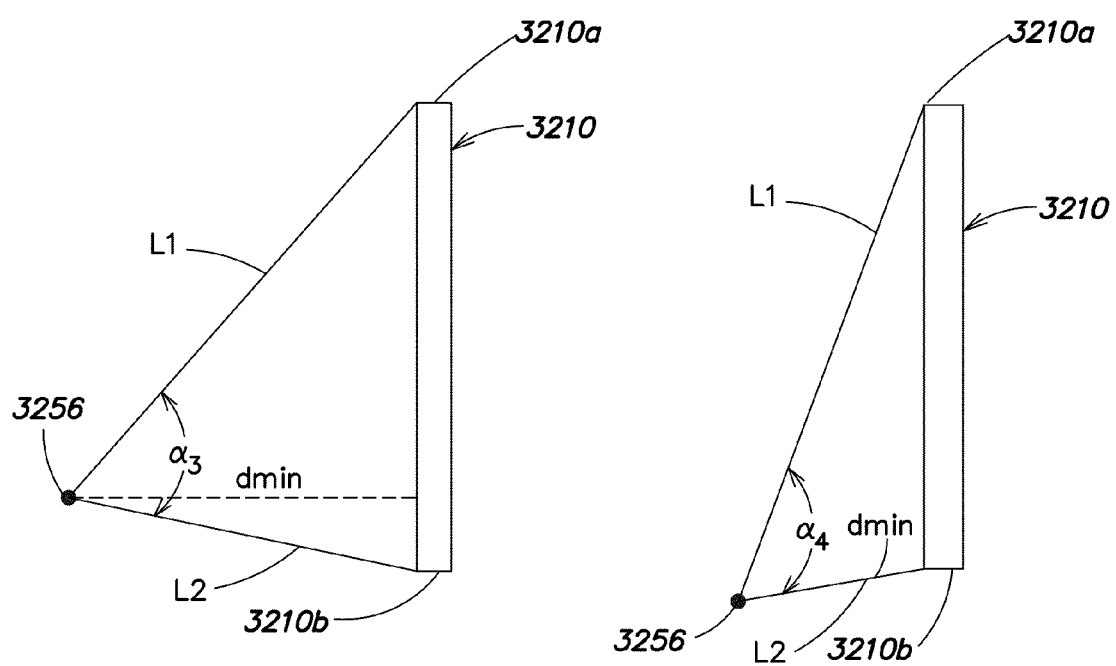
FIG. 32B
FIG. 32C

DUAL ENERGY IMAGING SYSTEM

RELATED APPLICATIONS

This Application claims priority under 35 U.S.C. §119(e) to U.S. Provisional Application Ser. No. 61/176,783, entitled "DUAL ENERGY IMAGING SYSTEM" filed on May 8, 2009, which is herein incorporated by reference in its entirety.

FIELD OF THE INVENTION

The invention relates to X-ray inspection systems that form volumetric images of items under inspection using dual energy x-ray measurements to obtain information on properties of objects in the items.

BACKGROUND OF THE INVENTION

X-ray imaging technology has been employed in a wide range of applications from medical imaging to detection of unauthorized objects or materials in baggage, cargo or other containers generally opaque to the human eye. X-ray imaging typically includes passing radiation (i.e., X-rays) through an object to be imaged. X-rays from a source passing through the object interact with the internal structures of the object and are altered according to characteristics of material the X-rays encounter. By measuring changes in the X-ray radiation that exits the item, information related to characteristics of the material in the item, such as density, atomic structure and/or atomic number, etc., may be obtained.

To measure atomic number, X-ray radiation exiting the object is measured at two or more energy levels. Because materials of different atomic numbers respond differently to X-rays of different energy levels, measuring interaction at multiple X-ray energy levels provides an indication of the atomic number of the material with which the X-ray radiation has interacted. In some X-ray inspection systems used for security screening of baggage or other items, dual energy measurements are used in combination with density measurements to classify objects within an item under inspection. Such systems may use automated detection algorithms to analyze X-ray images that detect objects and classify them as threat or non-threat objects based on size, shape, density and material composition. These systems are called "dual energy systems" because useful distinctions between materials can generally be made using any two energy levels. Though, some dual energy systems make measurements at more than two energy levels.

The energy level of X-rays is determined by characteristics of the components used to generate the X-ray radiation. Some X-ray inspection systems have sources that use electron beams as part of their X-ray generation subsystems. In these systems, an e-beam is directed to impinge on the surface of a target that is responsive to the e-beam. The target may be formed from or plated with, tungsten, molybdenum, gold, metal, or other material that emits X-rays in response to an electron beam impinging on its surface. The target material is one factor that can impact the energy of emitted X-rays. A second factor is a voltage used to accelerate electrons toward the target. An electron beam may be generated, from an electron source called a cathode and a voltage may be applied between the cathode and target to accelerate electrons toward the target.

Some inspection systems employ multiple X-ray generation components, each configured to emit radiation at a different energy level. Though, other inspection systems may employ a switching power supply to change the voltage level within one X-ray generation subsystem to control the subsystem to emit X-rays of different energy levels at different times.

An alternative approach for making multi-energy X-ray measurements is to use different types of detectors. Some detectors are preferentially sensitive to radiation of a specific energy level. The output of such detectors can be taken as an indication of radiation at those energy levels. By illuminating an item under inspection with X-ray radiation over a broad spectrum, the output of detectors sensitive to different energy radiation may be used to form dual energy measurements.

In addition to classifying systems based on whether they form single energy or dual energy images, inspection systems may be classified based on the type of images they form. Multiple types of X-ray inspection systems are known. Two types are projection imaging systems and volumetric imaging systems. In a projection imaging system, an X-ray generating component is positioned on one side of an item under inspection and detectors are positioned on an opposite side. Radiation passes through the item under inspection predominately in a single direction. As a result, an image formed with a projection imaging system is a two-dimensional representation of the item, with objects inside the item appearing as if they were projected into a plane perpendicular to the direction of the X-rays.

In contrast, in a volumetric imaging system, radiation passes through the item under inspection from multiple directions. Measurements of the radiation exiting the item under inspection are collected and, through computer processing, a three-dimensional representation of objects within the item is computed. One class of volumetric imaging system is called a computed tomography (CT) system.

Conventional CT systems establish a circular relationship between an X-ray generating component and X-ray detectors. One approach for forming the circular relationship is to mount both the X-ray generating component and detectors on a rotating gantry that moves relative to the item under inspection. An alternative approach is to control an X-ray generating component to alter the location from which it emits X-ray radiation. Such control can be achieved in an e-beam system by steering the e-beam to strike different locations on the target at different times.

An e-beam may be steered magnetically by bending the beam using one or more magnetic coils, herein referred to as steering coils. In general, the e-beam propagates in a vacuum chamber until the e-beam impinges on the target. Various methods (e.g., bending an electron beam using one or more magnets) of providing an e-beam along a desired path over a surface of the target are well known in the art.

SUMMARY OF INVENTION

Embodiments of the invention provide improved systems and methods for forming dual energy X-ray images. In some embodiments, a scanning e-beam-type system is configured to support dual energy measurements. In some embodiments, the system includes a sequencer that controls beam steering and/or beam shaping components within an X-ray generation subsystem. The sequencer contains multiple scan buffers, each scan buffer storing control values for steering components within the X-ray generation subsystem. Each scan buffer may be associated with a different energy level of radiation to be generated.

In another aspect, the invention relates to an inspection system with different numbers of detectors that are sensitive to X-ray radiation of different energy levels. As an example, a volumetric system may include a sufficient number of detectors at a first energy to form a volumetric image of an item under inspection. A relatively smaller number of detectors sensitive to X-rays at a different energy may be incorporated into the system. An image formed using the detectors at the first energy level may be analyzed to identify objects within the item under inspection. Preferential paths through the item under inspection to the detectors of the second energy level can be identified. In some embodiments, the preferential paths pass through identified objects for which atomic number information is to be used for threat assessment. Radiation travels along the preferential paths pass through these objects without substantial interference from other objects in the item under inspection. Once these paths are identified, points of origin of radiation that travels along these path are identified. Measurements made with the detectors of the second energy level while the X-ray generation subsystem is generating radiation from these points of origin are obtained and used for processing dual energy image data.

Such an approach of making dual energy measurements may be used in systems that can control the point of origin of X-rays through mechanical motion or through steering an electron beam or in any other suitable fashion.

Accordingly, in some aspects, the invention relates to an inspection system with an inspection area. At least one x-ray source is adapted to emit x-ray radiation into the inspection area at a first energy and a second energy. A first plurality of detectors that are more sensitive to x-ray radiation at the first energy level than the second energy level are positioned to receive x-ray radiation from the at least one x-ray source after passing through the inspection area. A second plurality of detectors that are more sensitive to x-ray radiation at the second energy level than the first energy level, the second plurality of detectors are positioned to receive x-ray radiation from the at least one x-ray source after passing through the inspection area. The second plurality detectors consists of fewer detectors than the first plurality of detectors.

In another aspect, the invention relates to a method of operating an inspection system that includes using at least one source and a first plurality of detectors to measure attenuation of x-rays at a first energy by an object in an inspection area. An image of a slice through the object is computed based on the measured attenuation at a first energy. The image is analyzed to determine whether an object of interest is present. When an object of interest is present, a source position and a detector of a second plurality of detectors are selected such that a path between the selected source position and selected detector passes through the object of interest. A source of the at least one source is positioned in the selected source position and attenuation of x-rays at a second energy by the object in the inspection area is measured using the positioned source and the selected detector of the second plurality of detectors; and An atomic number of the object is computed based on the measured attenuation of the second energy and a portion of the measured attenuation at the first energy level.

In another aspect, the invention relates to a method of operating an inspection system. During a first phase of a scan cycle, a first voltage is applied to an x-ray source and an electron beam is steered across a target within the x-ray source by applying first control values to control elements within the x-ray source. The first control values are obtained from a first set of stored control values. During a second phase of the scan cycle, a second voltage is applied to the x-ray source. An electron beam is steered across the target by applying second control values to the control elements within the x-ray source, the second control values being obtained from a second set of stored control values.

In yet a further aspect, the invention relates to a system comprising an electron beam generator, a target and a voltage source coupled to the electron beam generator and the target. The voltage source is adapted to output a first voltage and a second voltage. The system also includes beam control components adapted to control characteristics of the electron beam as it strikes the target. A computer storage medium adapted to store a first sequence of control values and a second sequence of control values is also included. A timer adapted to provide an output. A selector, coupled to the output of the timer and to the computer storage medium, in response to the output of the timer, selects a control value from the first sequence of control values and applies the selected control value to the beam control components to control the beam when the voltage source outputs the first voltage and selects a control value from the second sequence of control values and applies the selected control value to the beam control components to control the beam when the voltage source outputs the second voltage.

The foregoing is a non-limiting summary of the invention and one of skill in the art will recognize other inventive concepts in the following description.

BRIEF DESCRIPTION OF THE DRAWINGS

FIGS. 8-16 illustrate various portions of an x-ray generation subsystem using dual electron beam generators, in accordance with various embodiments of the present invention;

FIGS. 32A-32C illustrate various concepts for reducing the sweep angle and minimum distance between the exit port of an electron beam generator and the target, in accordance with various aspects of the present invention;

DETAILED DESCRIPTION

Figure 1:
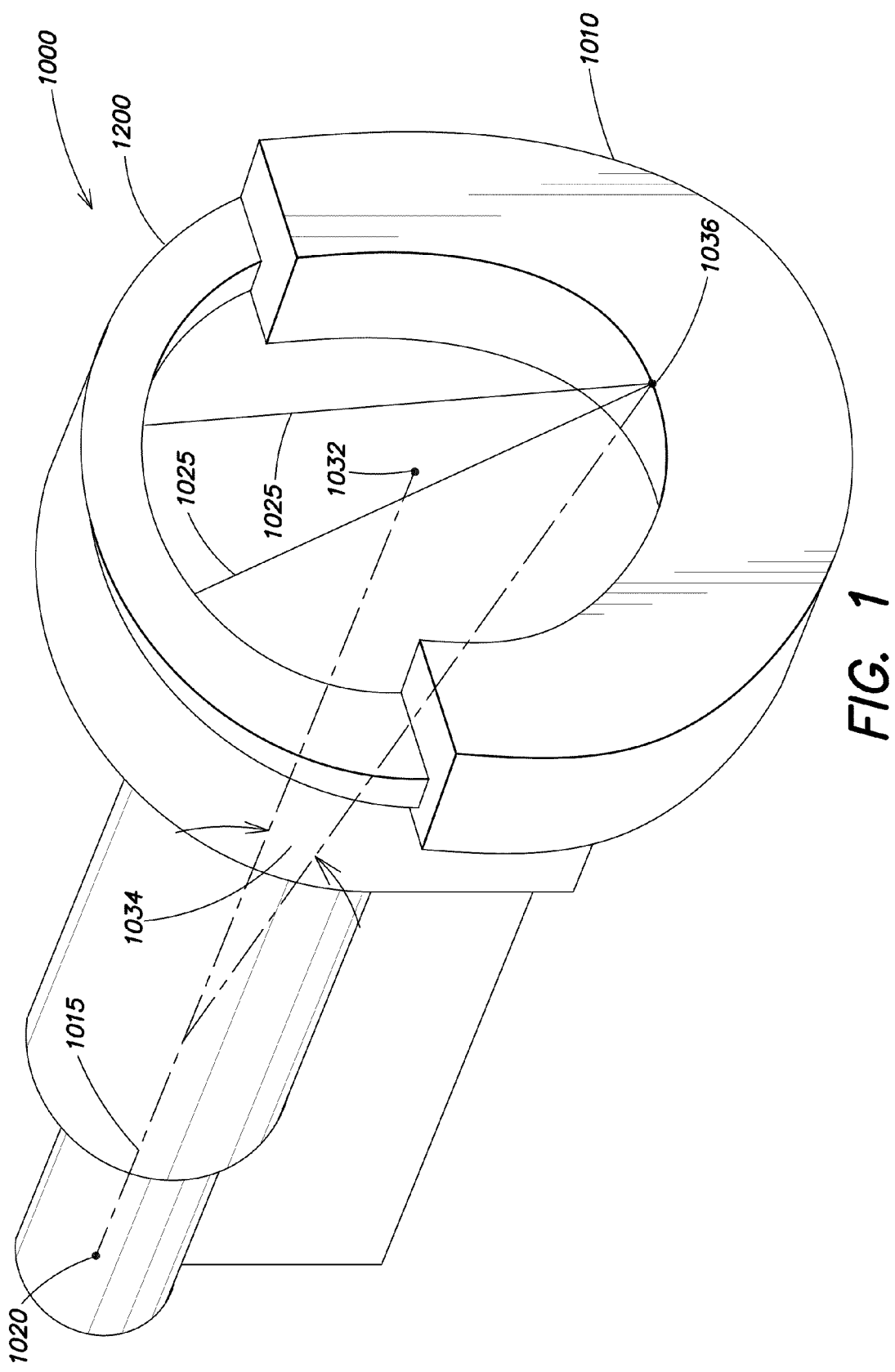
FIG. 1 illustrates a conventional circular geometry x-ray generation subsystem using e-beam technology.

As discussed above, conventional volumetric X-ray inspection systems employ a circular geometry between detector and an X-ray generation subsystem so that measurements can be made on an item under inspection from multiple directions. FIG. 1 illustrates schematically an X-ray inspection system employing e-beam technology in a circular geometry. X-ray inspection system 1000 includes an essentially circular target 1010 that responds to an impinging e-beam 1015 by emitting X-rays 1025 and an essentially circular array 1200 of detectors responsive to the radiation.

E-beam 1015 emanates from an e-beam point of origin 1020, for example, from an electron gun and is directed essentially along a longitudinal axis that penetrates a center point 1032 of the detector array (or target). One or more magnetic coils (not shown) deflect the e-beam from the longitudinal axis at a deflection angle 1034 so that the e-beam impinges on target 1010, for example, at location 1036 on the target. The resulting X-rays then penetrate an inspection region and impinge on the detector array. The X-ray generation subsystem may then be rotated in a number of ways such that the e-beam impinges at different locations on the target to form a scanning path along the target. As the e-beam is directed along a circular arc of the target, the resulting X-rays penetrate the inspection regions at different angles to provide different projections or views of an object positioned within the inspection region. Other circular geometry systems and methods related to e-beam scanning are described in U.S. Pat. No. 5,491,734 ('734) to Boyd et al., U.S. Pat. No. 4,352,021 ('021) to Boyd et al., and U.S. Pat. No. 6,735,271 ('271) to Rand et al., all of which are incorporated herein by reference in their entirety.

Various technical constraints, including the expense of the steering coils and characteristics of bending the e-beam limit the amount the e-beam can be practicably deflected. That is, design specifications may be deflection angle limited.

Accordingly, the distance between an e-beam source and the target is often extended so that deflection angle constraints can be met, while still accommodating a particular detector array circumference. For example, the distance between e-beam point of origin 1020 and center point 1032 may be increased so that a smaller deflection angle is sufficient to allow the e-beam to impinge on target 1010. However, the vacuum tubes and the corresponding apparatus needed to enclose the path of the e-beam are relatively expensive and bulky. In addition, the extended vacuum region has relatively long field-free paths between the e-beam point of origin and the target, which require more extensive shielding and may be susceptible to stray electromagnetic (EM) fields. As a result, such systems are more costly to manufacture and more cumbersome to deploy due to the increased footprint, shielding requirements, etc.

Applicant has appreciated that arbitrary, and more particularly, non-circular geometries offer a number of benefits with respect to the flexibility of the design and may facilitate more compact and inexpensive X-ray detection systems. Applicant has identified and developed various e-beam techniques for use in arbitrary geometry systems that facilitate relatively inexpensive, compact and efficient X-ray detections systems.

In one embodiment, an X-ray generation subsystem is provided wherein X-rays are generated by directing an e-beam along a target via a scanning path that includes at least one substantially circular portion and at least one non-circular portion. One exemplary system includes a scanning path having a plurality of substantially linear portions and a plurality of substantially circular portions. For example, the scanning path may traverse a substantially rectangular U-shaped target formed from three substantially linear segments connected by substantially circular segments.

In another embodiment, an X-ray generation subsystem having a target that converts energy in an e-beam to X-ray energy is provided as a plurality of segments. In one exemplary configuration, the target comprises at least one substantially circular segment and at least one substantially linear segment. In some embodiments, the plurality of segments are provided continuously. In other embodiments, at least one of the plurality of segments is discontinuous with at least one other segment. For example, each segment may be offset in a direction parallel to the direction of conveyance of an item being inspected by the X-ray generation subsystem.

In another embodiment, an X-ray generation subsystem is provided wherein X-rays are generated by directing an e-beam along a target responsive to the e-beam at a variable scan rate. In one exemplary configuration, the e-beam traverses the target according to a scanning schedule that varies the scan rate to synchronize the scanning with a conveying apparatus such that a single traversal of the target generates X-rays that penetrate substantially the same cross-section of the item being scanned. In another exemplary configuration, the e-beam traverses the target according to a scanning schedule that varies the scan rate to generate X-rays having substantially similar penetration angles with respect to a center point of the inspection area of the X-ray generation subsystem.

Figure 2:
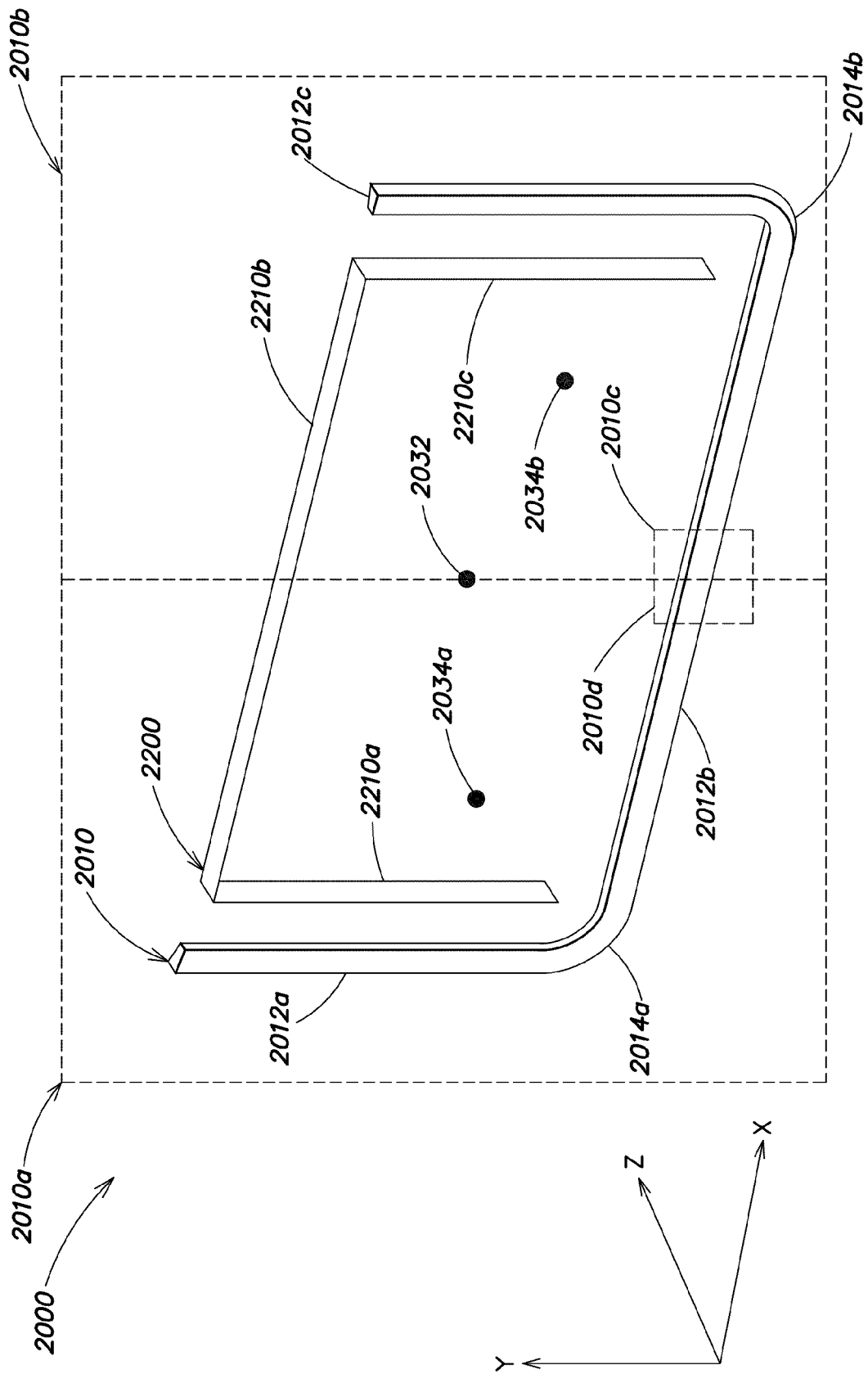
FIG. 2 illustrates an arbitrary geometry target and detector array using e-beam technology, in accordance with one embodiment of the present invention.

FIG. 2 illustrates portions of an exemplary X-ray generation subsystem, in accordance with one embodiment of the present invention. X-ray generation subsystem 2000 includes a non-circular detector array 2200. In particular, detector array 2200 is generally shaped as a rectangular U, sometimes referred to as goal posts, or staple-shaped, comprising substantially linear segments 2210a, 2210b and 2210c. The U-shaped geometry is merely exemplary of an arbitrary geometry array, which as the name suggests, may take on any shape, as the aspects of the invention are not limited in this respect. The various segments of the detector array may be continuous or they may be staggered, for example, along the z-axis, as described in further detail below. To irradiate the detector array 2200, a target 2010 that generally mimics the shape of detector array 2200 is positioned concentrically and diametrically from the detector array and operates as the e-beam anode.

The term "diametric" refers herein to positioning of a target and detector array in an opposing arrangement such that diametric portions of the detector array and target are generally facing one another such that x-rays emitted from the portions of the target impinge on the diametrically arranged portions of the detector array. Target 2010 includes substantially linear segments 2012a, 2012b, and 2012c and circular arc segments 2014a and 2014b. Accordingly, linear segment 2210c of the detector array is arranged diametrically to linear segment 2012a because the x-ray sensitive regions of the detectors on segment 2210c are facing target segment 2012a. Similarly, segments 2010b and 2010c of the detector array are arranged diametrically to circular segment 2014a of the target. As discussed above, target 2010 may be formed from any material that converts energy from an impinging e-beam into X-rays, such as tungsten, molybdenum, etc.

To minimize the deflection angle without unduly compromising the size of the inspection area, Applicant has appreciated that multiple e-beam generators, also referred to as electron guns, may be used. In addition, if the required deflection angle may be reduced for a given size target, then, rather than reducing the deflection angle, the same actual deflection angle may be used and the distance between the steering coils and the target may be reduced, as discussed in further detail below. This reduction in distance allows the vacuum tubes through which the e-beams travel after leaving the steering coils to be made smaller, substantially reducing both the cost and bulk of the resulting generation subsystem.

For example, a first electron gun may be deployed to scan portion 2010a of target 2010 and a second electron gun may be deployed to scan portion 2010b. In one embodiment, each electron gun scans substantially half of the target, and in a sequential fashion. By positioning the electron gun pair to scan substantially half of the array, the deflection angles for each gun may be reduced. For example, the electron guns may be positioned such that the e-beam would impinge somewhere along the respective target in the absence of deflection forces, rather than passing through, for example, a center point of the inspection region.

Alternatively, the electron beams, in the absence of deflection forces, may pass through points closer to respective portions of the target, rather than passing through the center point, or other points generally equidistant from various points along the target. For example, rather than having a single electron gun positioned such that the generated e-beam, in the absence of deflection forces, passes through a center points 2032 (as shown in FIG. 2), a pair of electron guns may be positioned such that their e-beams, in the absence of deflection forces, pass through points 2034a and 2034b, respectively. Multiple e-beam generators may be used in numerous configurations to reduce the required deflection angle and/or reduce vacuum tube sizes, as discussed in further detail below.

Figure 29:
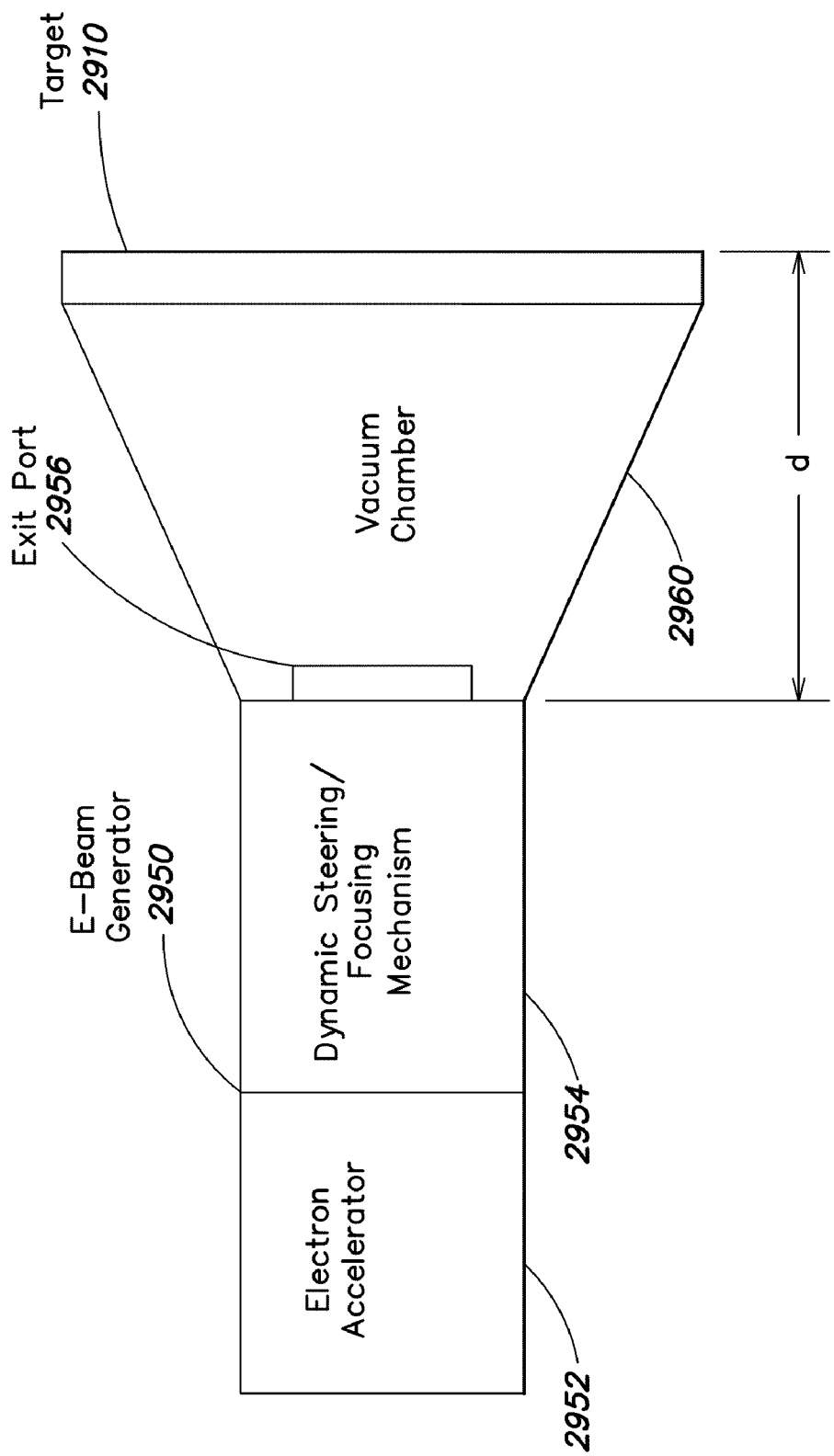
FIG. 29 illustrates an electron beam generator, in accordance with one embodiment of the present invention.

FIG. 29 illustrates an e-beam generator adapted to sweep an e-beam along a target to generate X-rays used to inspect objects of interest. The e-beam generator includes an electron accelerator 2952 adapted to accelerate electrons to an appropriate velocity to create an electron beam suitable for impinging on the target. Various electron/particle accelerators are well known in the art. As described in more detail below, electrons may be accelerated towards target 2910 by application of a voltage between the e-beam generator and target 2910. The level of that voltage may be varied to control the energy levels of X-rays emitted. It should be understood that other acceleration mechanisms that provide a means for varying the acceleration may be used instead of such voltage control.

After the electrons have been suitably accelerated, the electrons may be directed into dynamic steering/focusing mechanism 2954, referred to hereinafter as the steering mechanism. The steering mechanism is configured to bend the path of the electron beam (e.g., using magnetic steering coils) such that the electron beam impinges on target 2910 along a desired scanning path (e.g., from top to bottom of the target). The steering mechanism may also implement focusing components to focus the electrons into a generally desirable shaped beam having a suitable focal point. The electron accelerator and the steering mechanism is collectively referred to as the e-beam generator 2950 or electron gun, which, unless specifically stated otherwise are synonymous terms.

After the e-beam exits the steering mechanism through the exit port 2956, the e-beam propagates through vacuum tube 2960 to impinge on target 2910. Vacuum tube 2960 is generally a relatively expensive and bulky component. The larger the vacuum tube, the more expensive and bulky the x-ray generation subsystem becomes. The size of the vacuum tube is related to the distance between the exit port and the target, which is in turn related to the necessary deflection angle. Applicant has appreciated that by using multiple e-beam generators, the distance between the steering mechanism (e.g., the distal end of the e-beam generator) and the target may be reduced, thus reducing the size of the vacuum tube, facilitating a less expensive x-ray generation subsystem having a smaller footprint.

Figure 30A:
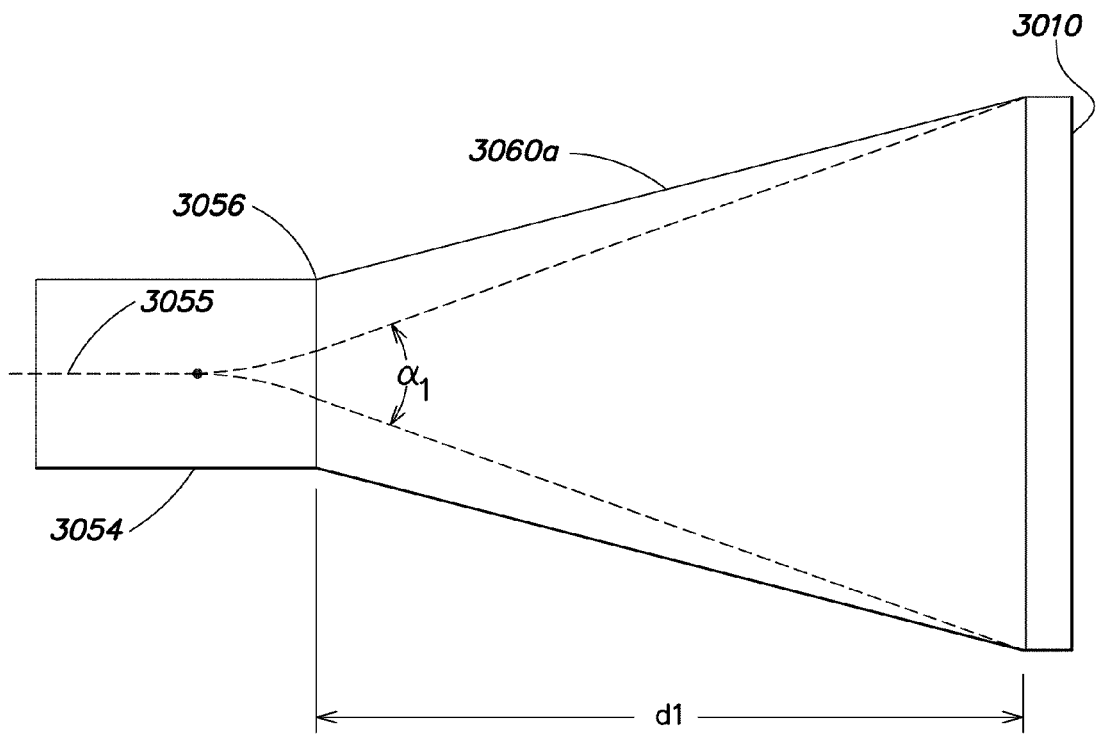
FIGS. 30A and 30B illustrate reducing the size of the vacuum tube in an electron beam generator using various aspects of the present invention.
Figure 30B:
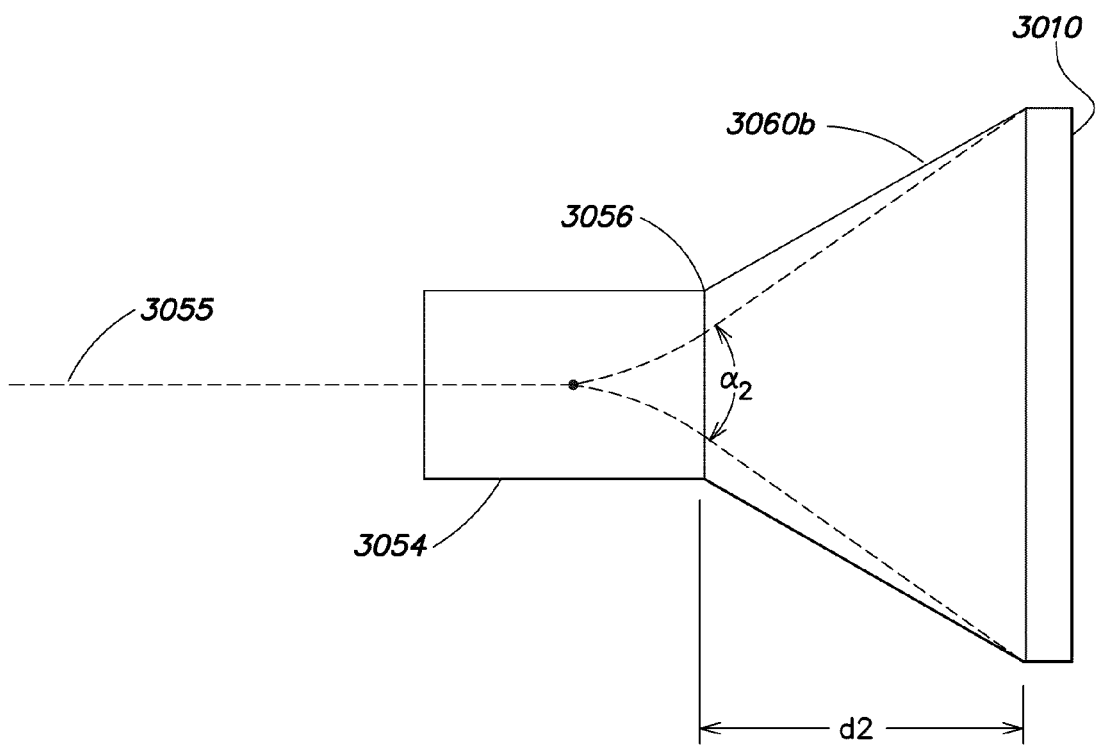

FIGS. 30A and 30B illustrate the relationship between deflection angle and the distance between the e-beam generator and the target. In FIG. 30A, a steering mechanism 3054 bends an e-beam 3055 at a deflection angle $\alpha_1$. It should be appreciated that once the e-beam is no longer under the forces of the steering coils, the trajectory of the e-beam becomes substantially linear. The point at which an e-beam is no longer under the effects of the steering coils (e.g., when the e-beam trajectory is essentially linear and has effectively no curvature) is referred to as the exit point of the e-beam, and is situated at the exit port 3056 of the steering mechanism.

In FIG. 30A, a vacuum tube 3060a having a length $d_1$ is needed to accommodate the e-beam generated with deflection angle $\alpha_1$ such that the entire sweep of target 3010 may be scanned. FIGS. 30A and 30B may be a top view of an e-beam generator target combination. For example, target 3010 may be the cross-bar of a substantially U-shaped or rectangular shaped target (e.g., portion 2012b illustrated in FIG. 2). In FIG. 30B, the deflection angle is increased to $\alpha_2$. As a result, vacuum tube 3060b need only have a length $d_2$ to accommodate the e-beam. Accordingly, as the deflection angle is increased, the distance between the exit port 3056 and target may be reduced and the vacuum tube may be decreased in size. Thus, if the constraints on the deflection angle are relaxed, the deflection angle may be held constant while decreasing the distance between the exit point and the target.

Figure 31A:
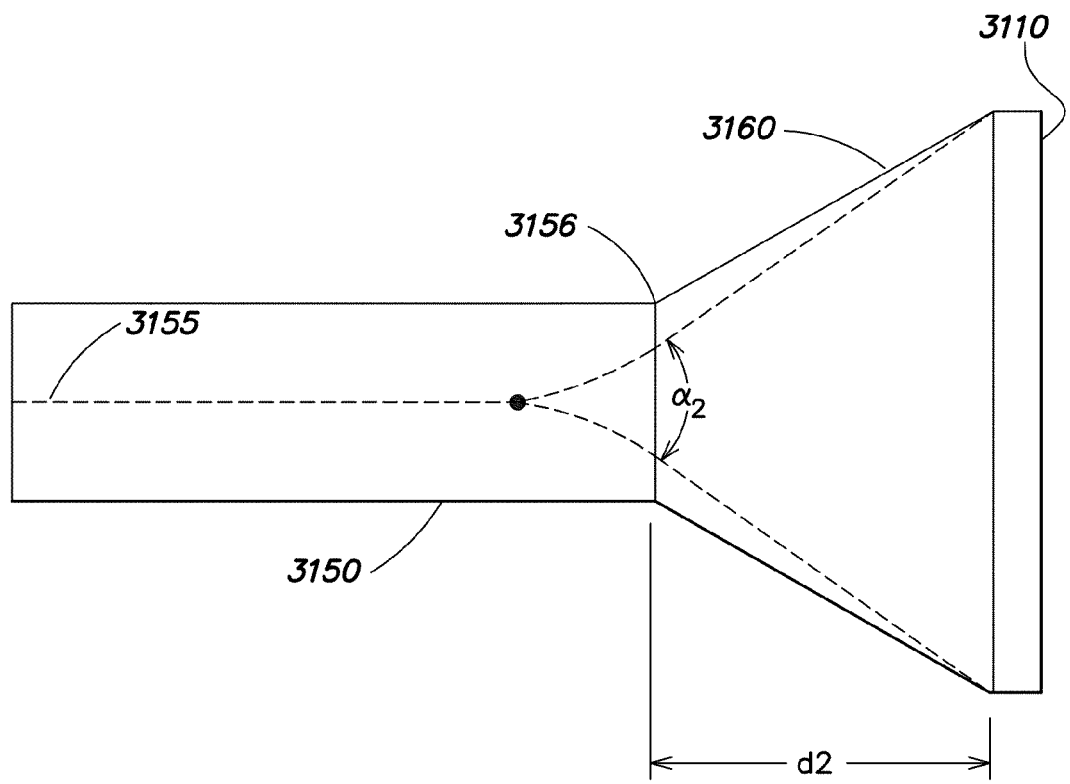
FIGS. 31A and 31B illustrate reducing the size of the vacuum tube in an electron beam generator using various aspects of the present invention related to dual electron beam generators.
Figure 31B:
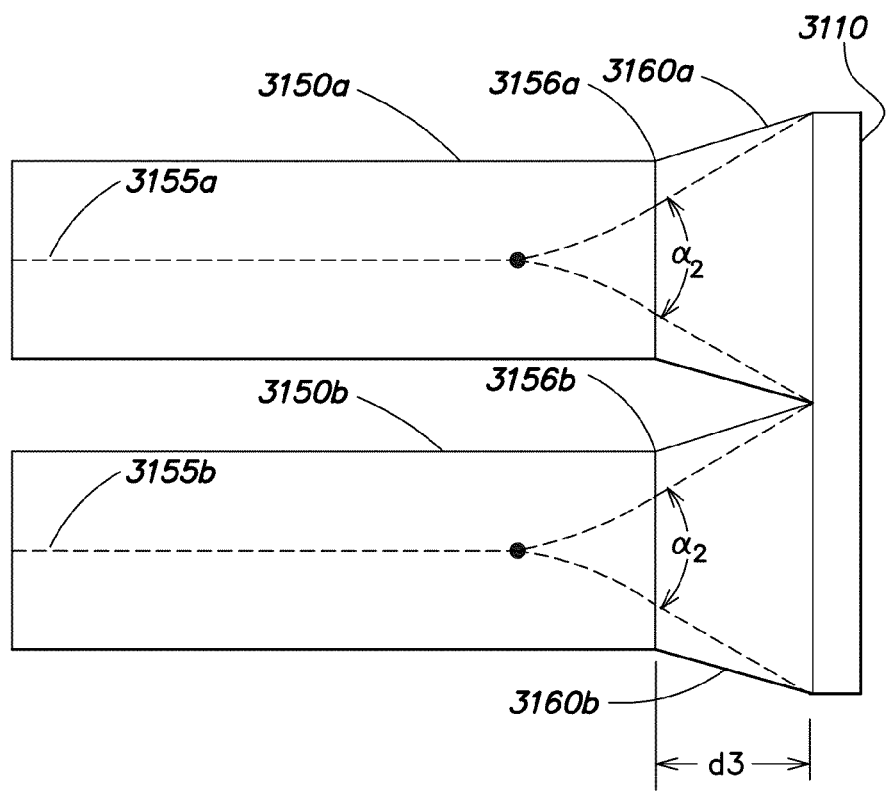

For example, FIG. 31A illustrates a configuration wherein a single e-beam generator 3150 is responsible for scanning target 3110. At a deflection angle $\alpha_2$, the vacuum tube 3160 needs a length of $d_2$ to accommodate the e-beam as described in FIG. 30B. In FIG. 31B, two electron generators 3150a and 3150b are arranged to scan essentially half of target 3110. As a result, the deflection angle required to cover the half of the target 3110 that each e-beam generator is respectively responsible for scanning may be reduced. However, rather than decreasing the deflection angle, the e-beam generators may be moved closer to the target. Accordingly, at deflection angle $\alpha_2$, vacuum tubes 3160a and 3160b may accommodate the respective e-beams with a distance $d_3$ that is substantially less than distance $d_2$. Thus, the x-ray generation subsystem may be made more compact.

It should be appreciated that the two vacuum tubes 3160a and 3160b together have an area smaller than the area of single vacuum tube 3160. Accordingly, the two vacuum tubes not only facilitate a reduced footprint x-ray system, but may facilitate the manufacture of a less expensive x-ray system. While the advantage gained by using multiple e-beams is exploited to reduce the length of the vacuum tube, it may also be used to decrease the deflection angle that the steering coils need achieve. In particular, the length of the vacuum tube may remain the same as in single e-beam generator configurations while reducing the deflection angle. In addition, some combination of vacuum tube length reduction and deflection angle reduction may be used together. That is, the benefits accorded by multiple e-beam generators may be shared between reducing deflection angle and/or reducing the distance between the exit point and the target, in any amount or combination, as the aspects of the invention are not limited in this respect.

Applicant has appreciated that configurations made possible by multiple e-beam generators facilitate further reduction in deflection angle and/or vacuum tube size. FIG. 32A illustrates an e-beam generator 3250 arranged to scan target 3210. For example, target 3210 may be the portion of the target 3110 that e-beam generator 3150a is responsible for scanning or another portion of a target (e.g., target 3210 may be portion 2012a of target 2010 illustrated in FIG. 2). E-beam generator 3250 is positioned generally symmetric to target 3110. In particular, the length $L_1$ of the line connecting center point 3256 (i.e., the point at which the e-beam begins being bent by the steering mechanism) to one extreme of the target 3210 and the length $L_2$ of the line connecting center point 3256 and the other extreme of the target 3210 are substantially equal. The two lines of length $L_1$ and $L_2$ respectively define the sweep of the electron beam and is related to the required deflection angle imposed on the steering mechanism. In addition, the minimum distance $d_{min}$ between center point 3256 and the target is along the line from the center point to the center of the target.

Applicant has appreciated that by re-configuring the location of the e-beam generator, the sweep of the e-beam may be reduced, thus reducing the deflection angle required of the steering mechanism. In addition, the minimum distance between the e-beam generator and the target may be decreased, thus facilitating more compact vacuum tube construction. In particular, asymmetrical placement of e-beam generators allows the reduction of the sweep required by the steering mechanism and reduces the length of the vacuum tube needed to accommodate the e-beam. FIGS. 32B and 32C illustrate e-beam generator configurations, in accordance with the various embodiments of the present invention.

In FIG. 32B, the e-beam generator has been positioned such that the center point 3256 is located closer to extreme 3210b of target 3210 then to extreme 3210a of target 3210. As a result, the sweep of the e-beam as defined by $\alpha_3$ is smaller than the sweep of the e-beam in FIG. 31A (as defined by $\alpha_2$). As a result, the configuration imposes reduced deflection angle requirements on the steering mechanism. In addition, the minimum distance $d_{min}$ in FIG. 32B has been reduced from the minimum distance in the configuration illustrated in FIG. 32A. Accordingly, the reduced sweep angle and minimum distance facilitate smaller and more compact construction for the x-ray generation subsystem, and more particularly, smaller more compact vacuum tube construction.

In FIG. 32C, the e-beam is moved even further in the direction of extreme 3210b. As expected, both the sweep angle $\alpha_4$ and the minimum distance are smaller than the configuration in FIG. 32B. It should be appreciated that as the e-beam generator is positioned asymmetrically with the target, the e-beam will impinge on the detector array at increasingly oblique angles, effecting the eccentricity of the focal spot. To compensate for changes in the focal spot of the e-beam, the steering mechanism may include focusing means to reshape the electron beam to compensate for the oblique angles at which the e-beam impinges on the target. As discussed above, reductions in required deflection angles may be exploited as actual deflection angle requirements, as reductions in distance between the e-beam generator and the target, or a combination of both. Various configurations that utilize concepts related to asymmetric positioning of the e-beam generator are shown in FIGS. 14 and 25-27, which are discussed in further detail below.

As discussed above, multiple e-beam generators may be arranged to scan substantially half of a target. In another embodiment, each electron gun scans more than half of the target. For example, it may be desirable for the path of the electrons guns to overlap in a region that includes the seam between the portions of the target that the electrons are respectively responsible for scanning. To achieve the overlap, the first electron gun may provide an e-beam along a path to scan portion 2010a and a relatively small region 2010c extending into portion 2010b. Similarly, the second electron gun may provide an e-beam along a path to scan portion 2010b and a relatively small region 2010d extending into portion 2010a. Information obtained from the resultant overlap region in the two scan paths allows for interpolation so that attenuation values are relatively smooth across the transition point in the paths of the respective electrons guns. However, an overlap region need not be employed, as the aspects of the invention are not limited in this respect.

The application of multiple electron guns allow each beam to be deflected less to reach desired locations along the target. As a result of the reduced deflection angle, the electron guns may be positioned closer to the target, decreasing the length and size, generally, of the vacuum tube(s) and the associated apparatus. In one embodiment, the field-free path of the e-beam from the electron gun to the anode may be reduced approximately by a factor of two, resulting in a less expensive, more compact X-ray generation subsystem. For example, the smaller vacuum tubes and reduced shielding requirements facilitate less expensive construction having a reduced footprint.

In one embodiment, a pair of electron guns is housed in a single vacuum tube and is positioned and oriented to scan respective portions of the target via the same vacuum tube. In an alternative embodiment, each of a pair of electron guns are housed in respective and independent vacuum tubes, disposed to scan respective portions of the target. Other electron gun/vacuum tube arrangements may be used, as the aspects of the invention are not limited in this respect. FIGS. 8-16 illustrate various arrangements of an X-ray system employing two e-beam generators (guns), in accordance with different embodiments of the present invention. In the embodiments illustrated in FIGS. 8-16, the target is substantially horseshoe shaped and the detector array is substantially u-shaped. However, it should be appreciated that both the target and detector array may be of substantially the same shape, or of different shapes not illustrated herein, as the aspects of the invention are not limited in this respect.

Figure 14A:
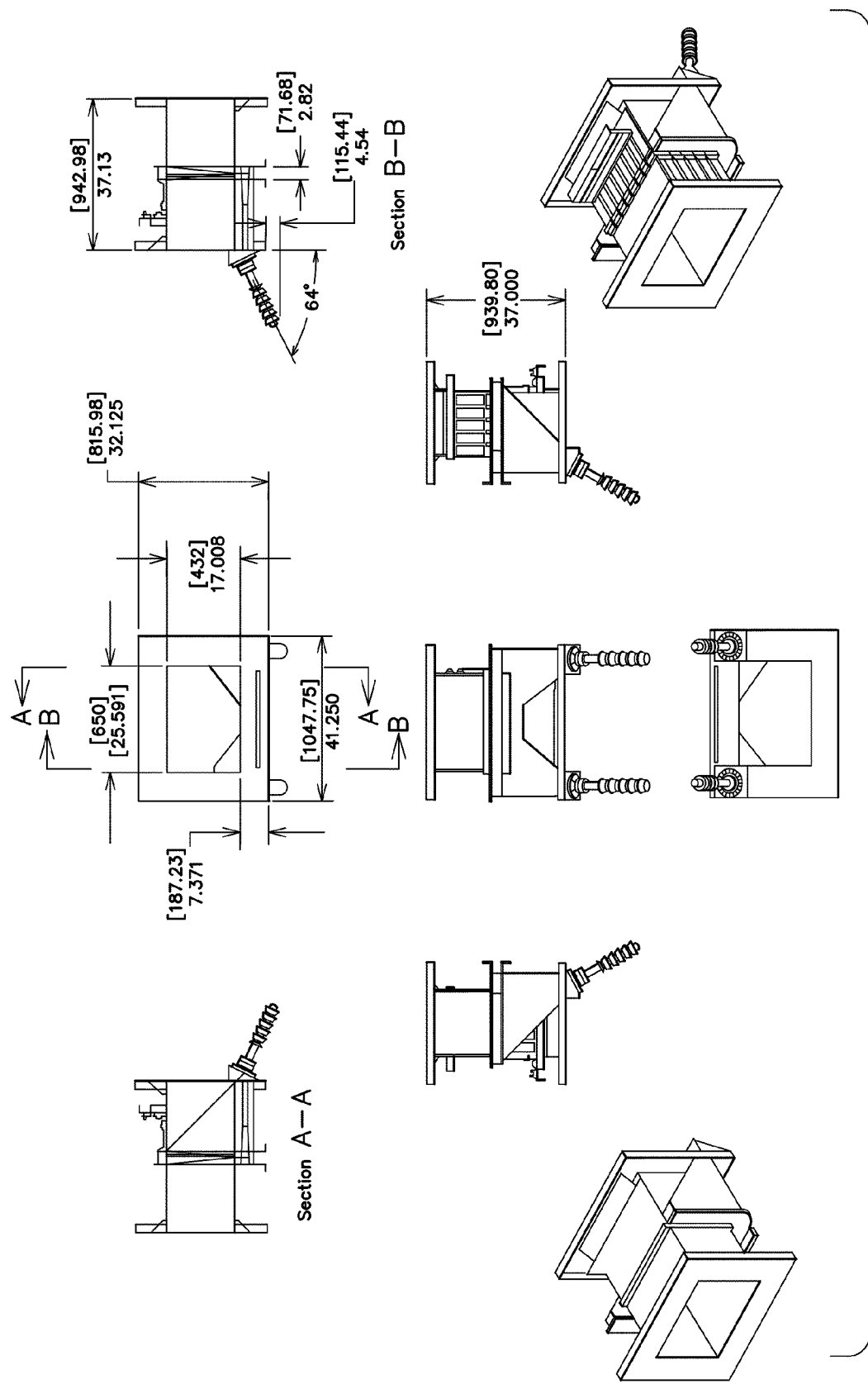

FIG. 14A illustrates a configuration that utilizes various aspects of asymmetric positioning of e-beam generators. Different views of portions of an x-ray detection system illustrated in FIG. 14A are illustrated in greater detail in FIGS. 14B-14F. In particular, FIG. 14B illustrates a side view of one e-beam generator. E-beam generator 1450*a* is arranged to provide an e-beam to impinge on a portion of a target 1410. E-beam generator 1450*a* is positioned closer to target extreme 1410*b* then target extreme 1410*a* to reduce the sweep angle of the e-beam generator. As shown, the boundary of vacuum tube 1460*a* from the e-beam generator to target extreme 1410 forms substantially a right angle with the target. However, other configurations are possible, as the aspects of the invention are not limited in this respect.

Figure 14D:
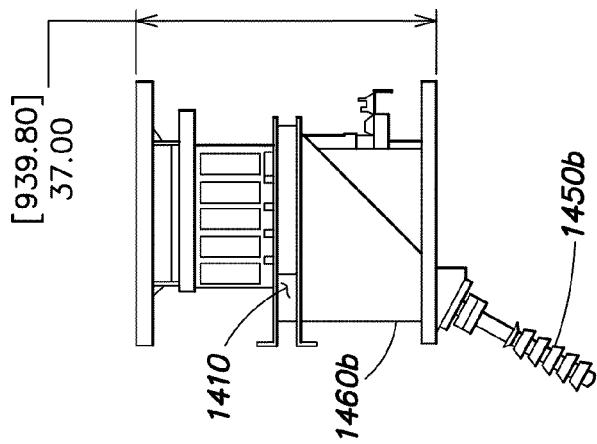
Figure 14C:
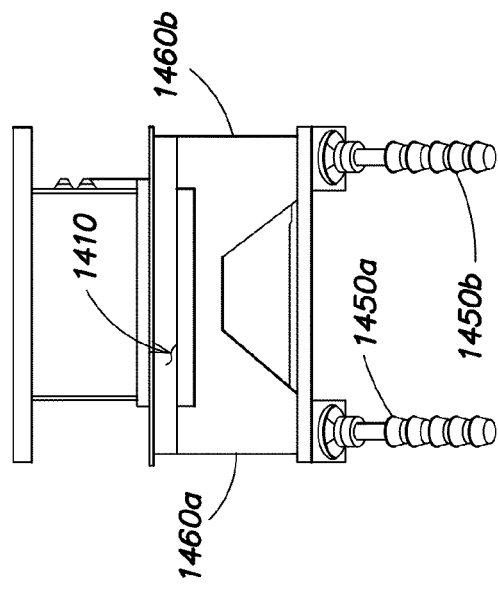
Figure 14B:
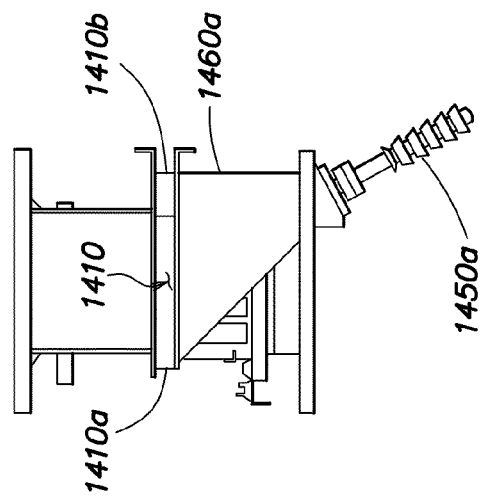
Figure 14E:
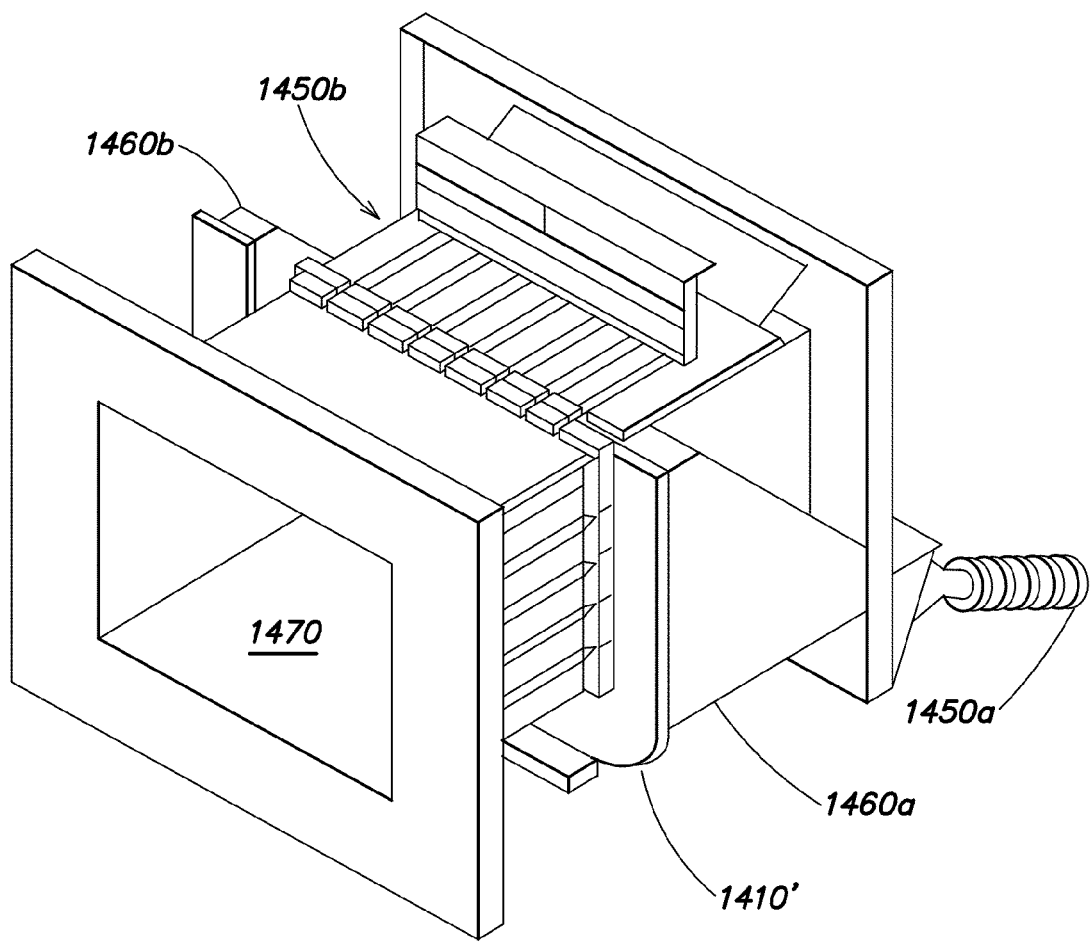
Figure 17:
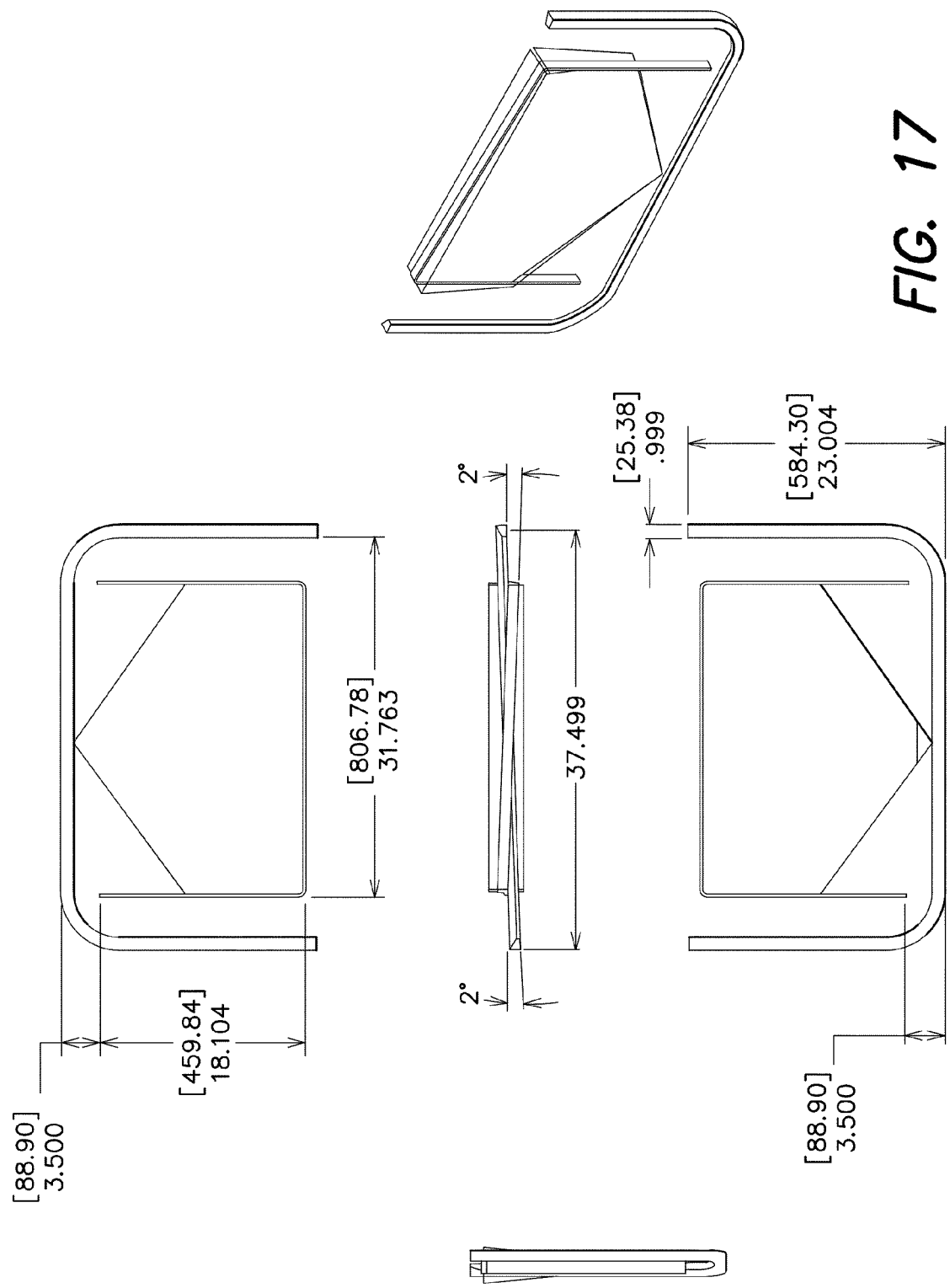
FIGS. 17-23 illustrate various configurations utilizing rotation between the target and the detector array, in accordance with various embodiments of the present invention.
Figure 18:
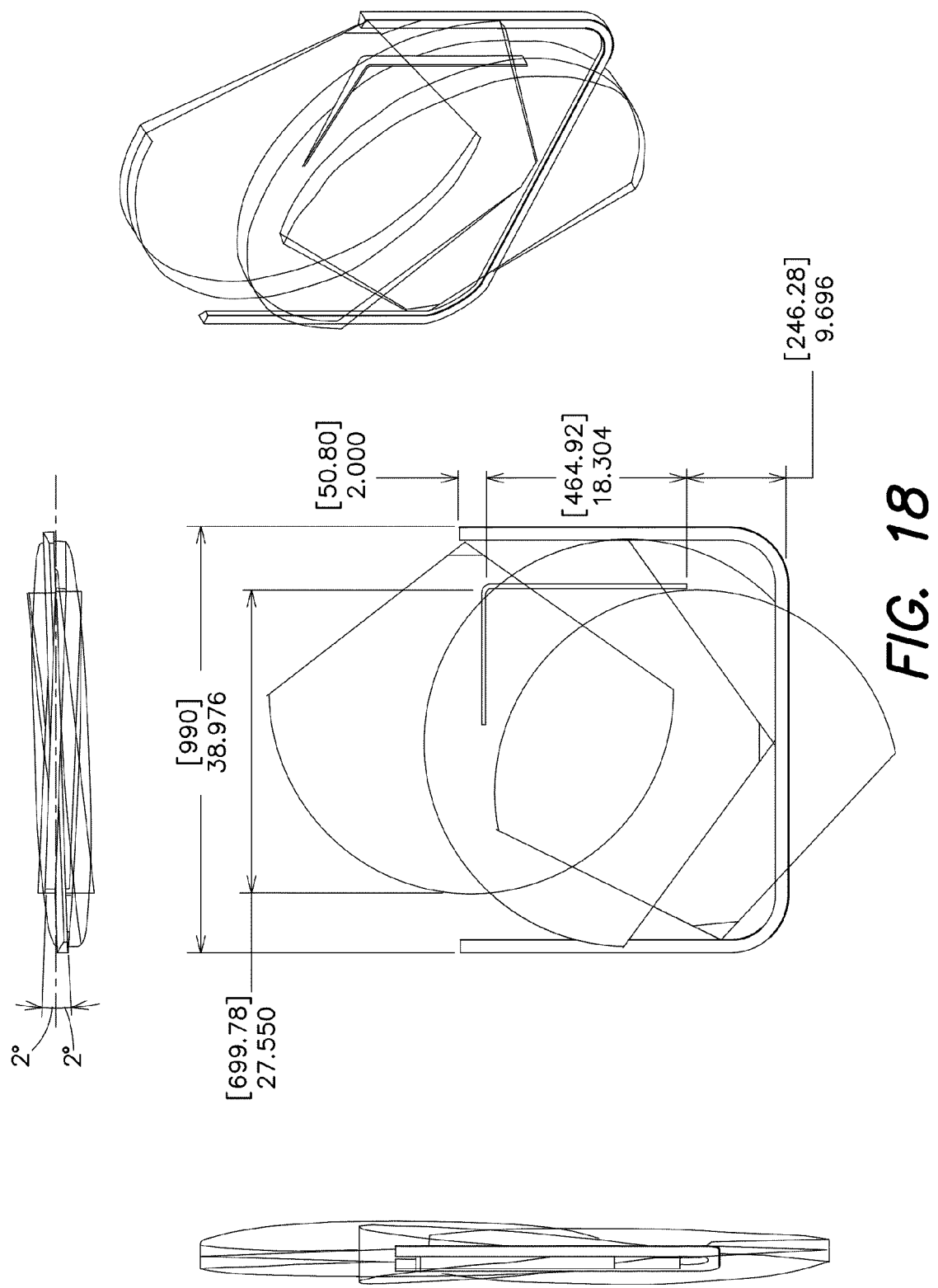
Figure 19:
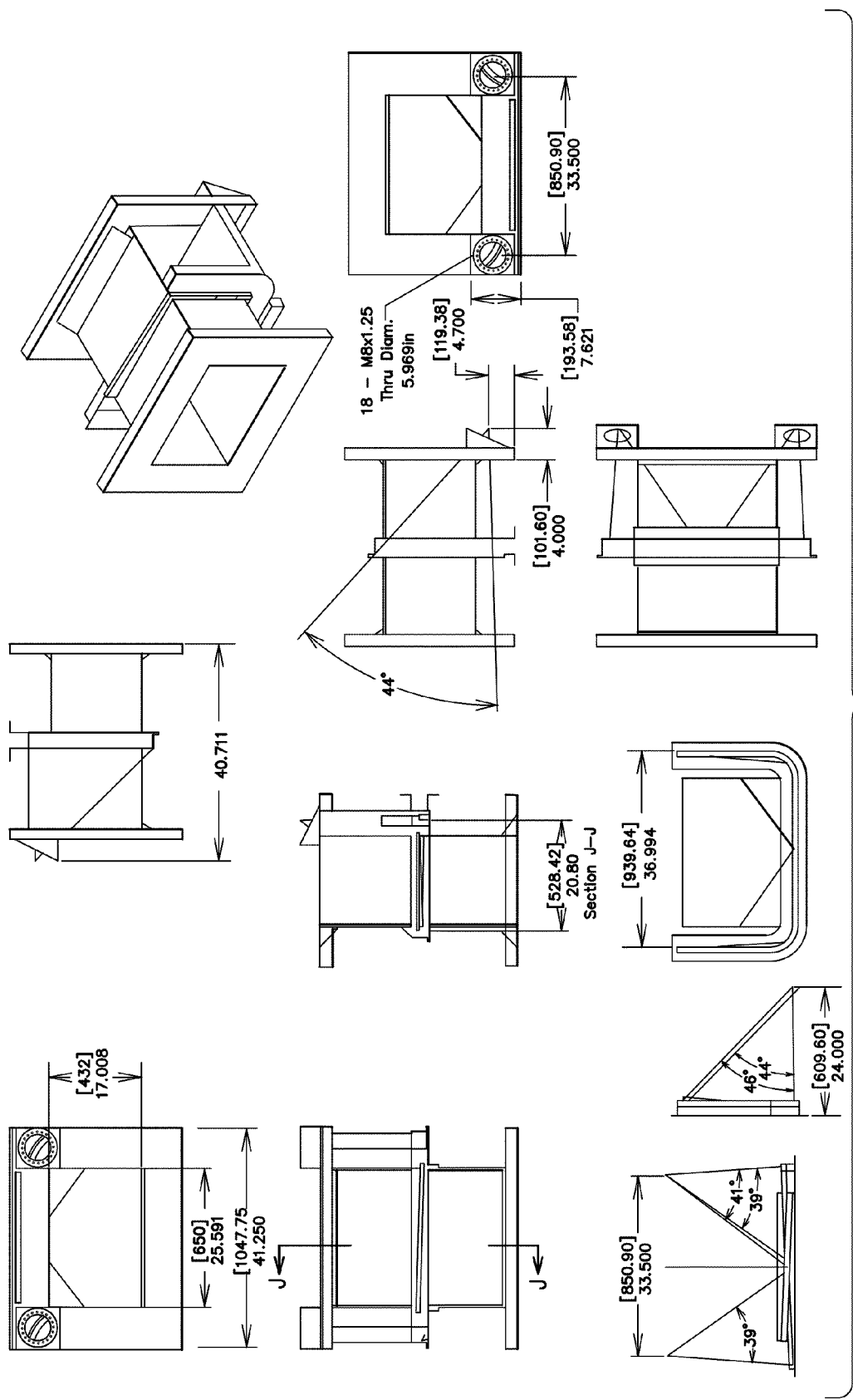
Figure 20:
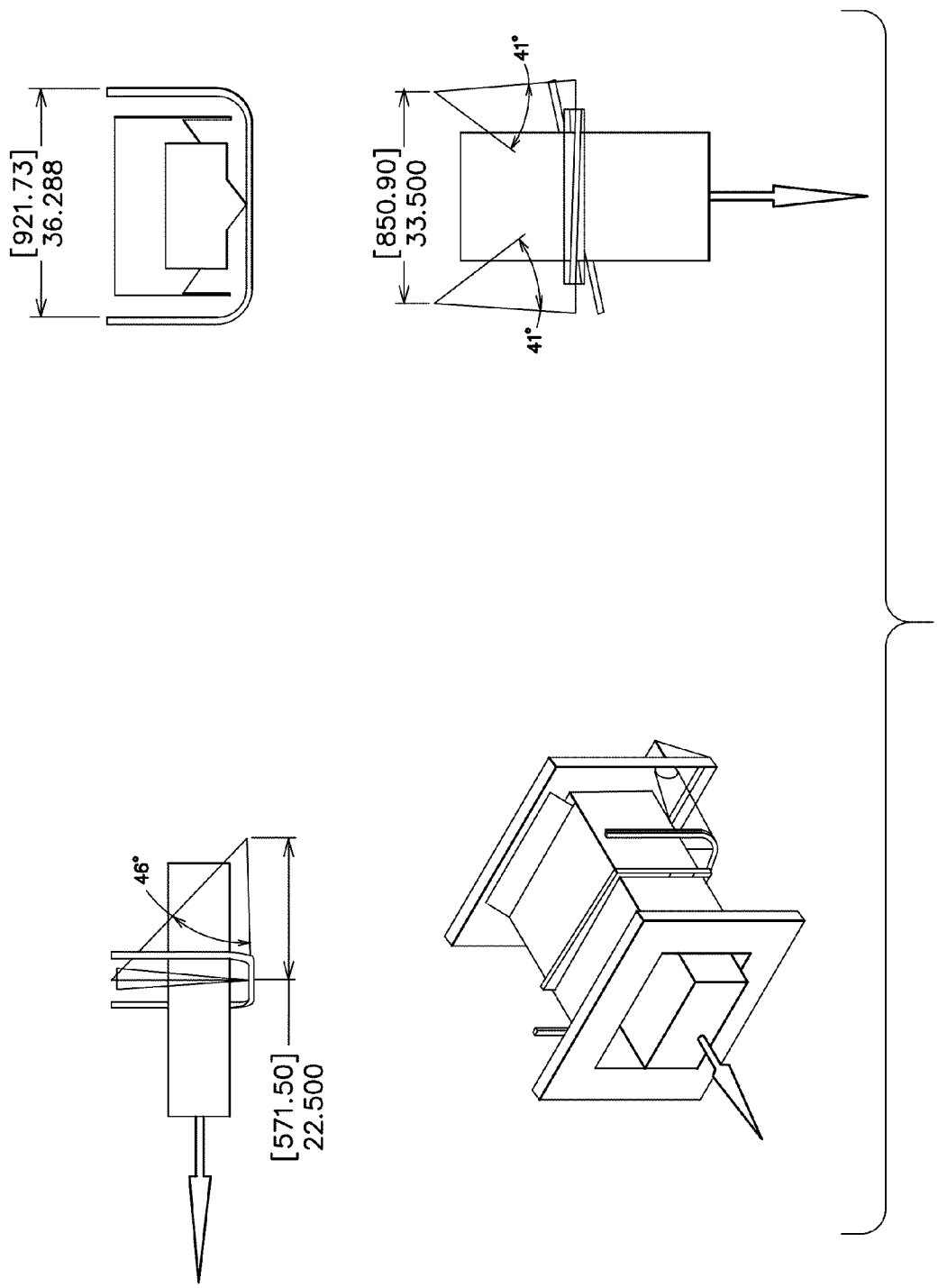
Figure 21:
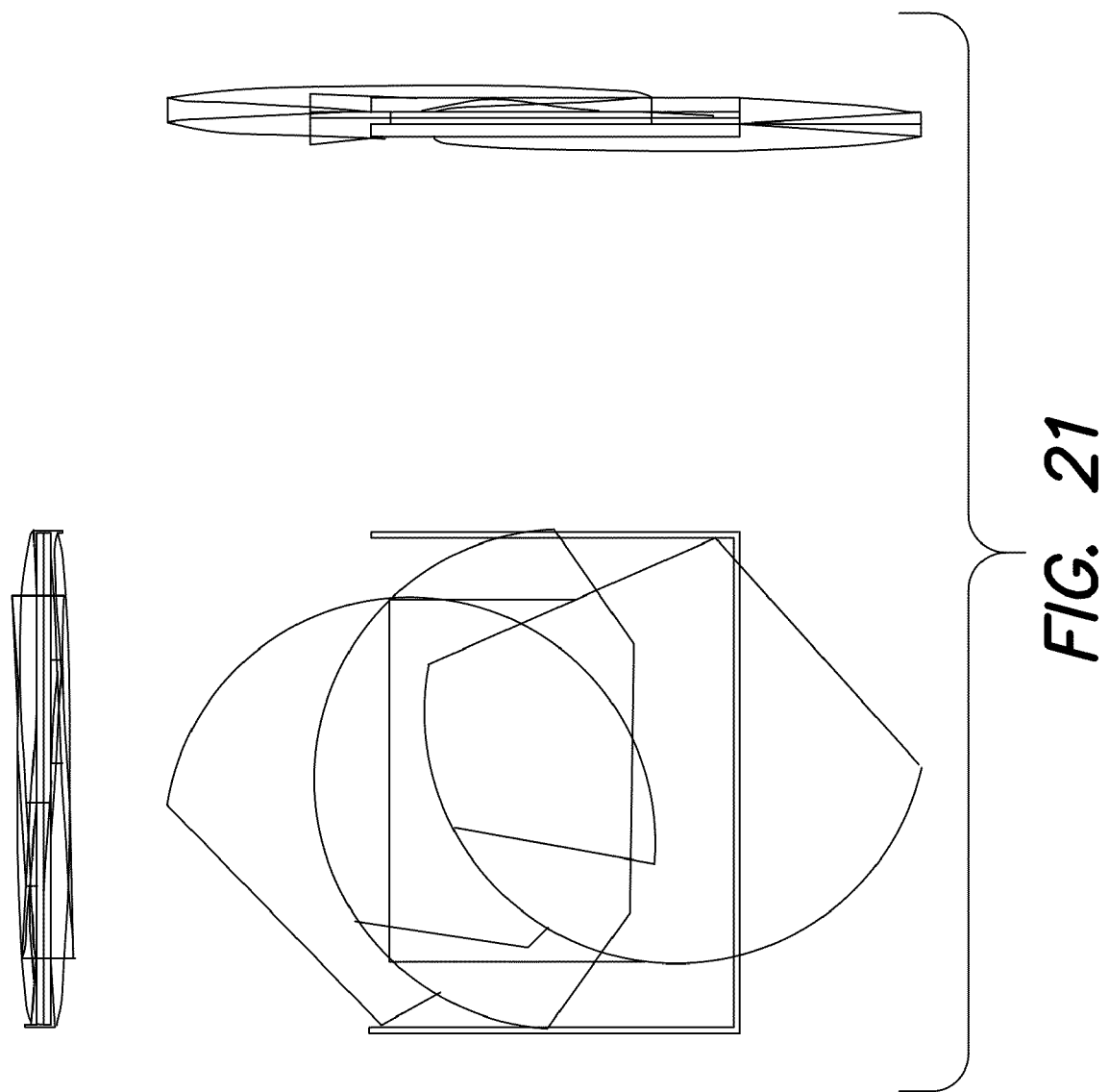
Figure 22:
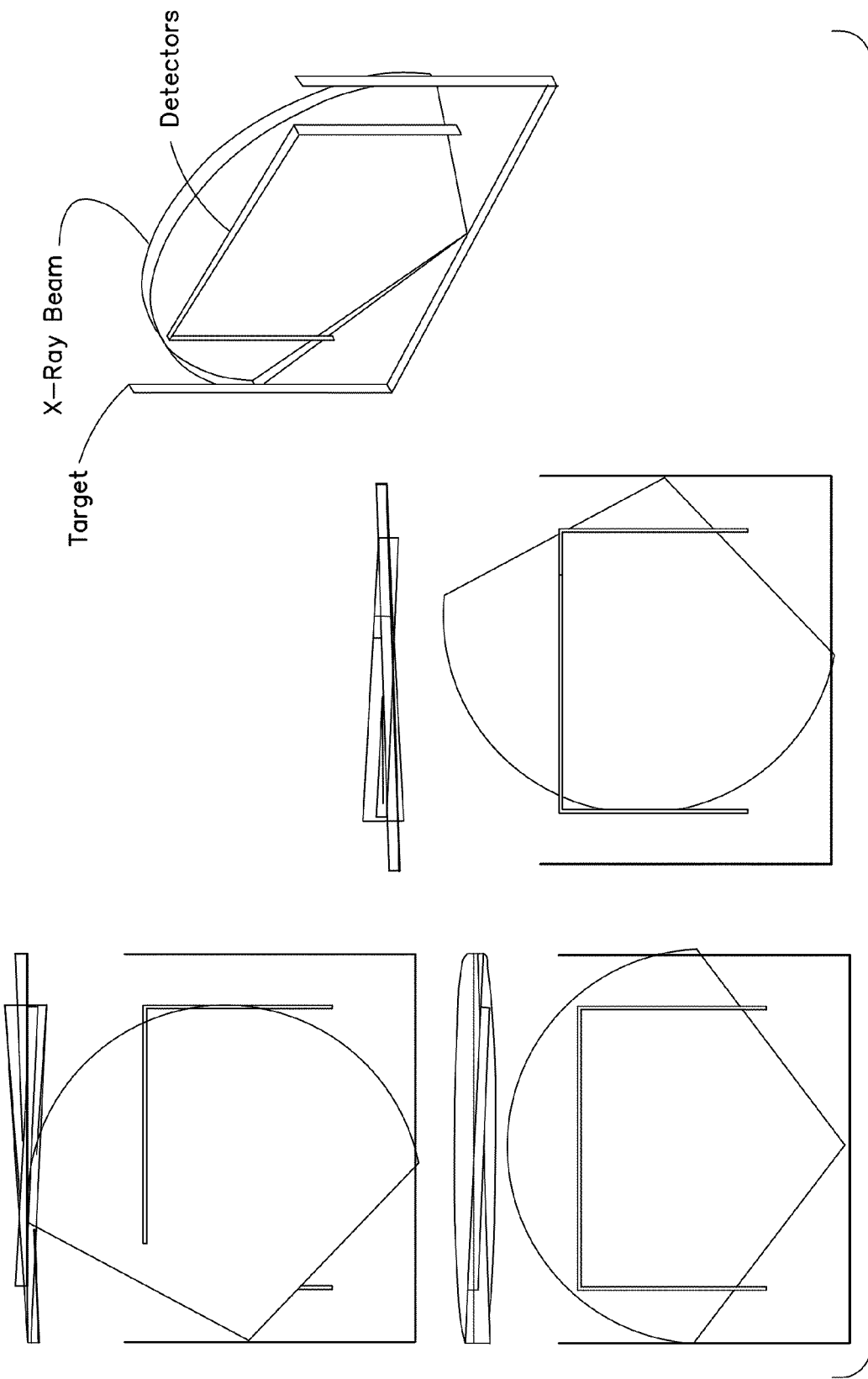

FIG. 14D illustrates another e-beam generator 1450*b* arranged to provide an e-beam to impinge on another portion of target 1410. E-beam generator may be arranged to mirror e-beam generator 1450*a* as shown in the top view of a portion of an x-ray scanning device in FIG. 14C, which shows the arrangement of both e-beam generators. FIG. 14E illustrates how the two e-beam generators 1450*a* and 1450*b* (behind tunnel 1470) are positioned with respect to a tunnel 1470 through which objects of interest are conveyed. As shown, each of e-beam generators 1450*a* and 1450*b* are positioned to provide e-beam energy to impinge on approximately half of substantially U-shaped target 1410' to emit x-rays in an inspection region internal to the tunnel 1470.

As discussed above, targets of any arbitrary geometry may be used. In FIG. 2, the various segments that form the target are provided continuously. However, in some embodiments, each of the segments is provided at an offset with respect to one another. For example, the linear segment 2012*a* may be provided at a first depth $z_0$, the circular segment 2014*a* may be provided at a second depth $z_1$, the linear segment 2012*b* may be provided at a third depth $z_2$, the circular segment 2014*b* may be provided at a fourth depth $z_3$, and the linear segment 2012*c* may be provided at a fifth depth $z_4$, wherein the depths $z_i$ increase in the direction of an item being conveyed through the generation subsystem. Any one or combination of segments may be offset from the other segments. Likewise, any one or combination of the segments of the detector array may be staggered in the direction of conveyance, or otherwise staggered or offset, as the aspects of the invention are limited in this respect.

Figure 3:
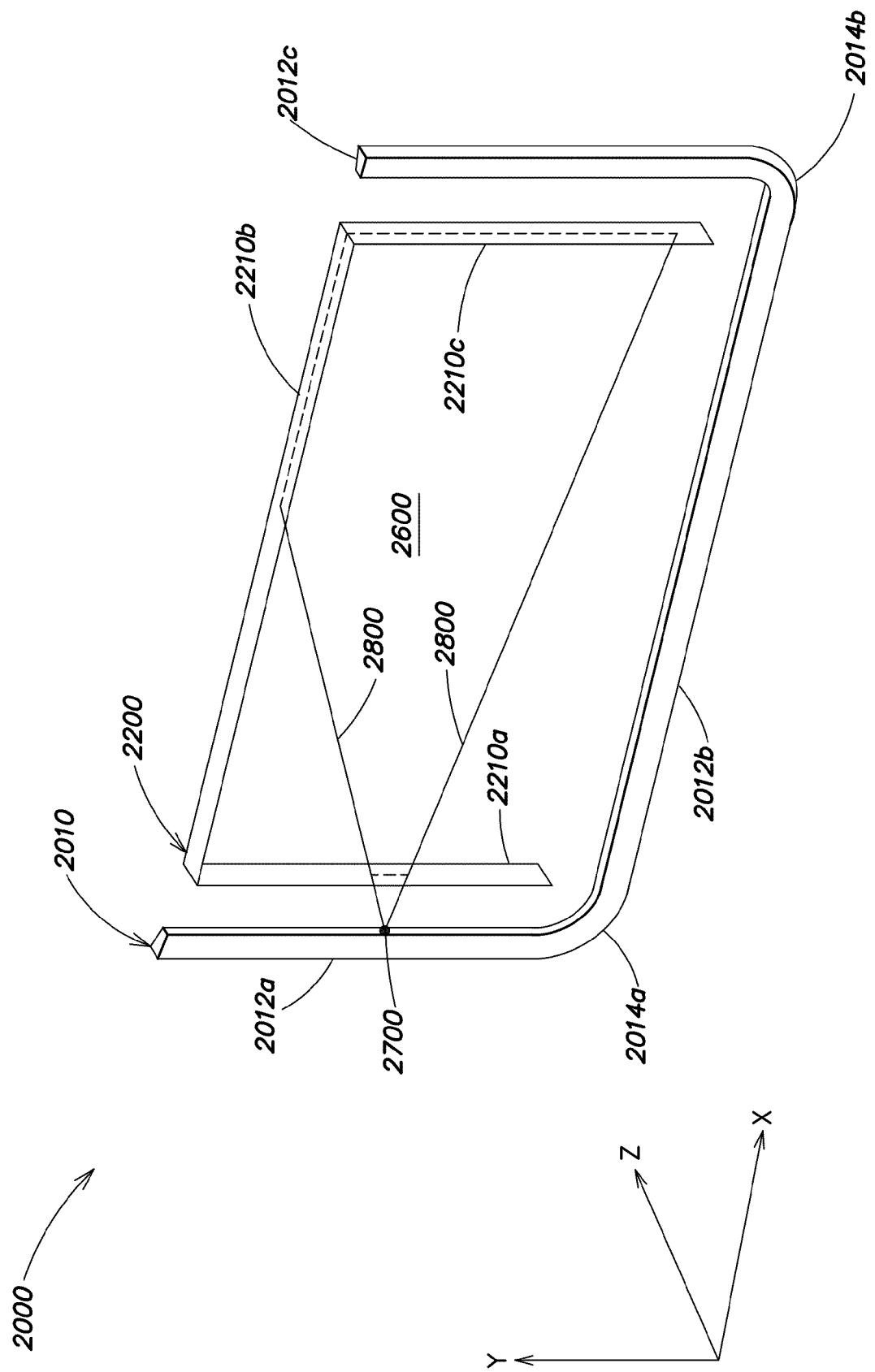
FIG. 3 illustrates near-side detector irradiation occurring in the arbitrary geometry target and detector array of FIG. 2.

Referencing FIG. 3 (illustrating substantially the same system as FIG. 2), to scan an object positioned in examination region 2600, an e-beam is directed to impinge on target 2010, which responds by emitting X-rays in the 4π directions. The emitted X-rays are then typically shaped by a desired configuration of one or more collimators to form a fan beam, a pencil beam or other shaped beam that enters the inspection region to penetrate an object being scanned, and to subsequently impinge on the diametrically opposed detectors after exiting the object, thus recording information about the interaction of the X-ray beam with the object.

In FIG. 3, collimators (not shown) are arranged such that at each point along target emitted X-rays are absorbed except for a fan of X-rays substantially in a plane that is permitted to pass into the inspection region. The fan beam enters the inspection region 2600 and penetrates the object being scanned. The detectors in detector array 2200 respond to X-rays generated from a diametric portion of the target. For example, the detectors along aims 2210*b* and 2210*c* of the detector array 2200 detect X-rays in the fan beam generated along arm 2012*a* of the target, as illustrated by exemplary fan beam 2800 emitted by X-ray source location 2700. As a result, when the detector array is substantially aligned in the same plane as the target, fan beam 2800 passes through the near side of the detector array (e.g., arm 2210*a* of the detector array) before entering the inspection region and ultimately impinging on the portion of the detector array intended to record attenuation information (i.e., the far side detectors).

The unintentional irradiation of portions of a detector array (e.g., the detector highlighted with a dotted line along arm 2210*a*) may be undesirable for a number of reasons. In particular, the unintentional irradiation of near side detectors (i.e., detectors not substantially diametric to the fan beam, such as the detectors positioned on the near side of the inspection region with respect to the X-ray source) causes the near side detectors to respond. However, the X-rays impinging on the near side detectors do not carry information about the object being scanned because the X-rays have not penetrated the inspection region, and thus the object, before impinging on the near-side detectors. Accordingly, the near side detectors will be generating spurious detection signals.

In addition, the near side detectors will interact with the X-rays causing some changes to the X-rays before they enter the inspection region. As such, the X-rays impinging on the intended detectors (e.g., the far side or diametric detectors) will have been modified by subject matter other than the object being scanned. Stated differently, some of the changes in the X-rays do not carry information because they correspond to the near side detectors and not the object being scanned, and more importantly, the near-side detectors block a significant and substantial portion of the x-rays from entering the inspection region as the detectors are designed to intercept a majority of x-rays impinging on their surface.

Figure 4:
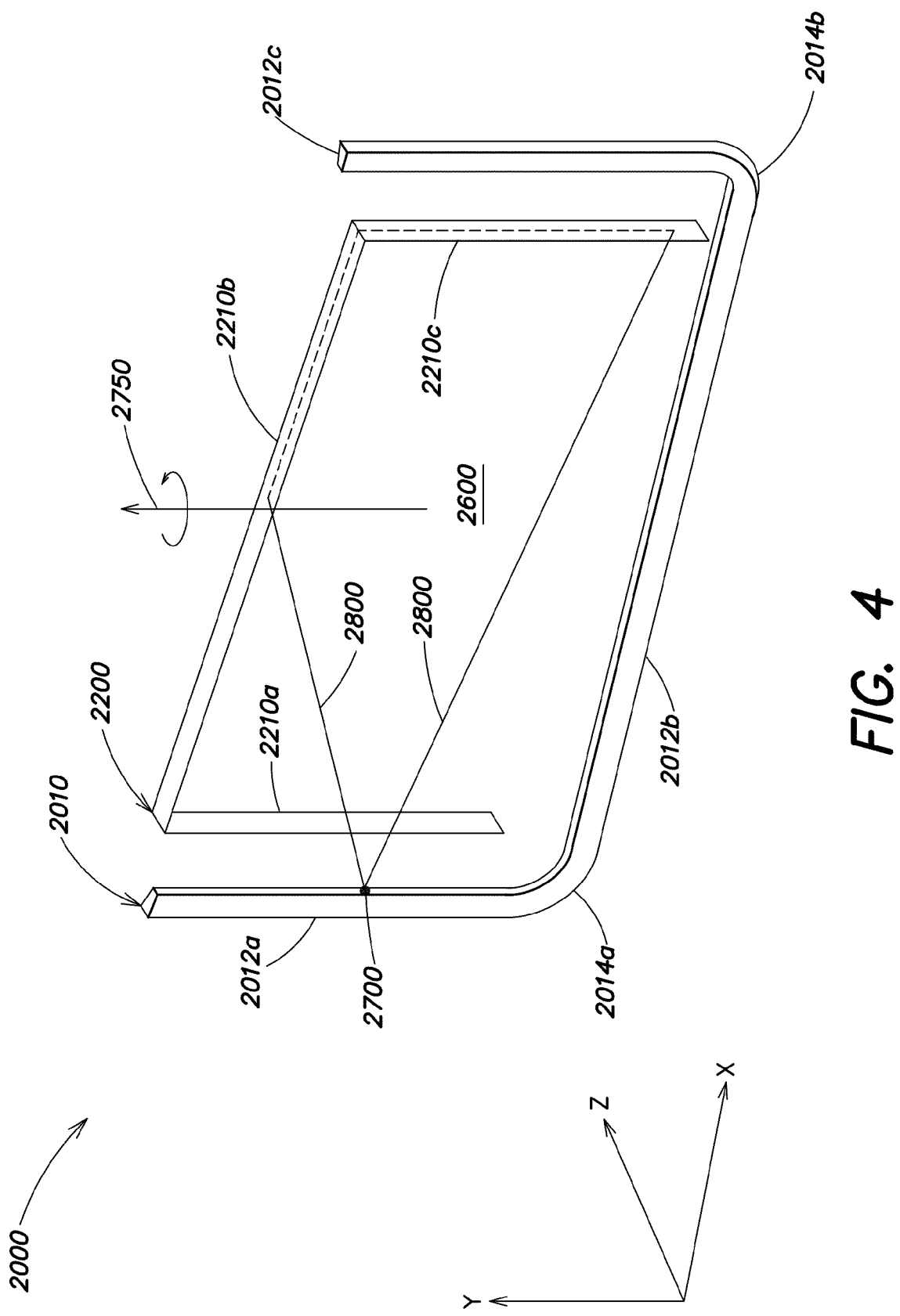
FIG. 4 illustrates an arbitrary geometry target and detector array configuration in which the target and detector array are rotated with respect to one another, in accordance with one embodiment of the present invention.

To prevent near-side detector irradiation, the plane of the detector array may be rotated with respect to the plane of the target. For example, in FIG. 4, detector array 2200 may be rotated about axis 2750. Accordingly, a fan beam emitted from locations along the target will avoid the near-side detectors, enter the inspection region and impinge on the far side detectors. For example, a fan beam generated from X-ray point of origin 2700 will pass by (and not through) detectors along portion 2210*a* of the array and impinge on detectors along portions 2210*b* and 2210*c* as intended. It should be appreciated that either the detector array or target may be rotated as long as the respective planes are positioned non-parallel to one another. In addition, other modifications may be used to effect an offset between the detector array and target planes to prevent near-side detector exposure.

It should be appreciated that the target generally surrounds, at least in part, a generally planar region. X-rays emitted from the target are generally collimated to permit only the x-rays substantially in this plane to enter an inspection region. Similarly, the detector array also surrounds, at least in part, a generally planar surface, for example, the plane comprising the vector normals of the detector surfaces of the detector array. Thus, the planes formed by the target and detector arrays are the cross-sections of the inspection area through which objects to be inspected are moved and/or conveyed. As discussed above, by rotating these planes with respect to one another such that they are non-parallel and non-coplanar, near-side detector irradiation may be prevented. FIGS. 17-22 illustrate various configurations of providing non-coplanar target and detector arrays to avoid near-side detector penetration, in accordance with other embodiments of the present invention.

Figure 24A:
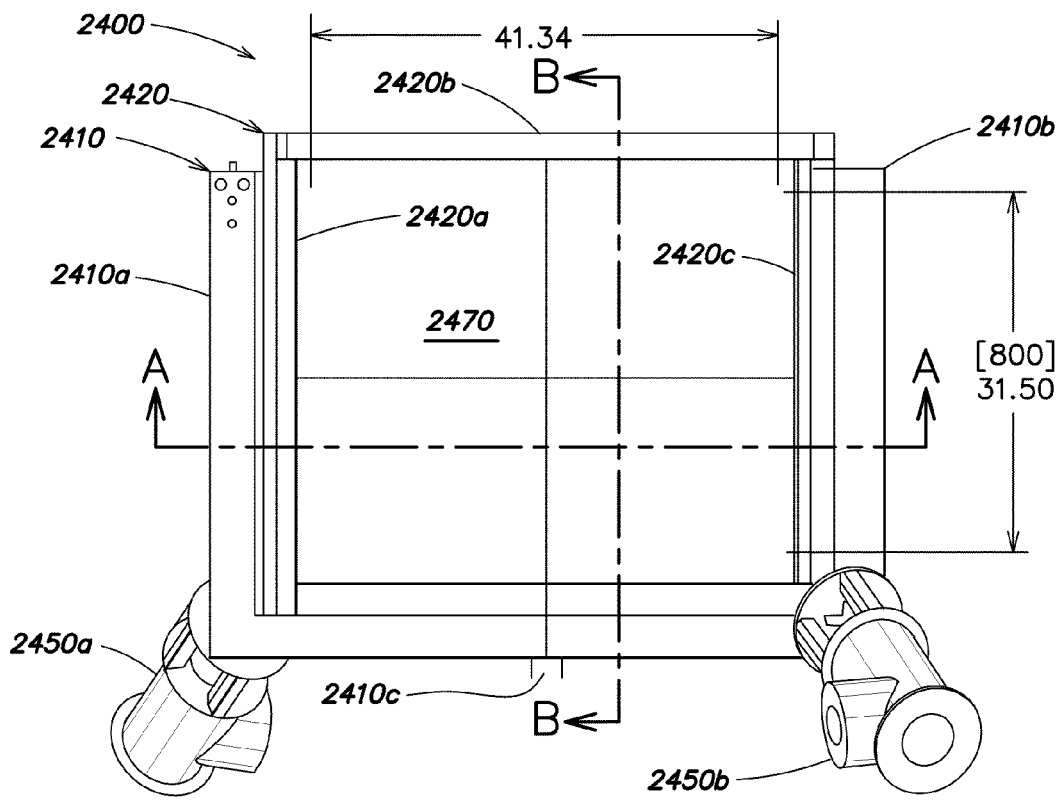
FIGS. 24-27 illustrate portions of an x-ray generation subsystem using dual and opposing electron beam generators, in accordance with various embodiments of the present invention.
Figure 24B:
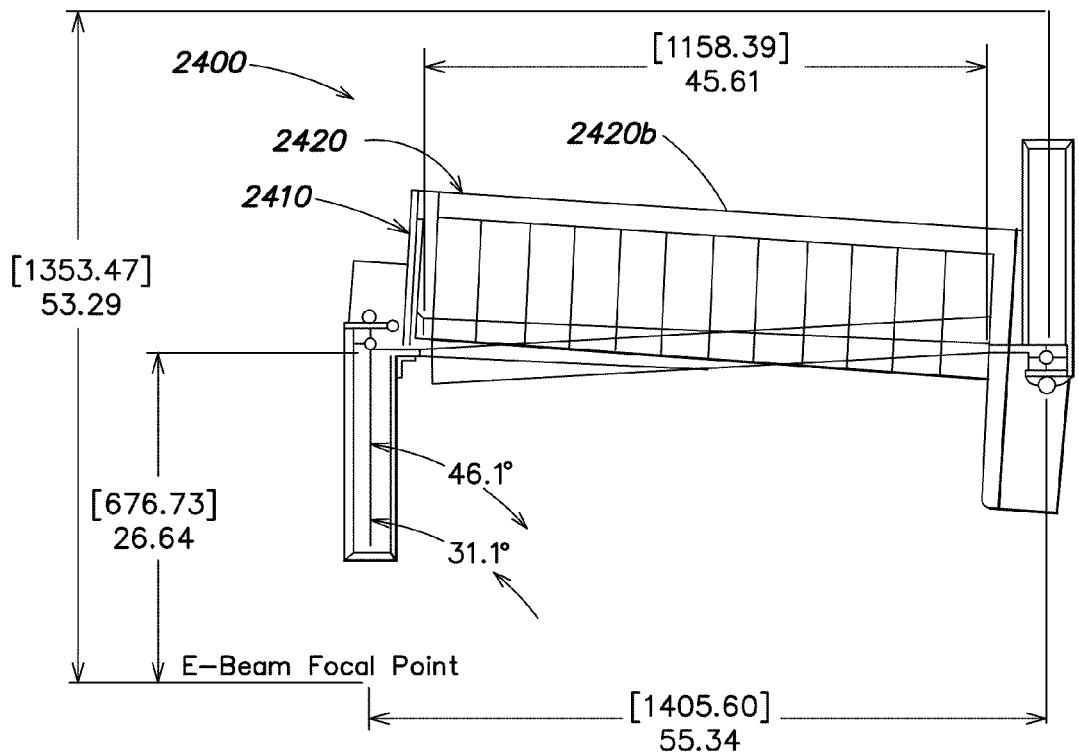

FIGS. 24A and 24B illustrate an X-ray generation subsystem employing two e-beam generators/guns arranged on opposite sides of the detector array. FIG. 24A illustrates the X-ray generation subsystem from a front view and FIG. 24B illustrates the X-ray generation subsystem from a top view. X-ray generation subsystem 2400 includes a generally rectangular shape detector array 2420 and generally rectangular shaped target 2410. The target and detector array have respective portions arranged diametrically such that X-rays emitted from the target impinge on the opposing portions of the detector array. The target and detector array form an inspection region 2470 though which objects to be inspected pass. That is, objects to be inspected pass through the planes formed by both the target and the detector array to be exposed to the X-rays emitted by the target.

A first e-beam generator 2450a is positioned on a first side of the detector array and generates an e-beam that is directed to impinge on L-shaped portion 2410a of target 2410. A second e-beam generator 2450b is positioned on a second side of the detector array and generates an e-beam that is directed to impinge on portion 2410b of target 2410. It should be appreciated that the e-beam generators or electron guns are arranged on opposite sides of the inspection region 2470. The plane formed by the target or the plane formed by the detector array may be viewed as dividing the X-ray generation device into the first side and the second side. Before an object enters the inspection region it is on the first side and, similarly, after the object has passed through the inspection regions it is on the second side.

In FIGS. 24A and 24B, the first e-beam generator is generally facing towards object passing through the inspection region. That is, the e-beam generated by e-beam generator 2450a, absent deflection forces, is emitted in a direction that generally opposes the direction of motion of the object. Similarly, e-beam generator 2450b is generally facing with the object passing through the inspection region (i.e., the e-beam generated by e-beam generator 2450a, absent deflection forces, is emitted in a direction that generally agrees with the direction of motion of the object. E-beam generators 2450a and 2450b may be tilted or angled such that the e-beam, absent deflection forces, is generated at any desired angle with respect to the direction of motion of the objects passing through the inspection region, as the aspects of the invention are not limited in this respect. Likewise, e-beam generators 2450a and 2450b may be positioned anywhere on the respective sides, or on the same side as illustrated in FIGS. 8-23, as the aspects of the invention are not limited for use with any particular configuration of e-beam generator(s).

Figure 24C:
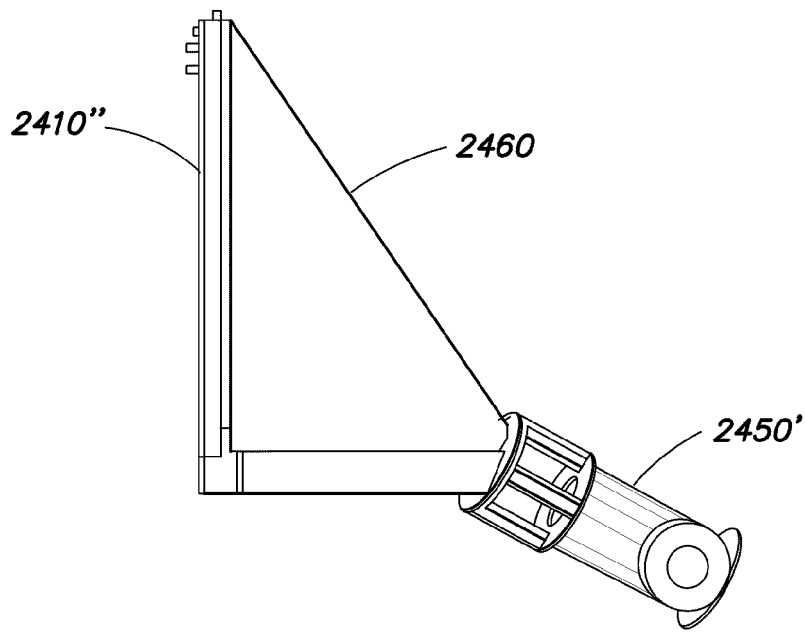
Figure 24D:
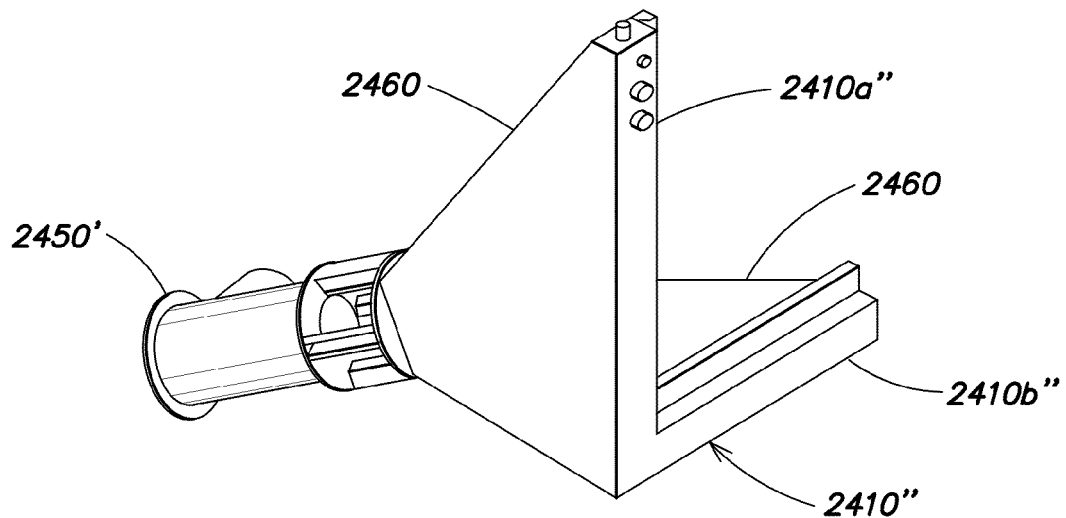

FIGS. 24C and D are opposing side views of a generator 2450', of the type that may be used in construction of an x-ray generation subsystem as depicted in FIGS. 24A and 24B.

The operation of the e-beam generators 2450a and 2450b may be timed such that they scan respective portions of the target in succession. For example, e-beam generator 2450a may be energized such that portion 2410a of target 2410 is impinged along a scanning path from the top of L-shaped portion 2410a to the bottom where portion 2410a meets portion 2410b. During this first interval, e-beam generator 2450b may be de-energized such that no e-beam energy impinges on portion 2410b. When e-beam generator 2450a reaches the end of its respective portion of the target, generator 2450a may be turned off and generator 2450b may be energized to scan portion 2410b. Generator 2410b may be arranged such that the e-beam emitted from the generator impinges on the portion 2410b at the bottom side where the two portions meet at the beginning of the interval and scans up the target to the top of the L-shaped portion.

In this way, the targets are independently scanned during subsequent intervals. It should be appreciated that there may be an overlap region 2410c where both e-beam generators direct e-beams to impinge on the overlap region of the target, as discussed above in connection with FIGS. 2-4. Overlap region 2410c is shown in FIG. 24 schematically and, when present, may be of any size or located anywhere on the target. It should be appreciated that the target need not include an overlap region, as aspects of the invention are not limited in this respect. The e-beam generators may be controlled to scan their respective targets at a constant velocity or at a variable scanning rate, as discussed in further detail below.

Figure 25A:
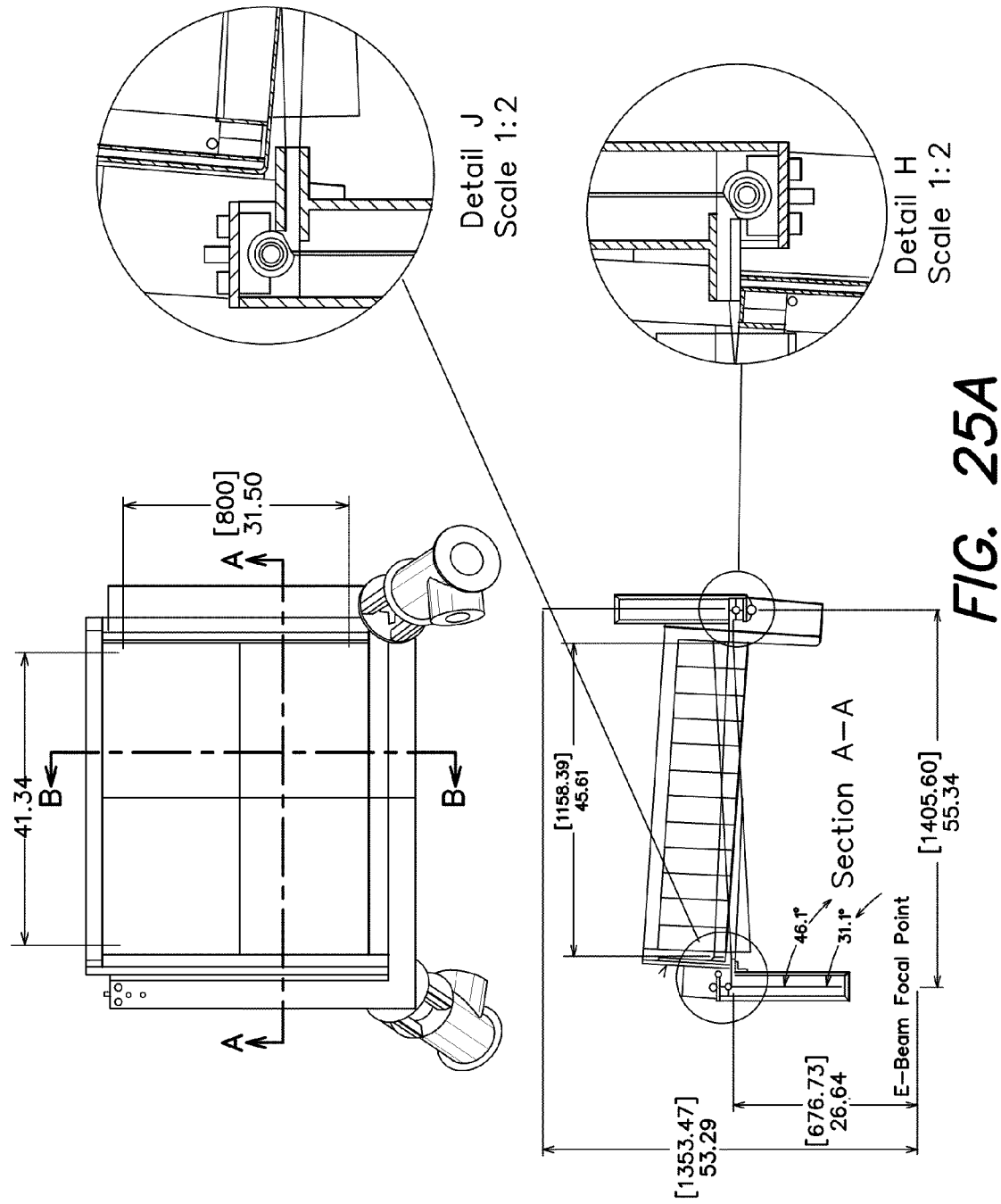
Figure 25B:
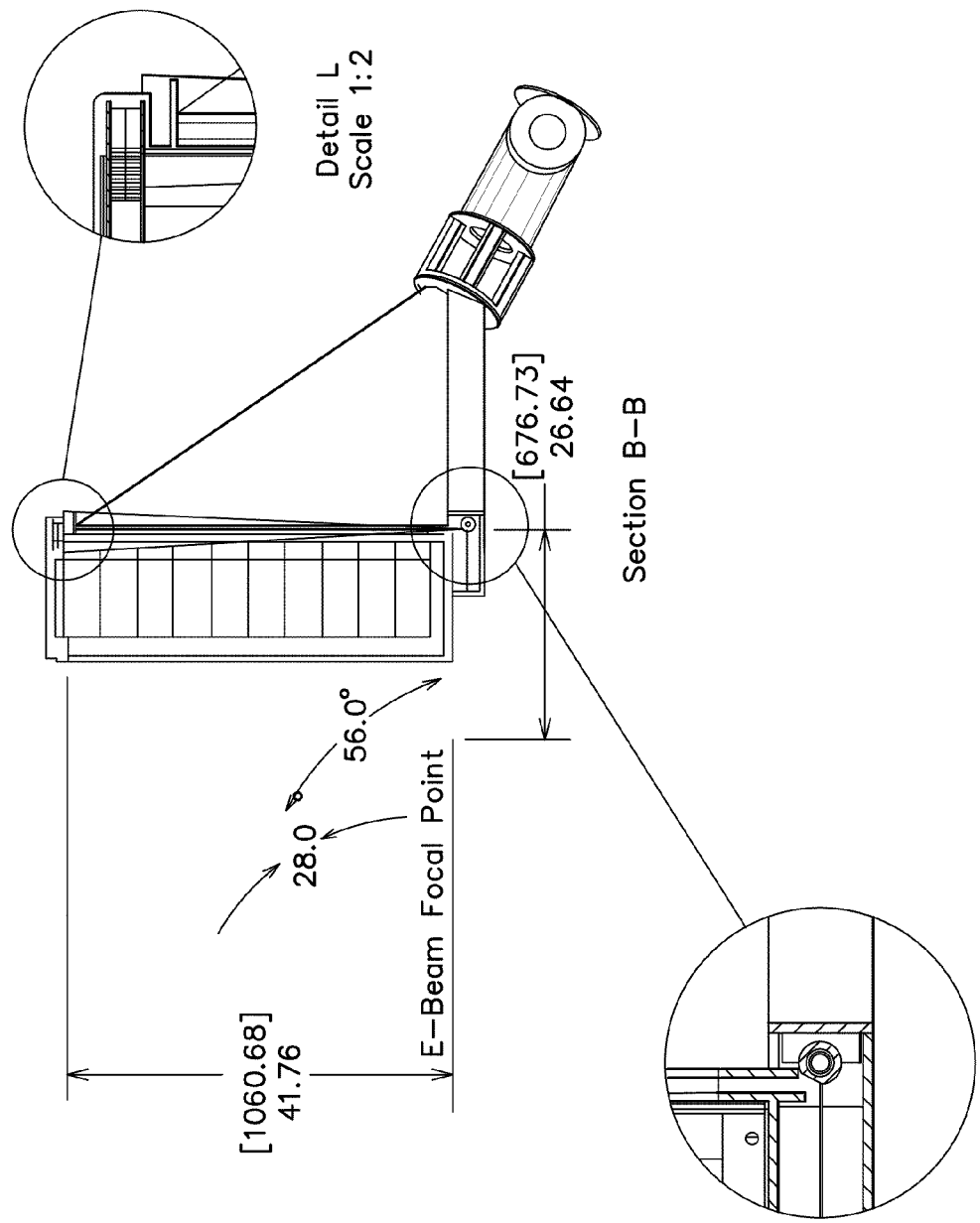
Figure 26A:
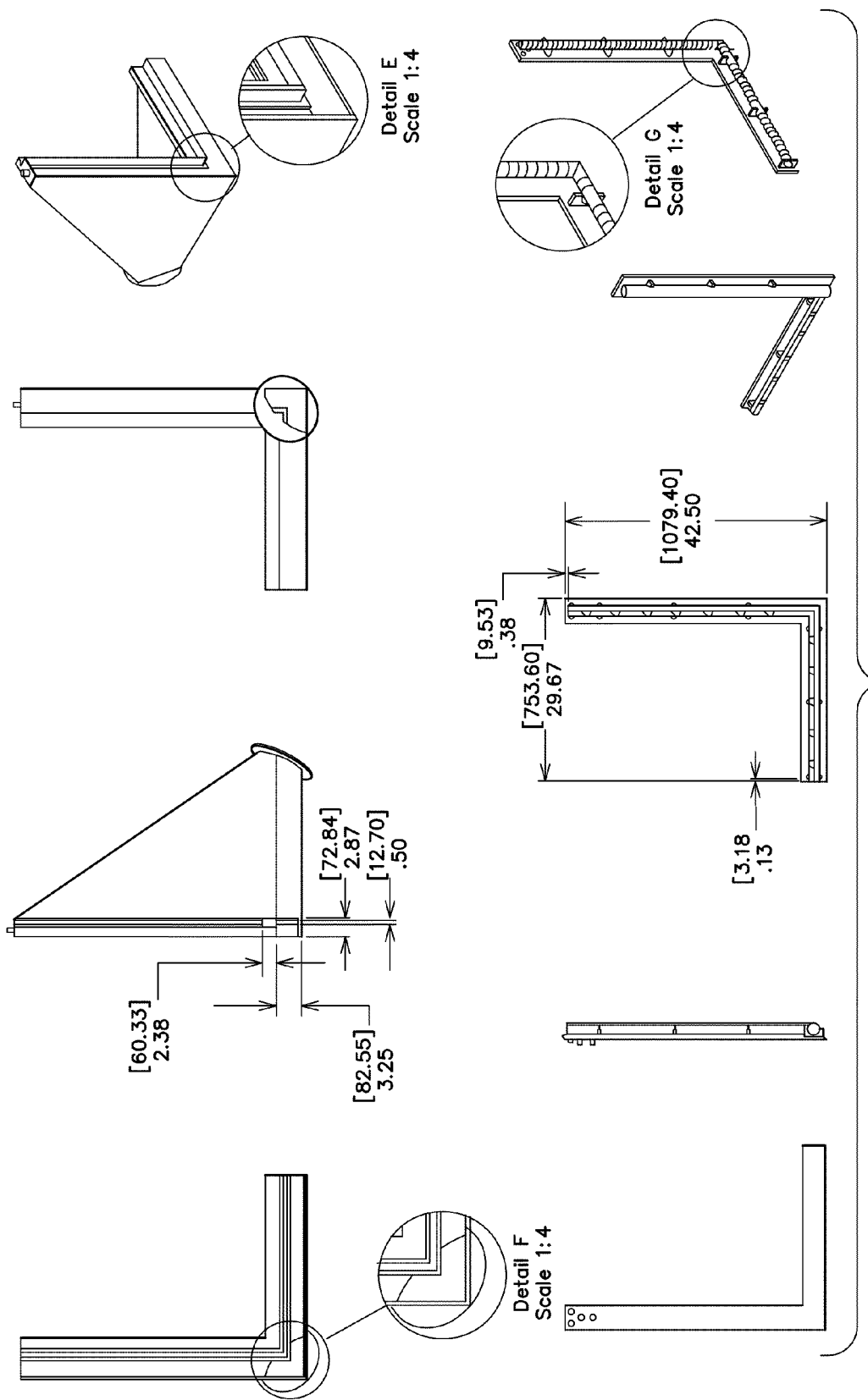
Figure 26B:
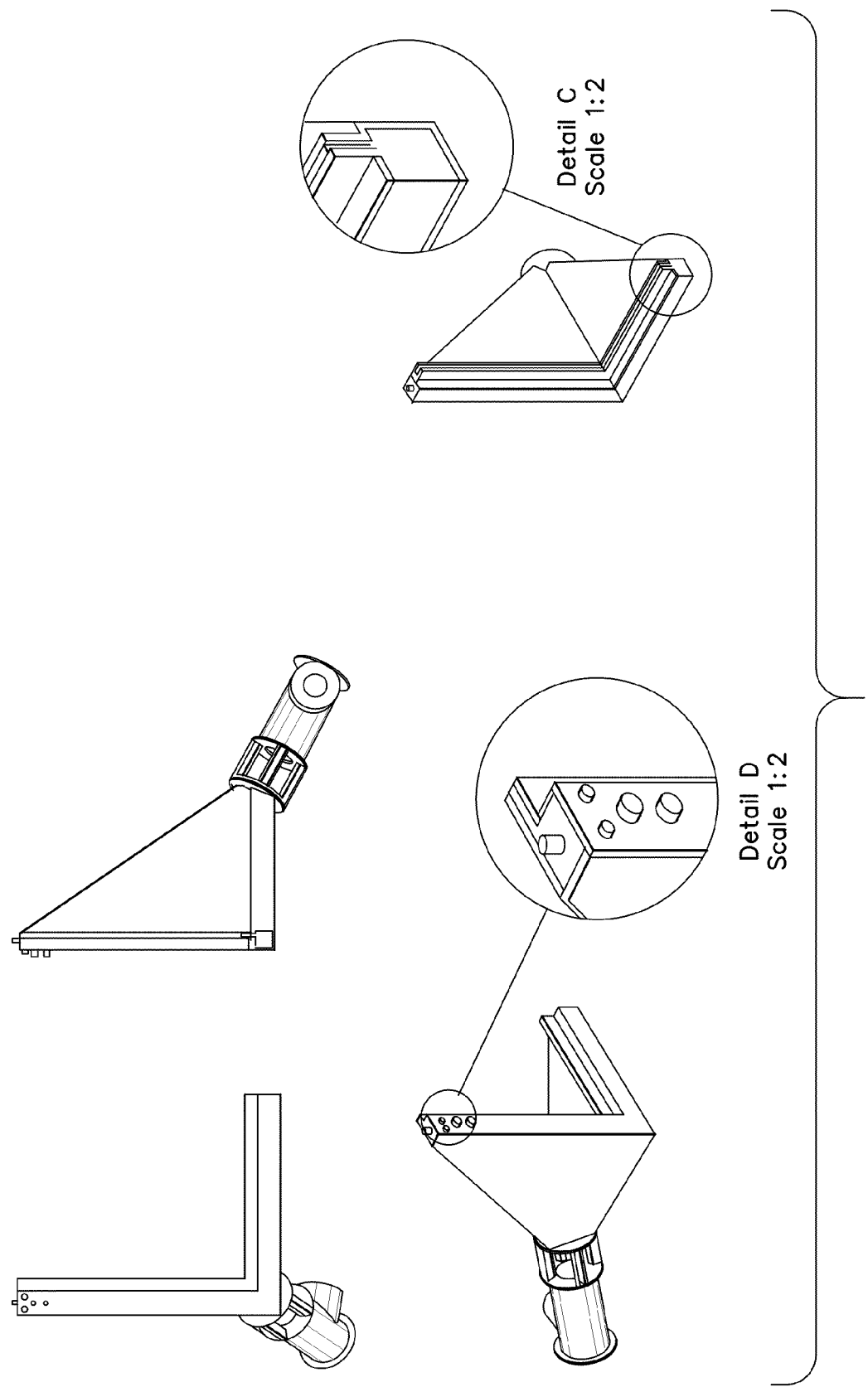

FIGS. 25-27 illustrate various views and details of the X-ray generation subsystem illustrated in FIG. 24. In particular, FIG. 25A illustrates the front and top views illustrated in FIGS. 24A and 24B, respectively. In addition, FIG. 25B illustrates a side view along section B-B. Various implementation details according to one embodiment of the x-ray generation subsystem in FIGS. 24A . . . D are illustrated in the circular magnifications; however, these details place no limitations on the aspects of the invention. FIGS. 26A and 26B illustrate various exemplary construction details of an e-beam generator with respect to an L-shaped portion of a target for which it is arranged to provide an e-beam. FIG. 26A illustrates construction details of the L-shaped portion of the e-beam a generator. FIG. 26B illustrates construction details of ends of the L-shaped portion. It should be appreciated that these exemplary details are not critical to the invention.

Figure 27A:
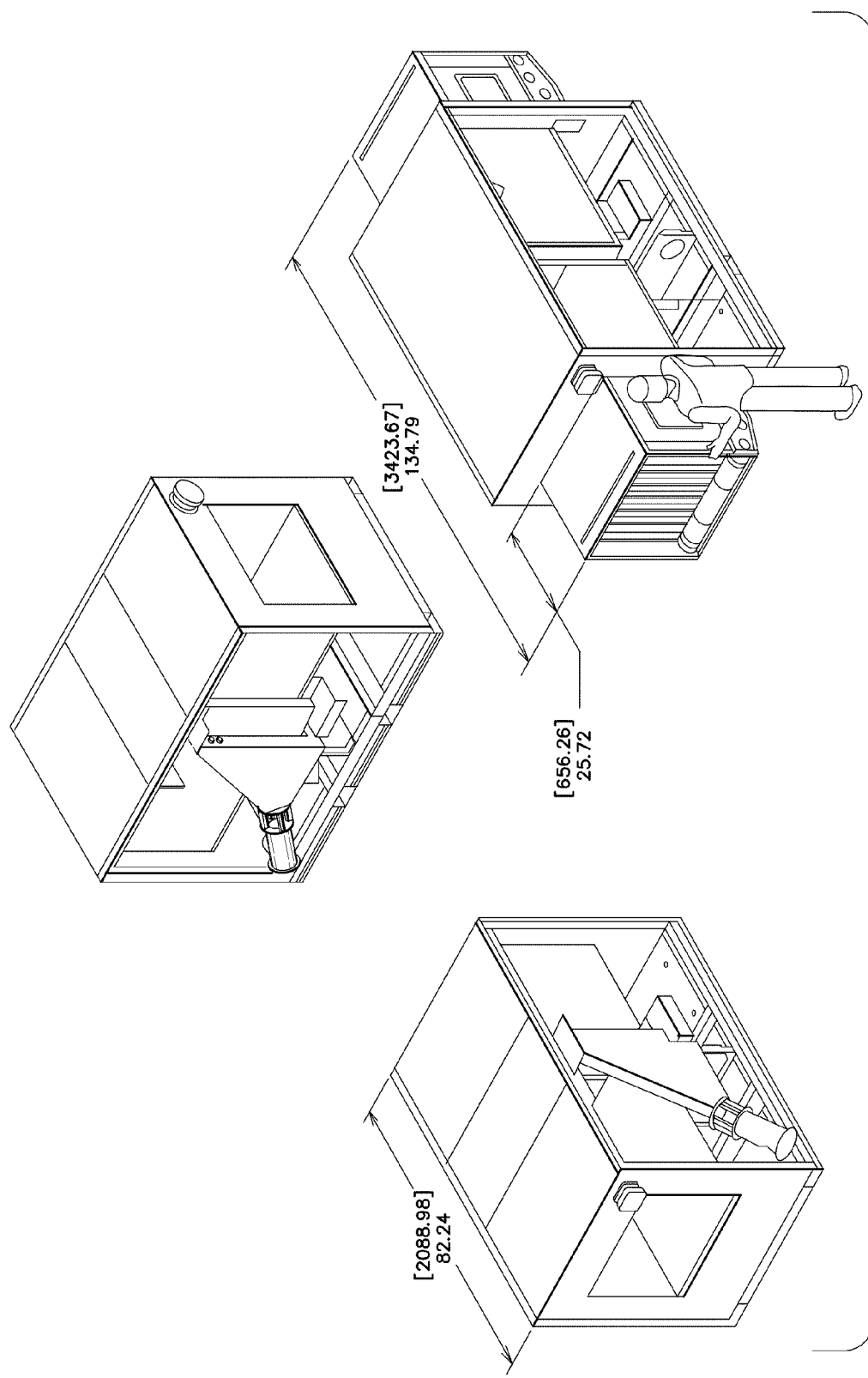
Figure 27B:
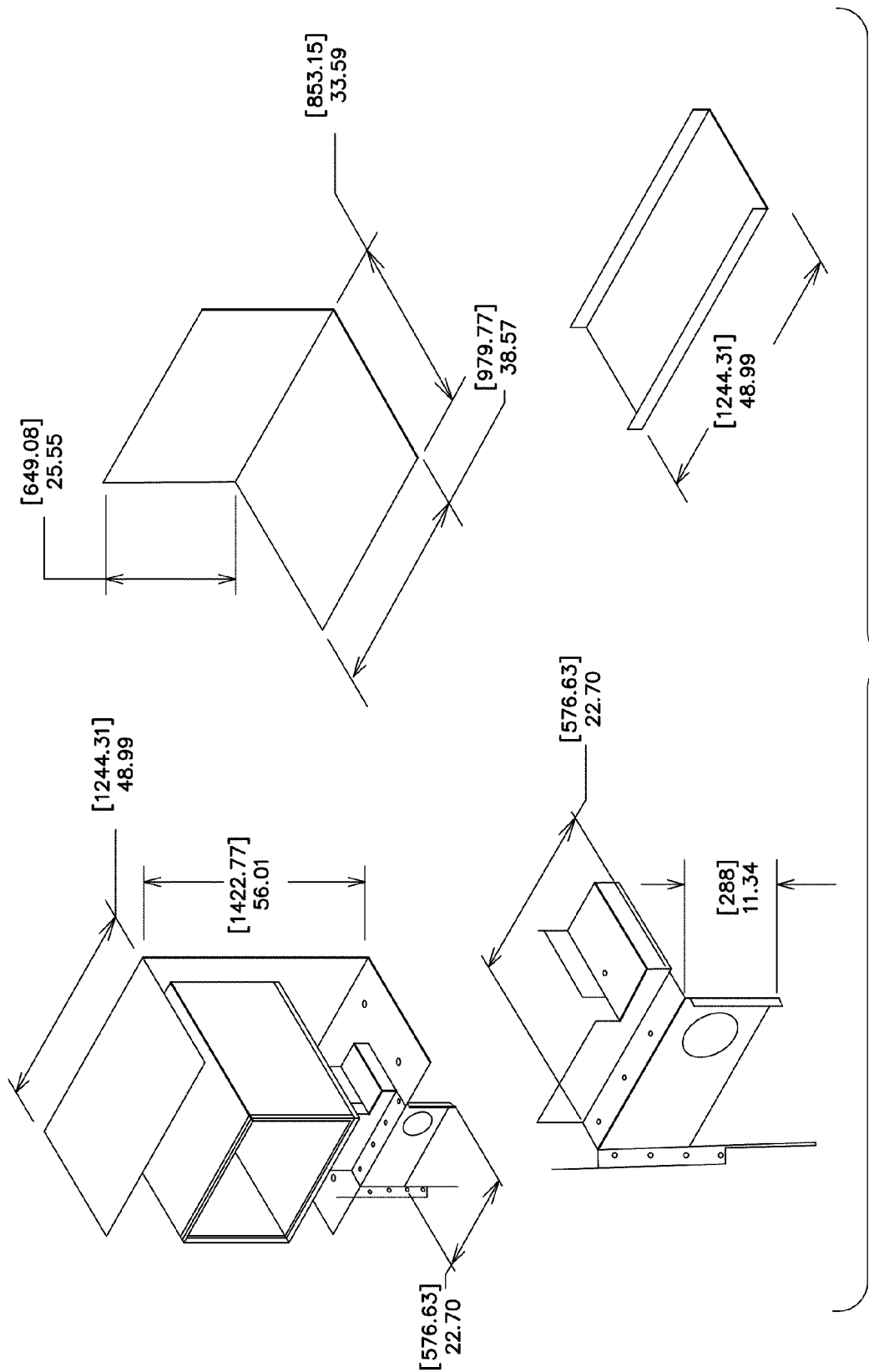

FIGS. 27A and 27B illustrate one embodiment of how the various components illustrated in FIGS. 24-26 may be used to construct a x-ray scanning device adapted to inspect object of interest place on a conveyer mechanism that transports the object though a substantially enclosed housing. As can be seen in FIG. 27A, e-beam generators may be positioned adjacent a tunnel through the housing, FIG. 27B illustrates additional components that may be used in constructing such a scanning device. It should be appreciated that the various construction and implementation details in FIGS. 24-27 are merely exemplary. An x-ray scanning devices may be constructed in any way, as the aspects of the present invention are not limited to any particular type of construction, implementation or arrangement of parts.

It should be appreciated that the embodiments illustrated in FIGS. 24-27 utilize various aspects of asymmetric positioning of e-beam generators. In particular, the e-beam generators in FIG. 24 are arranged asymmetrically with respect to the portions of the targets for which they are respectively intended to scan. FIGS. 24C and 24D further illustrate the positioning of the e-beam generator with respect to the target. FIG. 24D illustrates that the e-beam generator 2450' positioned asymmetrically with respect to both arms of the L-shaped target 2410" portion for which it is configured to scan. In particular, e-beam generator 2450' is positioned asymmetrically with respect to arm 2410a' and arm 2410b'. As discussed above in connection with FIGS. 30-32, the asymmetric configuration facilitates more compact designs having reduced sweep angle requirements for the e-beam generators.

To energize an e-beam generator, a high voltage power supply may be used to generate the necessary current required by the e-beam generator. In embodiments having multiple e-beam generators, a single power supply may be shared by the multiple guns to reduce the cost and size of the X-ray generation subsystem. Applicant has recognized that when two e-beam generators are employed in succession, a shared power supply conventionally must transition from providing a relatively large current to providing no current to one gun, and must transition from providing no current to providing a relatively large current to the other gun in a relatively short amount of time.

For example, the power supply may have to transition from providing approximately 40 mA (approximately 6.4 kW of power, or a change of 500 volts) to 0 mA on one gun and from 0 mA to approximately 40 mA on the other gun in a span of approximately 120 μSec. That is, the power supply must be stepped down and stepped up in a very short time frame. This places an extreme dynamic load challenge on the high voltage power supply. In particular, not only is the high voltage supply required to charge and discharge substantially as a step function, but the current provided to the guns must settle out quickly to avoid impacting the quality of the x-rays produced that, in turn, may cause artifacts in the resulting x-ray images.

Applicant has appreciated that by simultaneously de-energizing one gun while energizing another, the power differential the power supply undergoes can be reduced and/or eliminated. For example, as the first gun approaches the end of the portion of the target for which it is adapted to provide an e-beam (e.g., portion 2410a in FIG. 24), the power supply may begin ramping down the current provided to the first gun. At the same time, the power supply may begin ramping up the current provided to the second gun. In this way, the power supply avoids having to handle the relatively large load changes resulting from relatively large and substantially instantaneous current changes.

Figure 28:
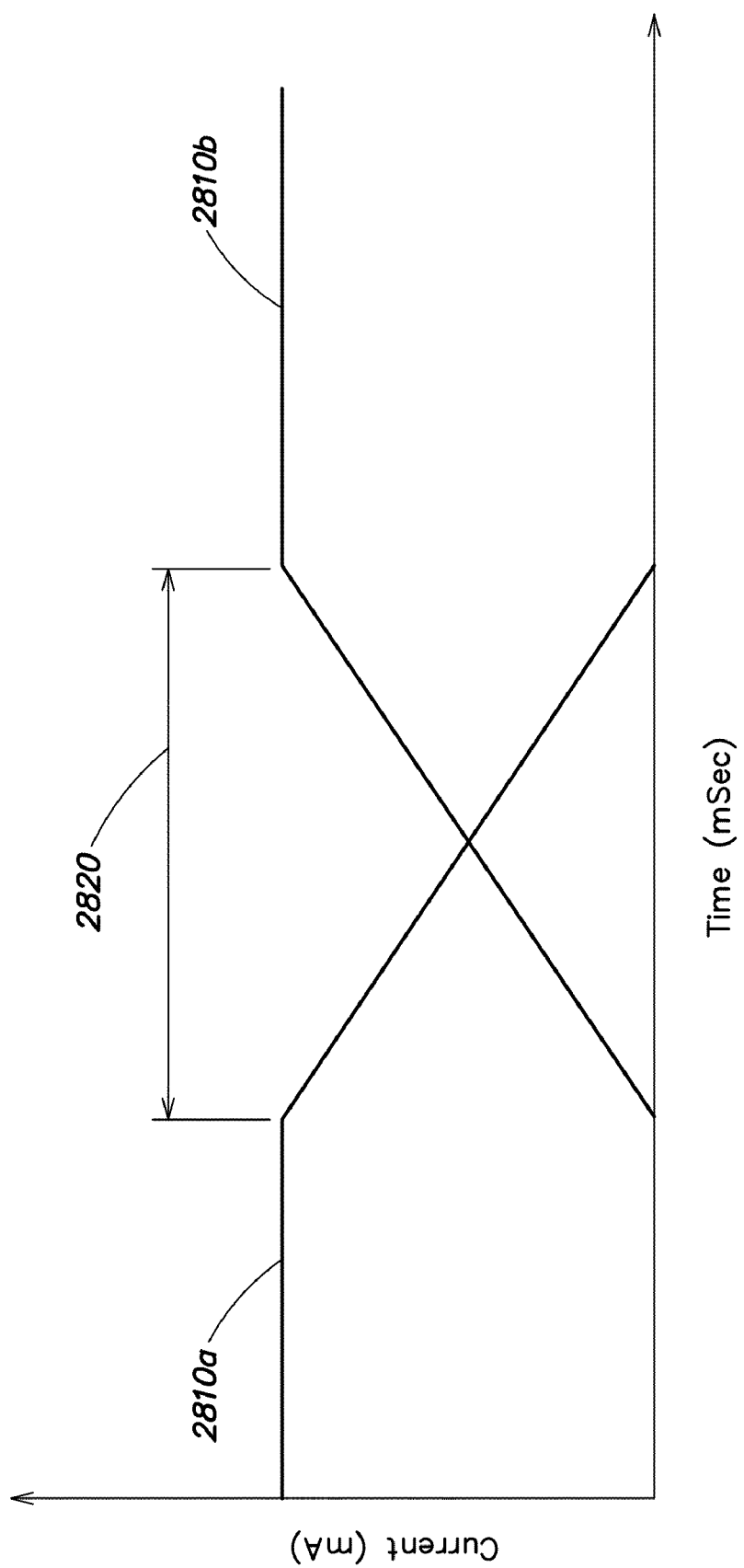
FIG. 28 illustrates a simultaneous energizing and de-energizing schedule for a power supply adapted to provide power to a pair of electron beam generators, in accordance with one embodiment of the present invention.

FIG. 28 illustrates a current transition performed by a high voltage power supply, in accordance with one embodiment of the present invention. The plot in FIG. 28 shows the current provided to a first gun by curve 2810a during an interval near the end of the scanning path of the first gun, and the current provided to a second gun by curve 2810b near the beginning of the scanning path of the second gun. The transition period 2820 shows the interval in which the first gun is de-energized and the second gun is energized.

As shown, the current provided to the first gun ramps down in a substantially linear fashion. Simultaneously, the current provided to the second gun ramps up according to the same substantially linear function. As a result of the simultaneous charge and discharge of the two guns, the sum of the currents provided remains the same. Accordingly, the load seen by the power supply does not change substantially and the power supply may be relieved of having to handle extreme dynamic changes in the load environment. Co-transitioning the energizing and de-energizing of the electron guns serves at least two beneficial purposes. First, the generally symmetric and simultaneously charging and discharging tend to cancel each other out to reduce or eliminate large net changes in current that the power supply must generate. Second, because large changes in current are not required, transients in the current generated by rapid transitions may be reduced and/or eliminated. Thus concerns over whether the waveform has settled may be substantially alleviated.

It should be appreciated that the current waveform illustrated in FIG. 28 are merely exemplary and schematic. For example, during the transition period, the currents need not be provided according to a linear waveform, as the currents may be transitioned according to other waveforms, such as an exponential transition, near linear transitions, or other curves suitable for transitioning the current in a substantially continuous fashion. Any simultaneous waveforms that reduce the dynamic load change on the power supply may be used, as the aspects of the invention are not limited in this respect.

In one embodiment, the transition interval during which one gun is energized and the other gun is de-energized occurs while the guns are providing respective e-beams in regions where no target exists such that no X-rays are generated during the transition interval. For example, there may be a gap in the target in a region where current is transitioned off for a first gun and on for a second gun. In this way, no X-ray energy is released during the transition and the detectors will register substantially little, if any, X-ray radiation. Other methods may be used to prevent X-rays from being generated during the transition period between energizing/de-energizing multiple guns in embodiments where multiple guns are present, as the aspects of the invention are not limited in this respect. For example, e-beam opaque material may be positioned between the electron gun and the detector array during transition periods.

As discussed above, the e-beam generators are relatively high power devices. For example, a power supply may be in the range of 70 kVolts to 200 kVolts and an e-beam generator may operate at approximately 6.4 kW of power or more. A substantial amount of this energy is dissipated in heat (largely at the impact point of the e-beam with the target), which, absent measures to disperse this heat, may cause damage to the equipment. Applicant has appreciated that by providing targets with a hollow core, cold water or some other coolant may be circulated through the target to dissipate excess heat. The liquid coolant absorbs heat and carries it out and away from the target and other sensitive components that may be damaged by high temperature resulting from heat dissipation of the energy in the e-beam generators.

In one embodiment, an x-ray detection system has a cooling system coupled to the target having at least one hollow portion. The cooling system may include a pump that circulates a liquid coolant through the at least one hollow portion. The liquid coolant may capture heat generate by the conversion of the e-beam energy to x-ray energy and neutralize and/or transport it away from the target and/or other sensitive components. The cooling system may be arranged any fashion, as the aspects of the invention are not limited for use with any particular type of cooling system.

An e-beam may be sequentially directed along a target to produce X-rays at varying angles about an object being scanned. By moving the point at which the e-beam impinges on the target, a number of views of the object at different angles may be obtained. The detector signals generated in response to impinging X-ray radiation over different viewing angles (e.g., over 180°) may be back-projected or otherwise processed to form a computer tomography (CT) image (or, in some cases, a laminographic image). That is, X-ray data represented as a function of detector location (t) (e.g., distance from the center of the reconstruction) and view angle θ, referred to as view data, may be transformed into image data representing, for example, density as a function of space.

Figure 5:
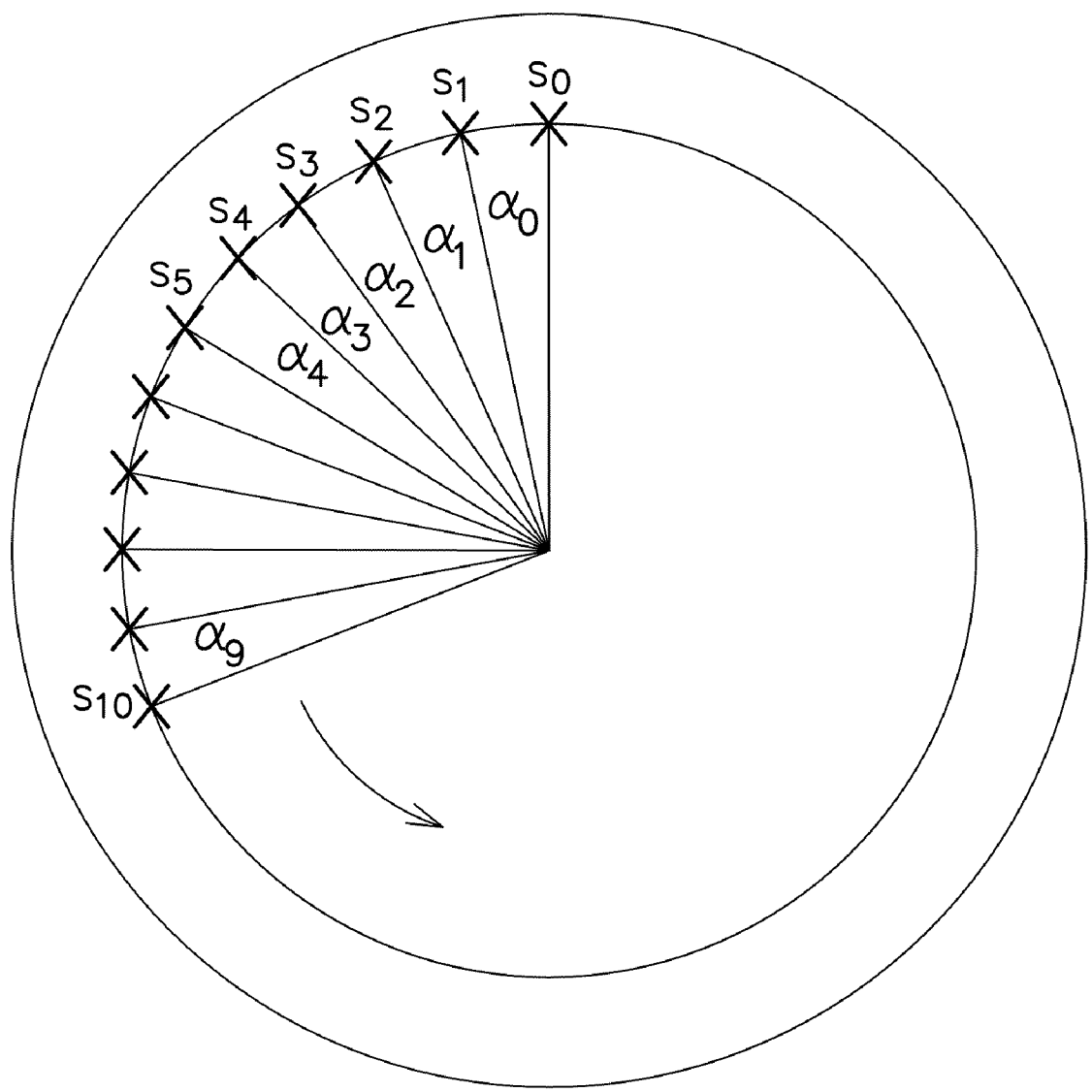
FIG. 5 illustrates equal penetration angles resulting from circular geometry systems.

The process of transforming view data into image data is referred to as image reconstruction and numerous methods of performing the transformation are known in the art. Back-projection, for example, is a well known image reconstruction algorithm. In back-projection, the view data in a (t, θ) coordinate frame is mapped into object or image space in a (x, y) coordinate frame. That is, each location in (x, y) space is assigned an intensity value based on attenuation information contained in the view data. As a general matter, image reconstruction is less complicated when the angle formed between successive locations at which the e-beam impinges on the target (i.e., successive X-ray source locations) and a center point of the inspection region are equidistant. For example, FIG. 5 illustrates a circular target of a conventional X-ray generation subsystem. In order to generate equal $\alpha_t$, the arc segments between each successive sample point $s_i$ (i.e., where the e-beam impinges on the target) may be made equal. To achieve this, conventional systems direct the e-beam along the circular scanning path at a constant velocity or uniform speed or scan rate, and sample detector outputs at the appropriate sampling rate.

Figure 6:
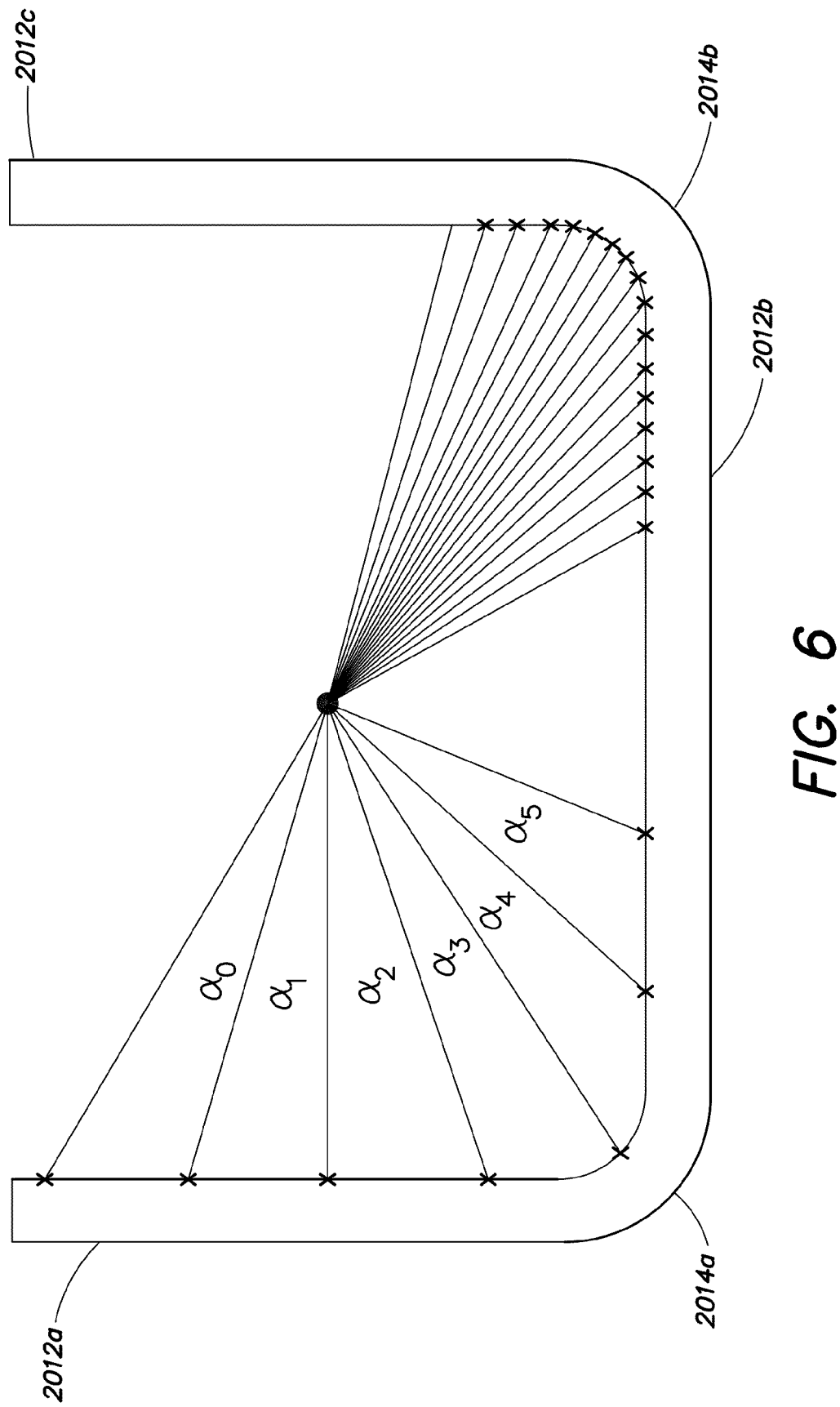
FIG. 6 illustrates unequal penetration angles that result in arbitrary geometry systems, in accordance with one embodiment of the present invention.

However, in arbitrary geometry generation subsystems, a constant scanning rate may not result in equidistant penetration angles with respect to a center location of the inspection region. FIG. 6 illustrates the generally U-shaped target of FIGS. 2-4. As shown, a constant scanning speed along the substantially linear arm 2012a will produce equidistant X-ray source locations, but will result in penetration angles that vary depending on where along the scanning path the e-beam is impinging. That is, a constant scan rate will produce variable angles $\alpha_i$ along the scan path. In FIG. 6, the target is sparsely sampled to highlight the differences in penetration angles. It should be appreciated that during operation, the samples will typically be closer together.

When scanning at locations along the circular arc segments of the target (e.g., circular arc segment 20), a constant velocity scan rate will impinge at locations that are not equidistant with respect to penetration angles generated along the linear segments, nor will the penetration angles be equidistant with respect to the linear segments, nor to each other as illustrated by the exemplary samples in the lower right quadrant of the target. The scan path is sampled differently in the low right quadrant to highlight the dissimilarities in penetration angles and sample distances that occur at the transitions between target segments of different geometries.

Accordingly, a constant or uniform scanning rate in non-circular geometries may make image reconstruction more complicated. Applicant has appreciated that scanning an e-beam along a scanning path of a non-circular geometry, wherein the scanning is performed at a non-constant and/or non-uniform velocity (i.e., a non-uniform scan rate), equidistant penetration angles may be produced. Any variable rate scanning path may be chosen, for example, the scan rate may be varied as a function of the location along the scanning path. In one embodiment, the scanning rate is varied along the scanning path such that penetration angles generated along the scanning path are approximately equal, thus simplifying image reconstruction computations. It should be appreciated that the scanning rate schedule may depend on the shape of the target. A target geometry of all linear segments may have a different scanning rate schedule than a detector geometry having a combination of linear and circular arc segments.

Figure 7:
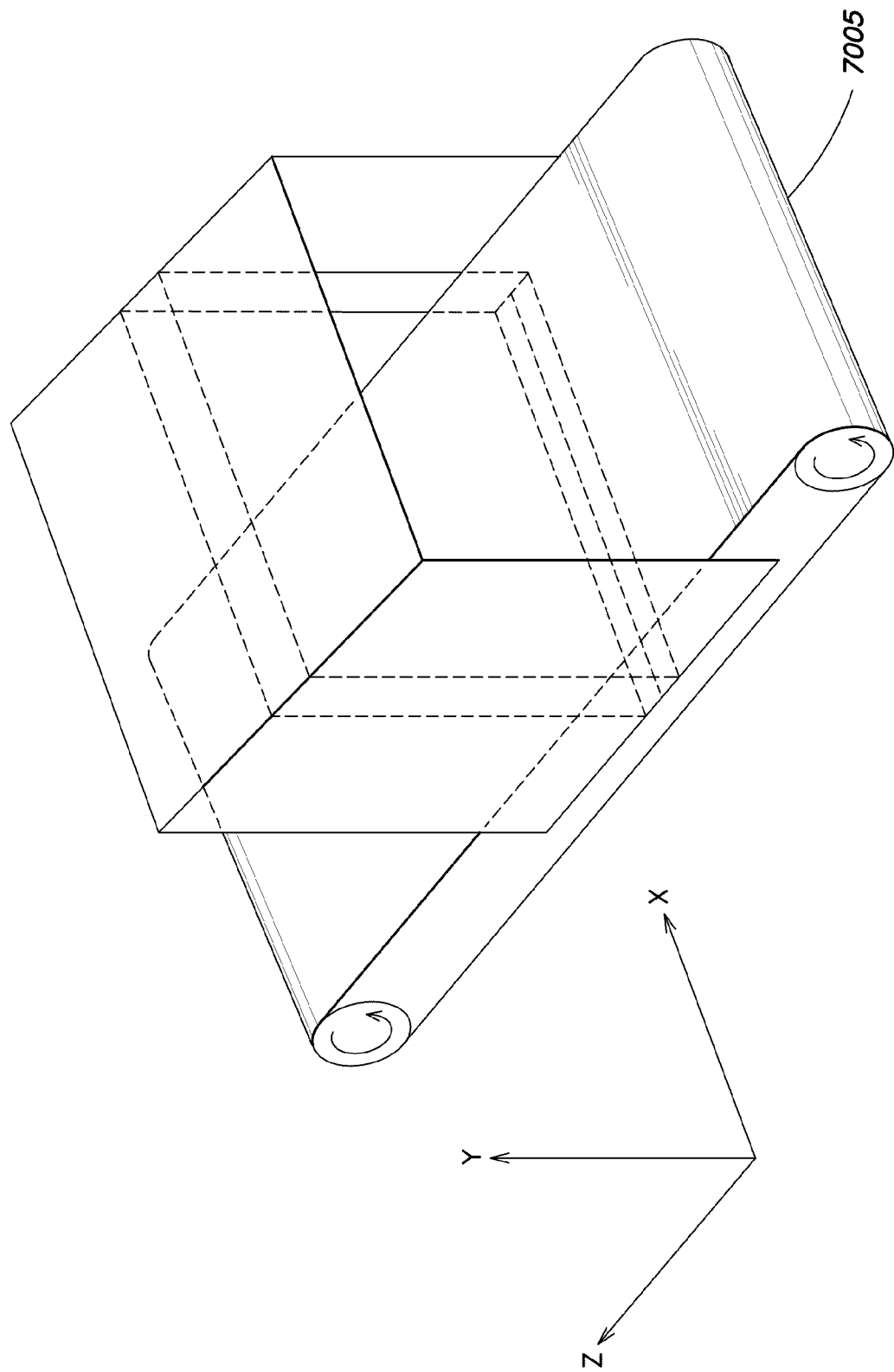
FIG. 7 illustrates an arbitrary geometry system with a conveyer system to convey objects through a covered tunnel, in accordance with one embodiment of the present invention.
Figure 8:
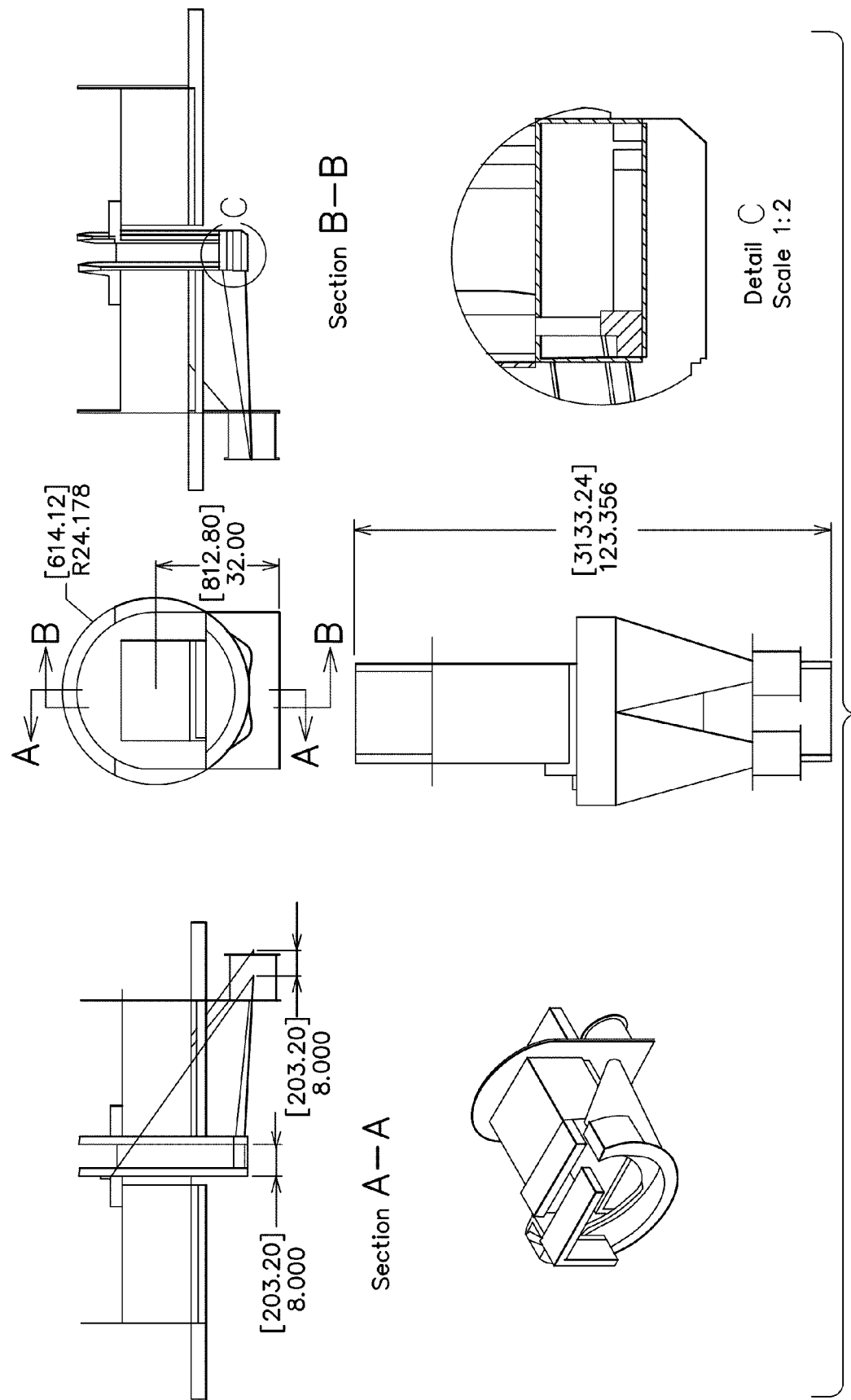
Figure 9:
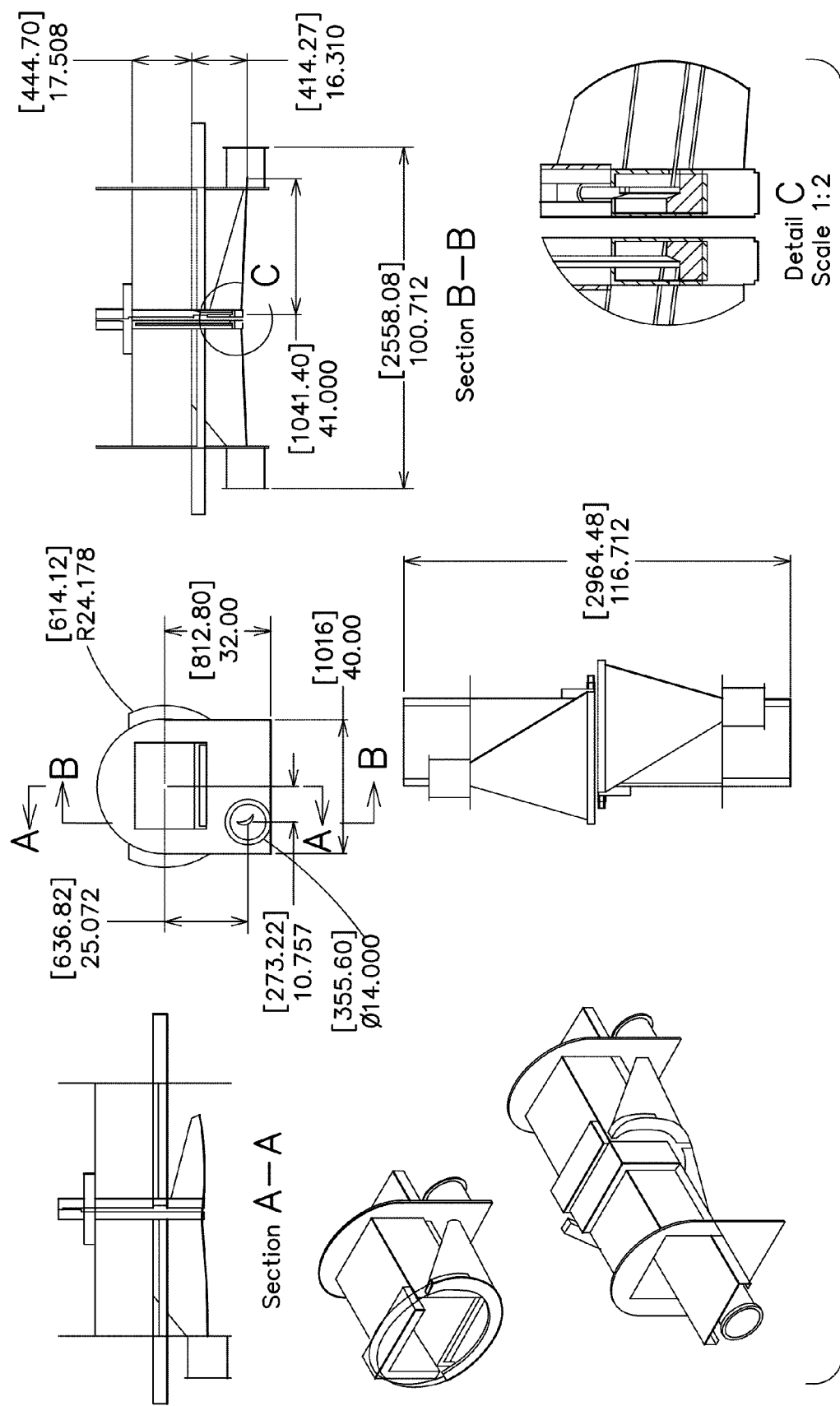
Figure 23:
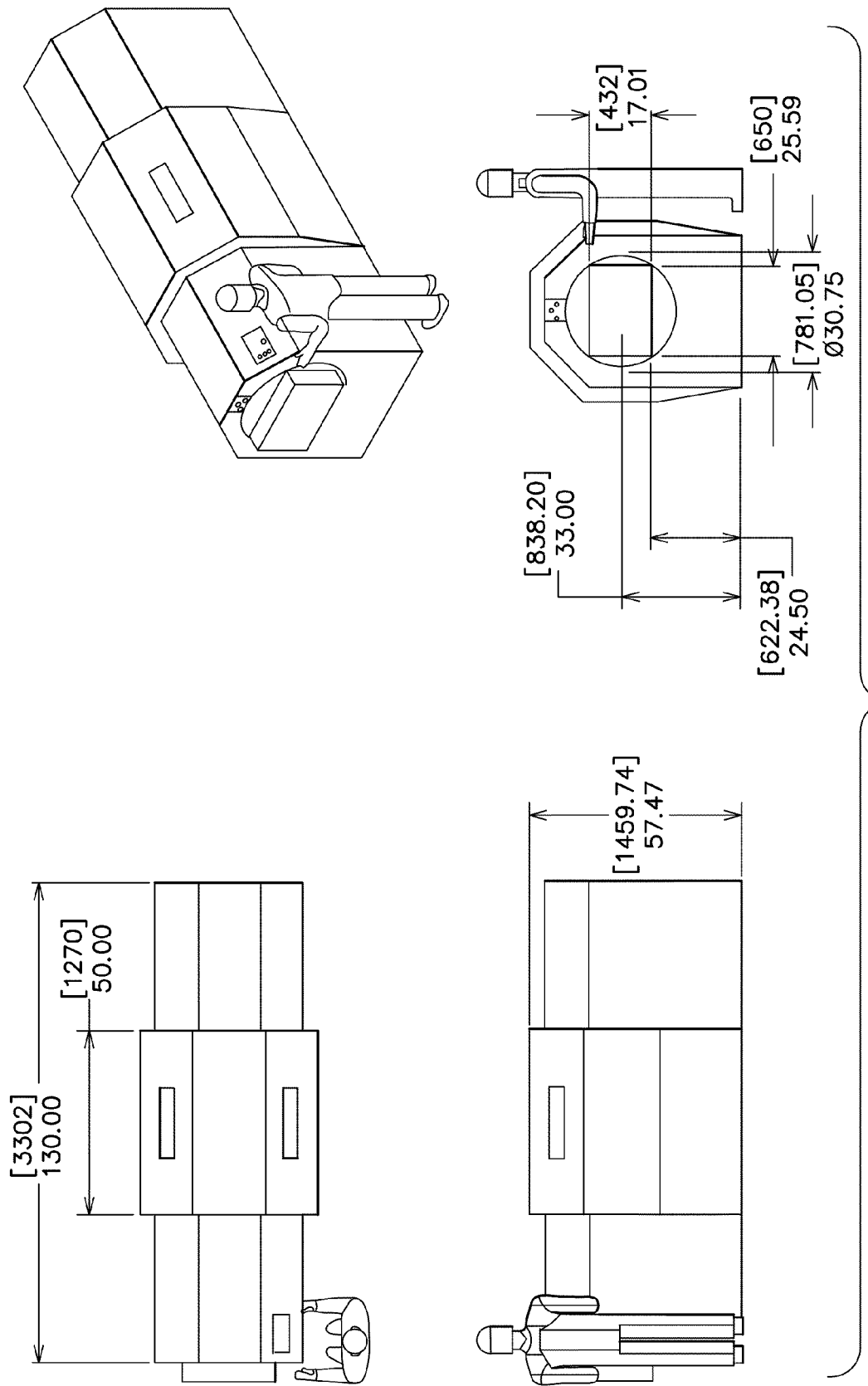

In many X-ray generation subsystems, such as X-ray detection systems adapted for scanning items such as articles of baggage, parcels, or other containers, where it is desired to perform an inspection of the item for prohibited material, the items being inspected may be conveyed through an inspection region on a conveyor. For example, FIG. 7 illustrates an X-ray detection system where items for inspection are carried through a detection area on a conveyor 7005 in a direction parallel to the z-axis. FIGS. 23 and 27 illustrate other embodiments of X-ray detection systems wherein items to be inspected are conveyed through a tunnel to be exposed to X-ray radiation. Synchronizing of the scan and the position of the conveyer facilitates pipelining the reconstruction into a regular grid of voxel dimensions.

It may be desirable to synchronize the scanning rate with the speed of the conveyor. In this way, as the e-beam traces along the scan path, the X-rays produced by the target will penetrate the object of interest at substantially the same cross-section. That is, X-rays penetrating the object at the various angles about the object will carry attenuation information about substantially the same plane through the object. In conventional circular geometry generation subsystems, by appropriately selecting the constant velocity by which the target is scanned, the scanning may be synchronized with the conveying apparatus. It should be appreciated that with the motion in the z-direction, the circular scanning path becomes a circular helix or corkscrew shape. The '271 patent incorporated above describes the conventional understanding of the criticality of a constant scan rate to synchronize multi-size scanning in circular geometry systems.

However, a constant scanning path along a non-circular scanning path frustrates synchronization with the scanning apparatus. Accordingly, Applicant has appreciated that providing a variable scanning rate in an arbitrary geometry (i.e., non-circular geometry) generation subsystem may facilitate synchronization with the conveyance system such that the X-rays generated from one traversal of the scanning path penetrates the object being scanned at substantially the same plane, slice or cross-section.

The schedule at which the scan rate is varied to synchronize the scanning with the conveying apparatus may depend on a given geometry of the target and whether the target is continuous or provided in discontinuous segments offset in the direction of conveyance. It should be appreciated that any desired scan rate schedule may be used, as the aspects of the invention are not limited in this respect. In addition, the scan rate schedule may be generated to produce equal penetration angles, to synchronize the system or both.

It should be appreciated that an X-ray generation subsystem may include more than one target and/or detector array. For example, in some embodiments, multiple detector arrays are disposed successively in the direction of motion of an item being inspected. One or more targets may be positioned to generate X-rays to impinge on the multiple detector arrays. In one embodiment, each detector array has a respective target positioned to generate X-rays to impinge on the detector array. Any configuration and combination of target and detector array may be used, as the aspects of the invention are not limited in this respect.

Figure 33:
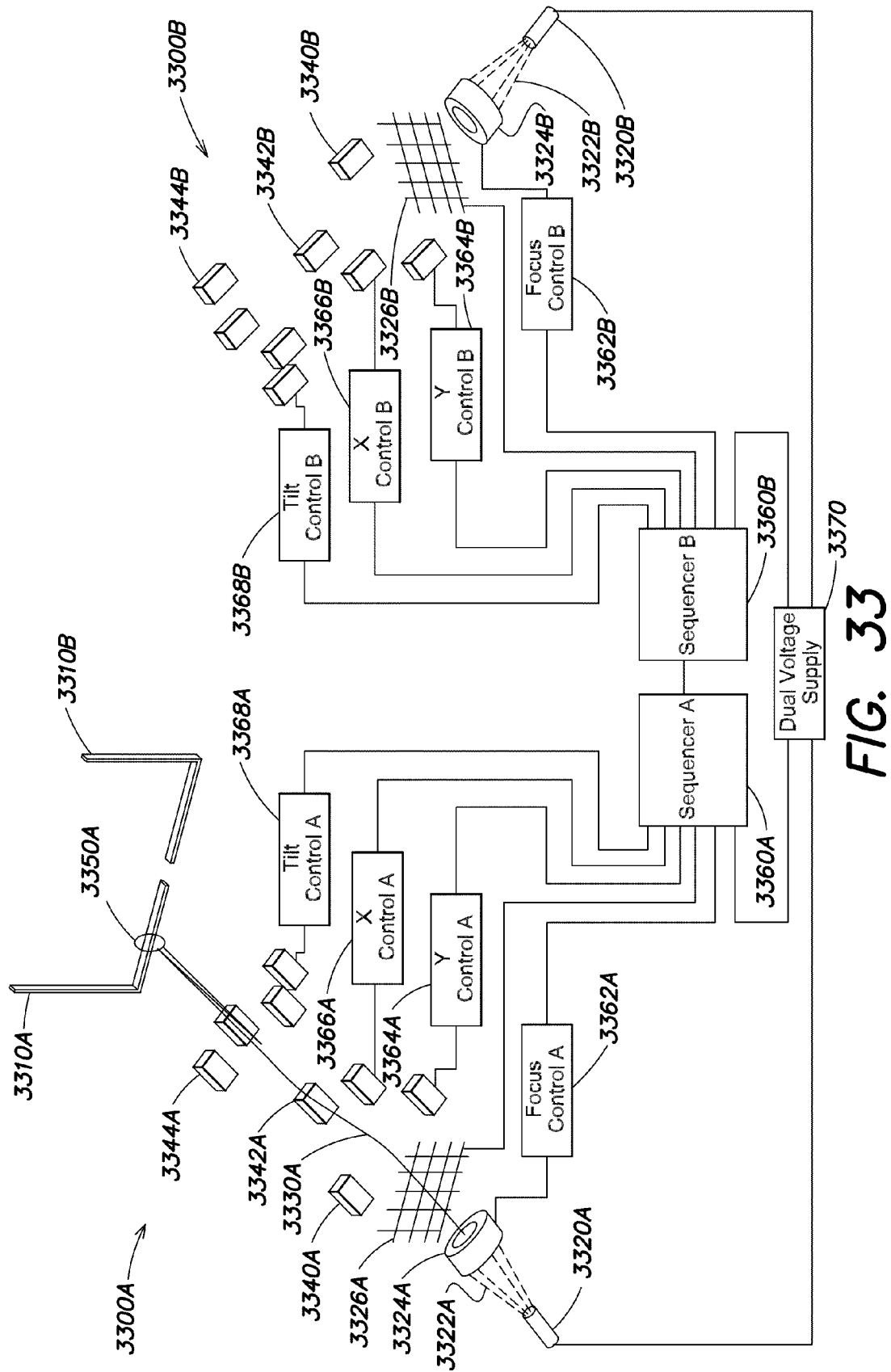
FIG. 33 is a schematic illustration of components of an X-ray generation subsystem that generates radiation at different energy levels for forming a volumetric representation of an item under inspection.

To support dual energy imaging in an inspection system, an X-ray generation subsystem may be adapted to generate X-ray radiation at least two energy levels. FIG. 33 illustrates an approach to incorporate dual energy generation capability into an X-ray generation subsystem which may be employed according to some embodiments of the invention. FIG. 33 schematically illustrates components of such an X-ray generation subsystem. In the exemplary embodiment of FIG. 33, two X-ray generation subsystems, 3300A and 3300B, are illustrated. Each X-ray generation subsystem 3300A and 3300B may have a form factor as illustrated in FIGS. 24A-24D. However, it should be appreciated that the form factor of the X-ray generation subsystem is not critical to the invention and a dual energy capability as described herein may be incorporated into an X-ray generation subsystem of any suitable form factor.

In the example of FIG. 33, the X-ray generation subsystem has L-shaped targets 3310A and 3310B, as illustrated in FIGS. 24A-24D. FIG. 33 also illustrates components of an e-beam generator for each of the X-ray generation subsystems. It should be appreciated that, because FIG. 33 is schematic in nature, various components of the X-ray generation subsystem are not expressly shown. However, techniques and components as described above or as known in the art may be used to construct X-ray generation subsystems as illustrated in FIG. 33, even if not expressly illustrated.

As shown, X-ray generation subsystem 3300A and X-ray generation subsystem 3300B are constructed with similar components such that each may generate radiation of similar characteristics. In an inspection system, X-ray generation subsystems 3300A and 3300B may be operated cooperatively to irradiate an item under inspection. In this example, the X-ray generation subsystems are operated to each generate radiation during a portion of the time that an item under inspection is being irradiated. Here, those intervals are non-overlapping such that X-ray generation subsystems 3300A and 3300B each generates X-ray radiation in alternating intervals.

As an example, each of such intervals may be 20 milliseconds long. During one 20 millisecond interval, the e-beam generator associated with X-ray generation subsystem 3300A may scan an electron beam 3330A from one end of target 3310A to the other end of target 3310A. Upon completion of that scan, in the next 20 millisecond interval, the e-beam generator of X-ray generation subsystem 3300B may scan an electron beam from one end of target 3310B to the other.

To support dual energy imaging, each X-ray generation subsystem may generate radiation of a different energy level during successive intervals when it operates. For example, if two energy levels are generated, a high-energy and a low-energy, a repeating four-phase scan cycle results. For example, in embodiments in which an X-ray generation subsystem scans an e-beam over its target during a 20 millisecond interval, the four-phase scan cycle has four consecutive 20 millisecond intervals. During the first interval, the e-beam generator of X-ray generation subsystem 3300A may scan an electron beam across target 3310A while configured to generate low-energy X-rays. In the second 20 millisecond interval, the e-beam generator of X-ray generation subsystem 3300B may scan an electron beam across target 3310B while X-ray generation subsystem 3300B is configured to generate low-energy X-rays. In the third scan interval, X-ray generation subsystem 3300A may be configured to generate high-energy X-rays and an electron beam may be scanned across target 3310A. In the fourth interval, X-ray generation subsystem 3300B may be configured to generate high-energy X-rays and an electron beam may be scanned across target 3310B. Thereafter, the four-phase cycle may be repeated.

An item moving through an inspection system containing X-ray generation subsystems 3300A and 3300B while this four-phase cycle is being repeated would be irradiated from multiple directions at multiple energy levels. By correlating the detector outputs to times in which the X-ray generation subsystems are generating high- and low-energy X-rays, high and low X-ray data may be collected for a dual energy image analysis. Such an analysis may be performed using techniques as known in the art or in any other suitable way.

In embodiments in which X-ray measurements at more than two energies are desired, the scan cycle may incorporate more than four phases to allow each X-ray generation subsystem to be configured to generate X-rays of each desired energy level during one phase of the cycle. The number of phases in the cycle may also be varied if other than two X-ray generation subsystems are employed.

FIG. 33 illustrates components that may be used to control X-ray generation subsystems to provide a desired multi-phase operation for dual energy X-ray imaging. As shown, X-ray generation subsystem 3300A includes components of an e-beam generator that enable X-ray generation subsystem 3300A to be controlled to provide the multi-phase operation described above.

In the example of FIG. 33, the e-beam generator of X-ray generation subsystem 3300A includes a cathode 3320A, which emits electrons 3322A. A power supply 3370 imparts a potential difference between cathode 3320A and target 3310A that causes the electrons to accelerate towards target 3310A. On the way to target 3310A, electrons 3322A are shaped in a beam and steered to scan across target 3310A.

Electrons 3322A may be shaped in a beam and steered using components as are known in the art or in any other suitable way. Here, electrons 3322A pass through focusing coil 3324A. The electrons emerge in beam 3330A and pass to control grid 3326A. A control voltage applied to control grid 3326A dictates whether the electron beam will be blocked or travel to target 3310A. In the state illustrated in FIG. 33, the control voltage applied allows the beam to pass.

On the way to target 3310A, beam 3330A passes through magnets that steer and shape the beam. Here, two sets of dipole magnets are used to steer the beam in each of two orthogonal directions and a set of quadrupole magnets is used to control the beam shape. Dipole magnets 3340A control deflection of beam 3330A in a direction here denoted as the "Y" direction. Dipole magnets 3342A control deflection of beam 3330A in an orthogonal direction, here denoted as the "X" direction. Quadrupole magnets 3344A control the shape of the beam 3330A. Quadrupole magnets 3344A, for example, may be operated to control the eccentricity of the beam to compensate for differences in angle at which beam 3330A strikes target 3310A as the beam is scanned across the target.

In the embodiment illustrated, each of the beam-steering and beam shaping components has a control circuit that generates electrical signals that change the magnetic field interacting with the beam. Accordingly, FIG. 33 shows focus control circuitry 3362A providing an electrical input to focusing coil 3324A. Control circuitry 3364A provides an electrical input to dipole magnets 3340A. A separate control circuit 3366A may provide an electrical input to dipole magnets 3342A. Further control circuitry 3368A may provide electrical inputs controlling quadrupole magnets 3344A. Each of these control circuits may accept a digital control input and generate an analog drive signal that controls current through a coil or collection of coils that generate a magnetic field. Though, any suitable control mechanism may be used.

To control the energy of X-ray radiation generated when e-beam 3330A strikes target 3310A, the system of FIG. 33 illustrates a dual voltage power supply 3370. In this example, power supply 3370 can output a voltage at one of two levels. For example, dual voltage power supply 3370 may be controllable to provide an output at either 100 kVolts or 180 kVolts. As shown, dual voltage power supply 3370 is coupled to cathode 3320A. When dual voltage power supply 3370 outputs a lower voltage, the potential difference between cathode 3320A and target 3310A will be lower, resulting in the generation of lower energy X-rays. Conversely, when dual voltage power supply 3370 outputs a higher voltage, the potential difference between cathode 3320A and target 3310A will be greater, resulting in the generation of higher energy X-rays.

The components illustrated in FIG. 33 may be operated together to provide multi-phase operation that supports dual energy measurements in an X-ray imaging system. Each of the control circuits 3362A, 3364A, 3366A, and 3368A may output electrical signals in proportion to control inputs provided by a sequencer 3360A. Sequencer 3360A may be a microcontroller or other suitable circuitry programmed or configured to generate control inputs to other components of the system to provide the desired multi-phase operation.

X-ray generation subsystem 3300B likewise includes control components that may be operated in synchronization with the components of X-ray generation subsystem 3300A to provide the desired multi-phase operation. As illustrated, X-ray generation subsystem 3300B includes a cathode 3320B that generates electrons 3322B that may be focused by a focusing coil 3324B. A beam of electrons exiting focusing coil 3324B may selectively pass through control grid 3326B, depending upon the voltage applied to control grid 3326B. If the electron beam passes through control grid 3326B, it may be steered by orthogonal dipole magnets 3340B and 3342B. The beam shape may also be adjusted through quadrupole magnets 3344B.

Electrical signals that operate focusing solenoid 3324B, magnetic dipoles 3340B and 3342B, and magnetic quadrupoles 3344B may be provided by control circuitry 3362B, 3364B, 3366B, and 3368B, respectively. As with X-ray generation subsystem 3300A, these components in X-ray generation subsystem 3300B receive control inputs from a sequencer 3360B.

Sequencers 3360A and 3360B may operate together to generate control signals that result in the desired pattern of dual energy X-rays being generated. For example, during a first phase of a multi-phase cycle, sequencer 3360A may generate control values to cause spot 3350A where electron beam 3330A intersects target 3310A to scan across target 3310A. During this first phase of a cycle, sequencer 3360A may provide a control signal to power supply 3370, configuring power supply 3370 to generate a relatively lower voltage, such as 100 kVolts.

Upon completion of this scan of target 3310A, sequencer 3360A may alter the voltage on control grid 3326A to block beam 3330A from reaching target 3310A. Sequencer 3360A may also signal sequencer 3360B that the scan is complete. This signal may trigger sequencer 3360B to begin a scan of target 3310B with an electron beam. Sequencer 3360B may begin this scan by altering a control voltage on control grid 3326B to allow an electron beam to pass from cathode 3320B to target 3310B. Sequencer 3360B may then generate control signals to control circuits 3362B, 3364B, 3366B, and 3368B that cause a spot, with the desired shape, to scan across target 3310B.

Upon completion of this scan, sequencer 3360B may alter the control voltage on grid 3326B to block the electron beam from reaching target 3310B. Sequencer 3360B may then signal sequencer 3360A that the scan is completed. In response to such a signal, sequencer 3360A may generate a control signal to power supply 3370 that causes power supply 3370 to alter the voltage it supplies. For example, the control signal may cause the power supply 3370 to generate a relatively higher voltage, such as 180 kVolts. With this higher voltage applied to cathode 3320A, sequencer 3360A may alter the control voltage on grid 3326A to allow electron beam 3330A to reach target 3310A. Sequencer 3360A may then generate control signals to the control circuits 3362A, 3364A, 3366A, and 3368A to scan electron beam 3330A across target 3310A and control its shape such that the spot of intersection between electron beam 3330A and target 3310A has a desired shape throughout the scan.

Upon completion of the scan with a higher voltage applied by power supply 3370, sequencer 3360A may again signal sequencer 3360B, which may trigger sequencer 3360B to control the e-beam generator of X-ray generation subsystem 3300B to scan an electron beam across target 3310B with the higher voltage supplied to cathode 3320B.

Operation of X-ray generation subsystems 3300A and 3300B may continue cyclically in this fashion, generating alternatively higher and lower voltage x-rays such that an item under inspection may be imaged.

In the embodiment illustrated in FIG. 33, an electron beam is scanned across a target by steering the beam to a series of closely spaced but discrete locations. For example, the e-beam generator of X-ray generation subsystem 3300A, during a scan of target 3310A, may steer electron beam 3330A to approximately 1,000 scan positions across target 3310A. In an embodiment in which a scan is performed in approximately 20 milliseconds, the electron beam may be steered to each scan position for approximately 20 microseconds before moving to the next scan position. Accordingly, sequencer 3360A and sequencer 3360B, when actively controlling a scan, may output new control values at a rate of approximately one set of values every 20 microseconds.

To scan a beam across a target, such as target 3310A, a different combination of control inputs is provided to each of the electron beam steering components, which are, in the example of FIG. 33, illustrated as dipole magnets 3340A and 3342A. The Applicants have appreciated that, to improve the quality of X-ray images formed, it may be also be desirable to provide different beam-shaping inputs for each location along the target to which the e-beam is to be steered. Accordingly, for each location, separate control inputs may be provided to control circuitry 3362A and 3368A which control the beam-shaping components.

Further, Applicants have recognized that, though the scan path of an electron beam across a target is the same regardless of the energy of X-rays to be generated, the control values to position and shape the electron beam appropriately vary, depending on the energy of the X-rays to be generated.

Figure 34:
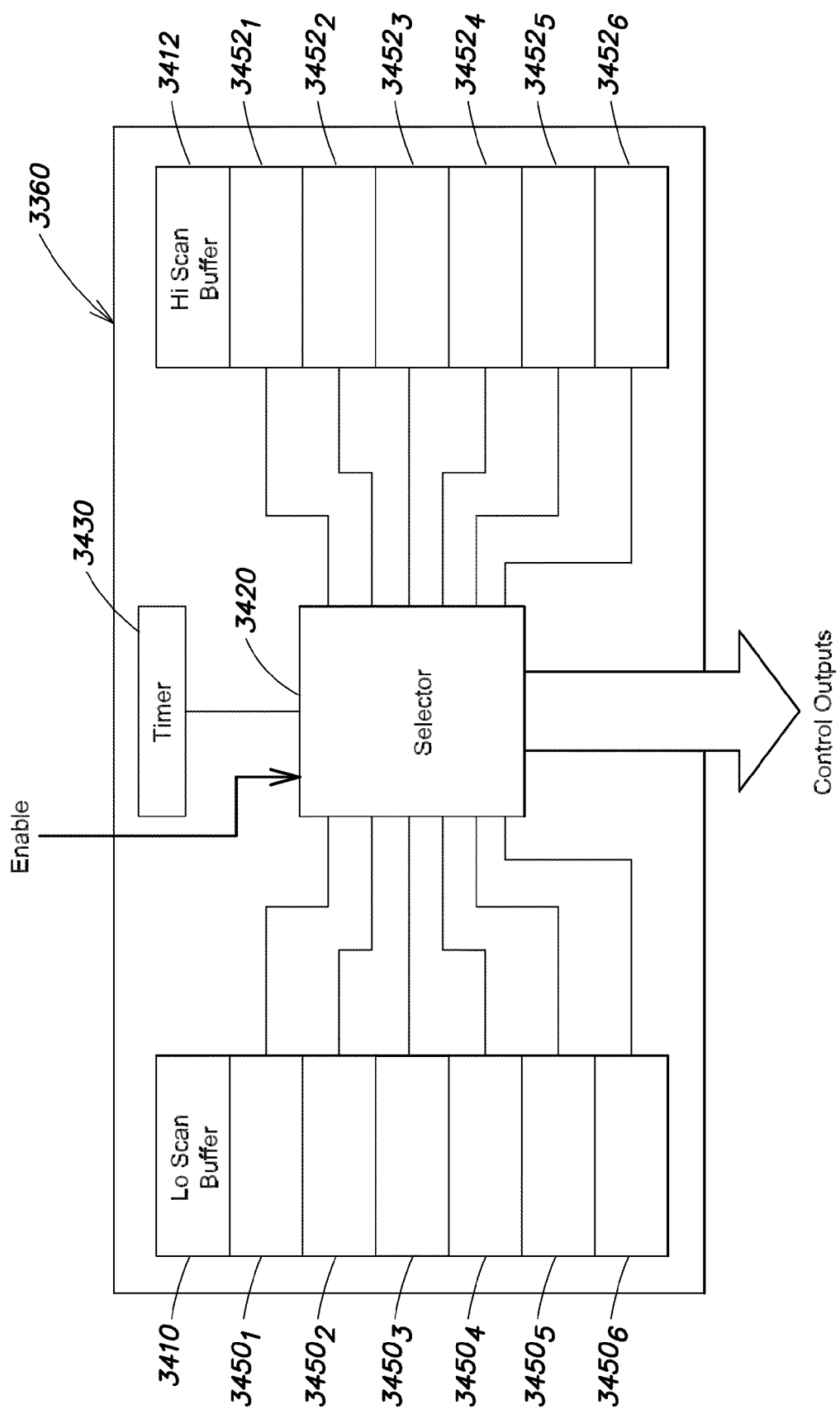
FIG. 34 is a schematic illustration of a sequencer of the system of FIG. 33.

FIG. 34 illustrates schematically circuitry that may be used to implement a sequencer, such as sequencer 3360A or 3360B that provides appropriate control outputs throughout a multi-phase scan cycle. Here, FIG. 34 illustrates a sequencer 3360 that may be adapted to control either X-ray generation subsystem 3300A or X-ray generation subsystem 3300B.

In this example, sequencer 3360 contains computer storage media, such as random access memory or non-volatile memory, that may be loaded with values representing control inputs to the control elements of an e-beam generator. This information may be organized sequentially, as in a buffer, with each successive location containing control values for a scan position. Separate buffers may be provided to store control inputs for a scan when X-rays of different energies are to be generated.

FIG. 34 illustrates a scan buffer 3410 that, for example, may store sequential control inputs to scan an electron beam across a target while low energy X-rays are being generated. Similarly, a scan buffer 3412 may be provided to hold control inputs for a scan when high-energy X-rays are to be generated. Though FIG. 34 shows only two scan buffers, which may be suitable for use in embodiments in which X-rays of only two energies are to be generated, it should be appreciated that, in embodiments in which more than two energies are to be generated, more than two scan buffers may be provided.

Scan buffer 3410 in this example is shown to contain buffer locations $3450_1$, , , $3450_6$. Similarly, scan buffer 3412 is shown to contain buffer locations $3452_1$, , , $3452_6$. It should be appreciate that FIG. 34 is a simplified representation of a sequencer, and only six scan buffer locations are shown for simplicity. In some embodiments, many more than six scan buffer locations may be provided. As an example, in some embodiments, it is contemplated that each scan buffer will contain approximately 1,000 locations.

Regardless of the number of locations in each scan buffer, each scan buffer location may contain a set of values that identify control values for both beam-steering components and beam-shaping components. For example, in the system of FIG. 33, a scan buffer in sequencer 3360A may contain control inputs for control circuits 3364A and 3366A that steer the beam and control inputs for control circuits 3362A and 3368A that can shape the beam. Though, it should be appreciated that various data compression techniques may be employed that avoid the need to store a value for each control input in each buffer location. For example, each buffer location may store a control value for a control parameter only when the value of that parameter changes from the value stored in a previous location.

Regardless of the format in which information is stored in each scan buffer location, to implement a scan, selector 3420 may read values from successive locations and, based on the information read, output values to control circuits that cause an electron beam to scan across a target and generate radiation at a desired energy level. Here, selector 3420 may be circuitry configured or programmed to implement a state machine. The state machine may track whether a high-energy or low-energy scan is being performed and, based on the type of scan, read data from the appropriate scan buffer.

Selector 3420 may be timed by a timer 3430 that pulses at defined intervals. In response to each pulse, selector 3420 may change state. In an example in which an electron beam is steered to a new scan position approximately once each 30 microseconds, timer 3430 may output a pulse each 30 microseconds. In response to such a pulse, selector 3420 may read a value from the next location in a scan buffer and generate control outputs appropriately.

In the four-phase operation described above, selector 3420 will initially begin reading values from scan buffer 3410. As each value is read, selector 3420 will translate the control values into control outputs for the components of its associated X-ray generation subsystem. Upon reaching the last location in scan buffer 3410, selector 3420 may provide an output signaling another sequencer to begin controlling its scan. Also at this time, selector 3420 may set its control outputs so that its associated X-ray generation subsystem does not generate X-rays.

Selector 3420 may then hold its output state until it receives an enable input, which may be provided by another similar sequencer associated with another X-ray generation subsystem. Such an input may indicate that the other sequencer has completed its scan. Selector 3420 may then begin another scan, using control values obtained from scan buffer 3412. Selector 3420 may read values in sequence from scan buffer 3412 for each pulse of timer 3430 until a high energy scan is completed.

Selector 3420 then may again issue an output signaling another sequencer to begin a scan and hold the control outputs of sequencer 3360 until another enable input is received. At a subsequent time, when such an enable input is repeated, selector 3420 may repeat the process of generating control outputs based on values in scan buffer 3410. This process may be repeated for so long as X-rays to image an item under inspection are to be generated.

It should be appreciated that FIGS. 33 and 34 are schematic illustrations of components that may be used to provide the desired level of control in an X-ray generation subsystem. Various alternatives are possible. For example, FIG. 33 shows two sequencers. However, control of X-ray generation subsystems 3300A and 3300B may be provided by a single control circuit rather than separate components. Further, exemplary beam-steering and beam-shaping mechanisms are pictured in FIG. 33, but any suitable beam-steering or beam-shaping mechanism may be employed. Further, though it is described that control is performed in circuitry, control mechanisms may be provided in any suitable way. Some or all of the functions described above may be implemented by programming a processor. Also, though FIG. 34 illustrates that control values are pre-computed and stored as digital quantities in computer memory, other implementations are possible. Some or all of the control values may be generated on the fly using computational circuitry or other suitable approaches.

The X-ray generation subsystems and control components illustrated in FIGS. 33 and 34 may be used in an X-ray imaging system that employs X-ray detectors that are sensitive to an energy spectrum that includes both high and low energy X-rays generated by the X-ray generation subsystems. Low energy measurements may be obtained by recording the output of the detectors while the X-ray generation subsystems are generating low energy X-rays. Similarly, high energy measurements may be made while the X-ray generation subsystems are generating high energy X-rays.

Figure 35:
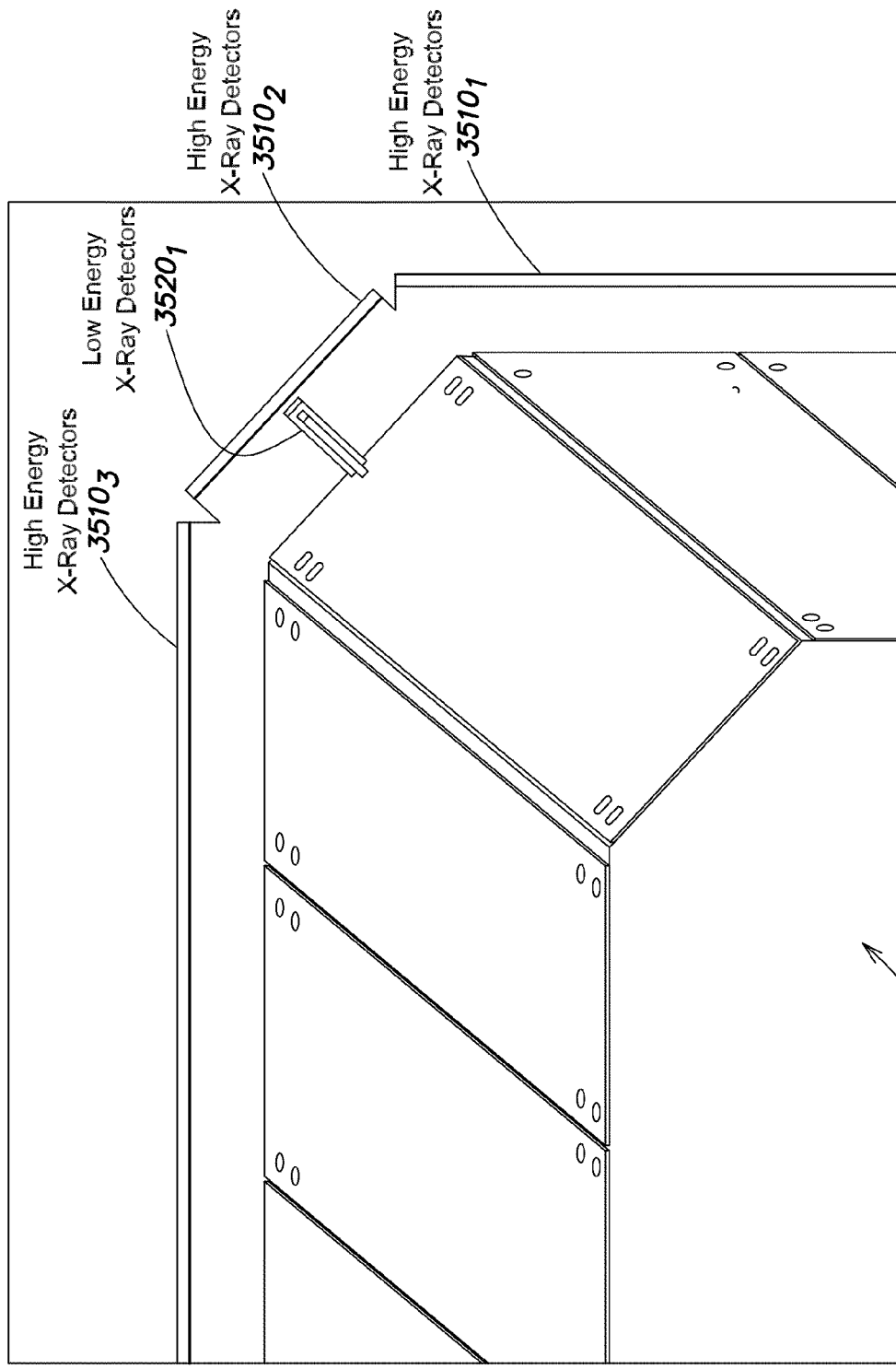
FIG. 35 is a sketch of a portion of an X-ray inspection system using different numbers of detectors sensitive to different energy levels.

An alternative approach for performing dual energy imaging is to use at least two types of detectors, with detectors in each set sensitive to different energy levels. Heretofore, a drawback of such an approach has been the cost of two sets of detectors, one to detect low energy X-rays and one to detect high energy X-rays. FIG. 35 illustrates a system configuration that takes advantage of an ability to control the point of origination of X-ray radiation that exists in most inspection systems that form volumetric images. The system illustrated avoids the need for two full sets of detectors in order to make dual energy measurements. Such a configuration may be particularly useful in a security inspection system configured to identify particular objects that may constitute threats, such as weapons, explosives or other contraband, within items under inspection.

Such systems frequently operate by processing a volumetric image to identify objects based on density or other characteristics. Analysis then may be performed on the identified objects to determine characteristics that may be indicative of threat or non-threat objects. Atomic number, which may be inferred from dual energy X-ray measurements, is one such characteristic. FIG. 35 illustrates a low cost system configuration that can provide information useful in performing such a threat assessment.

Figure 10:
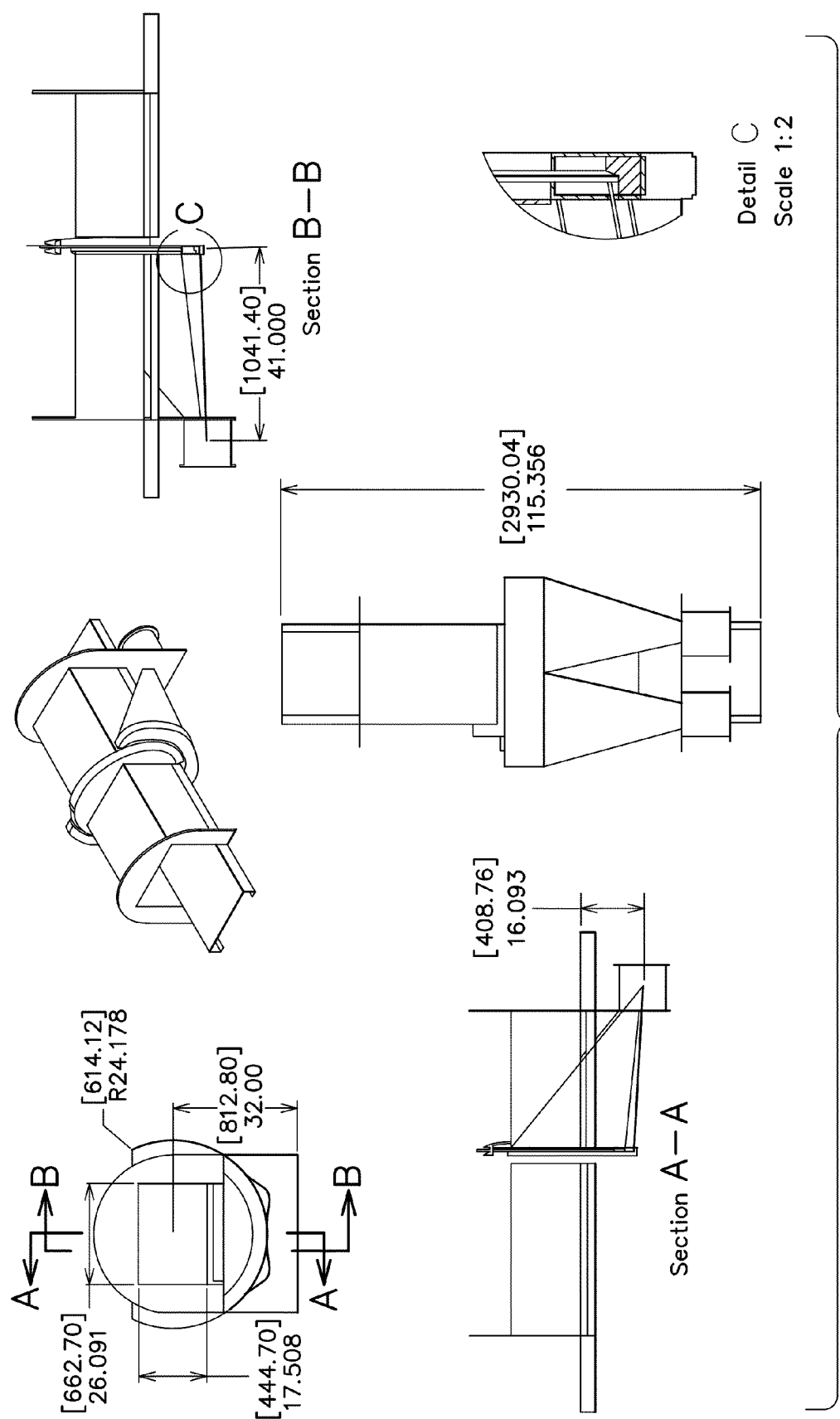
Figure 11:
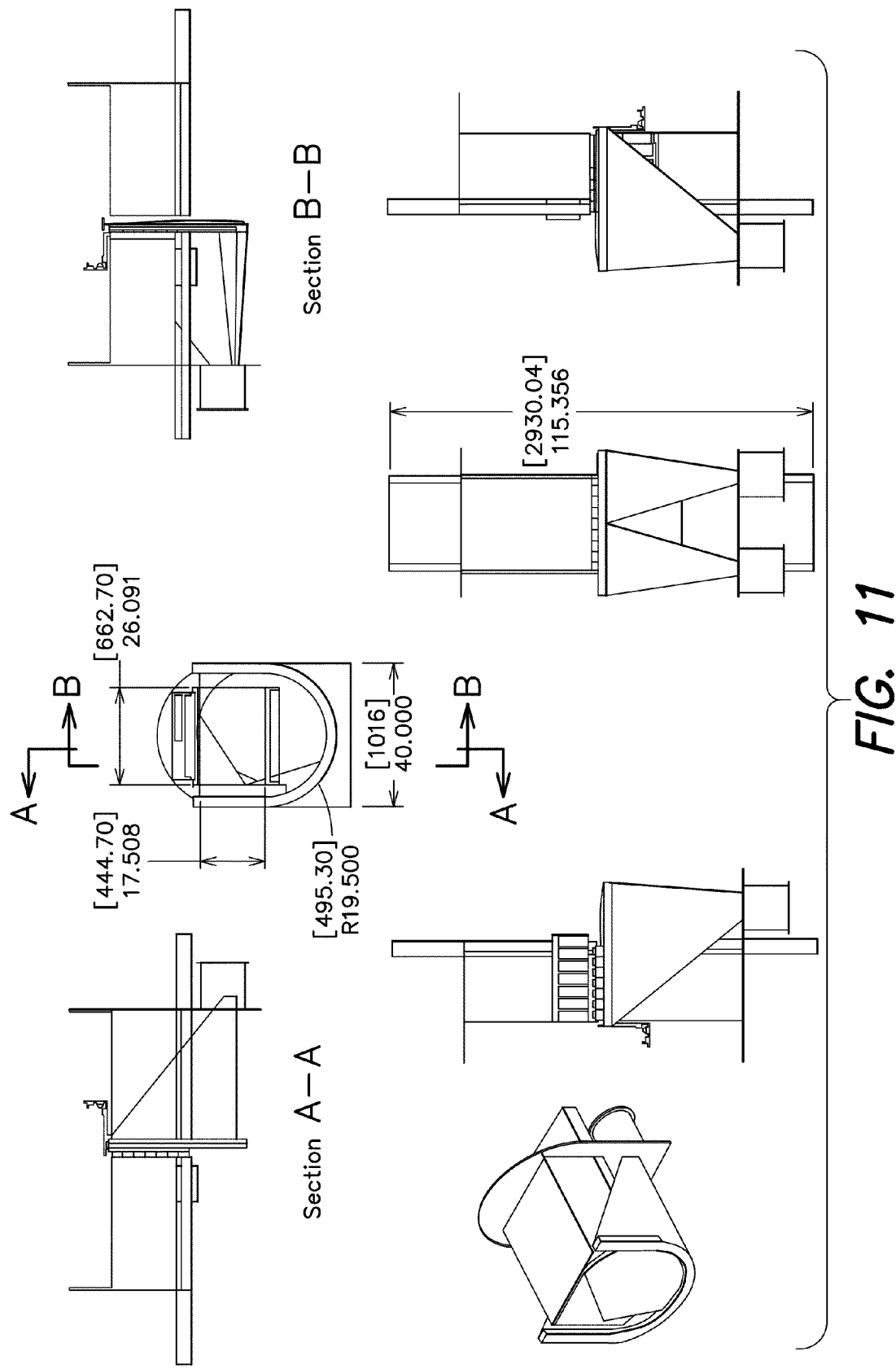
Figure 12:
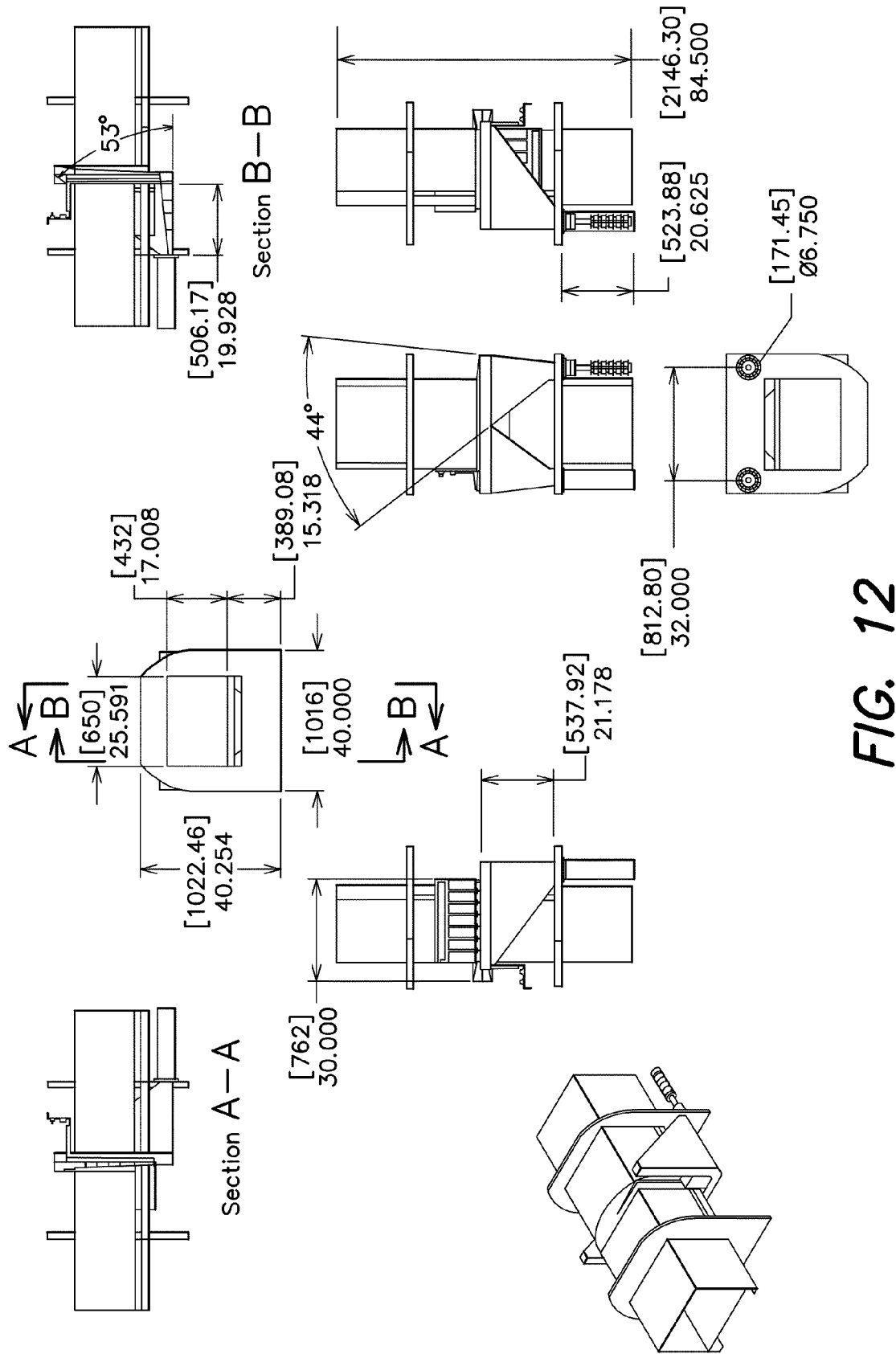
Figure 13:
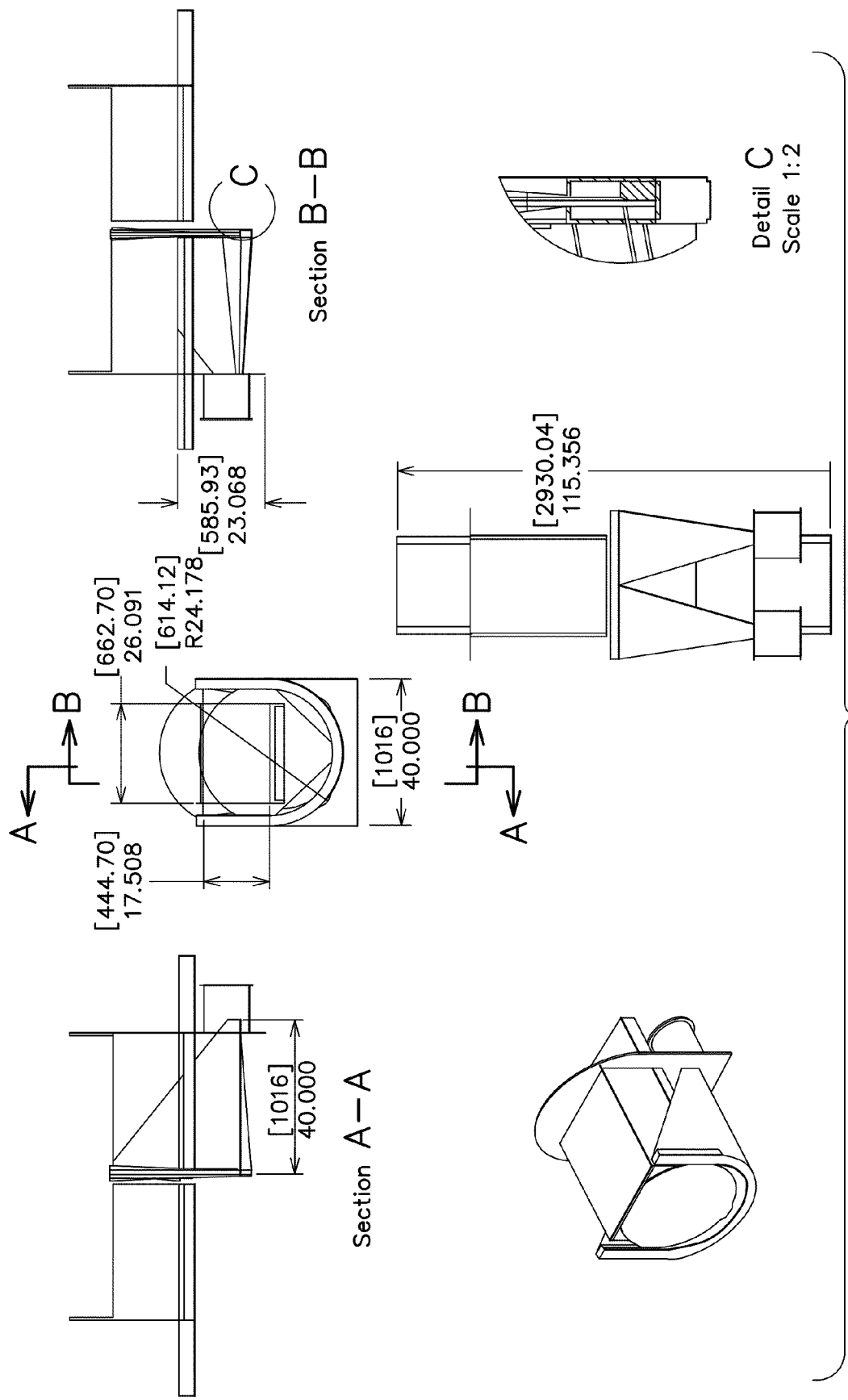

FIG. 35 illustrates a portion of an inspection system. FIG. 35 illustrates a portion of a system such as is illustrated in FIG. 10. The portion shown is a corner surrounding a tunnel 3500, through which items under inspection may pass. FIG. 35 shows that the tunnel 3500 is lined with X-ray detectors sensitive to X-ray radiation of a first energy level. Here, the first energy level is a relatively high energy level, such as 150 keV or above. In the embodiment of FIG. 35, detector segments $3510_1$, $3510_2$ and $3510_3$ are such high energy X-ray detectors.

FIG. 35 shows only a portion of tunnel 3500. Accordingly, only a portion of the high energy X-ray detectors that may exist in an inspection system are illustrated. The high energy X-ray detectors may be positioned around tunnel 3500 in a U-shape or a staple-shape which is illustrated in conjunction with FIG. 17 above. However, the specific configuration of radiation detectors is not critical to the invention as any suitable configuration may be used.

Regardless of the configuration of high-energy X-ray detectors, the inspection system illustrated in FIG. 35 may include a smaller number of energy detectors sensitive to X-rays of a second energy level. In the example of FIG. 35, the second energy level is low energy X-rays, such as 120 keV or below. Here, low energy detector segment $3520_1$ is illustrated.

As can be seen, low energy detector $3520_1$ occupies a portion of the area occupied by high energy X-ray detector segments $3510_1$, $3510_2$ and $3510_3$. Though other low energy detector segments may be mounted within an X-ray inspection system, the total area occupied by the low energy X-ray detectors may be substantially less than the area occupied by high energy X-ray detectors. In some embodiments, the total area of low energy X-ray detectors is 10% or less than the area occupied by high energy X-ray detectors. As a specific example, the area of low energy X-ray detectors may be 1% or less.

In the embodiment illustrated, low energy X-ray detector segment $3520_1$ is mounted on top of high energy X-ray detector segment $3510_2$. Such a configuration is possible because X-rays having an energy to which high energy X-ray detector segment $3510_2$ are sensitive may generally pass through low energy X-ray detector segment $3520_1$ without substantial attenuation. Further, any attenuation that does occur may be predictable and measurements made by detectors in high energy X-ray detector segment $3510_2$ that are below low energy X-ray detector segment $3520_1$ may be adjusted for any attenuation caused by low energy X-ray detector segment $3520_1$. However, it is not a requirement that low energy X-ray detector segment $3520_1$ be superimposed on a high energy X-ray detector segment. As examples of other possible configurations, the low energy X-ray detector segment may be placed beside a high energy X-ray detector segment or between high energy X-ray detector segments.

Figure 36:
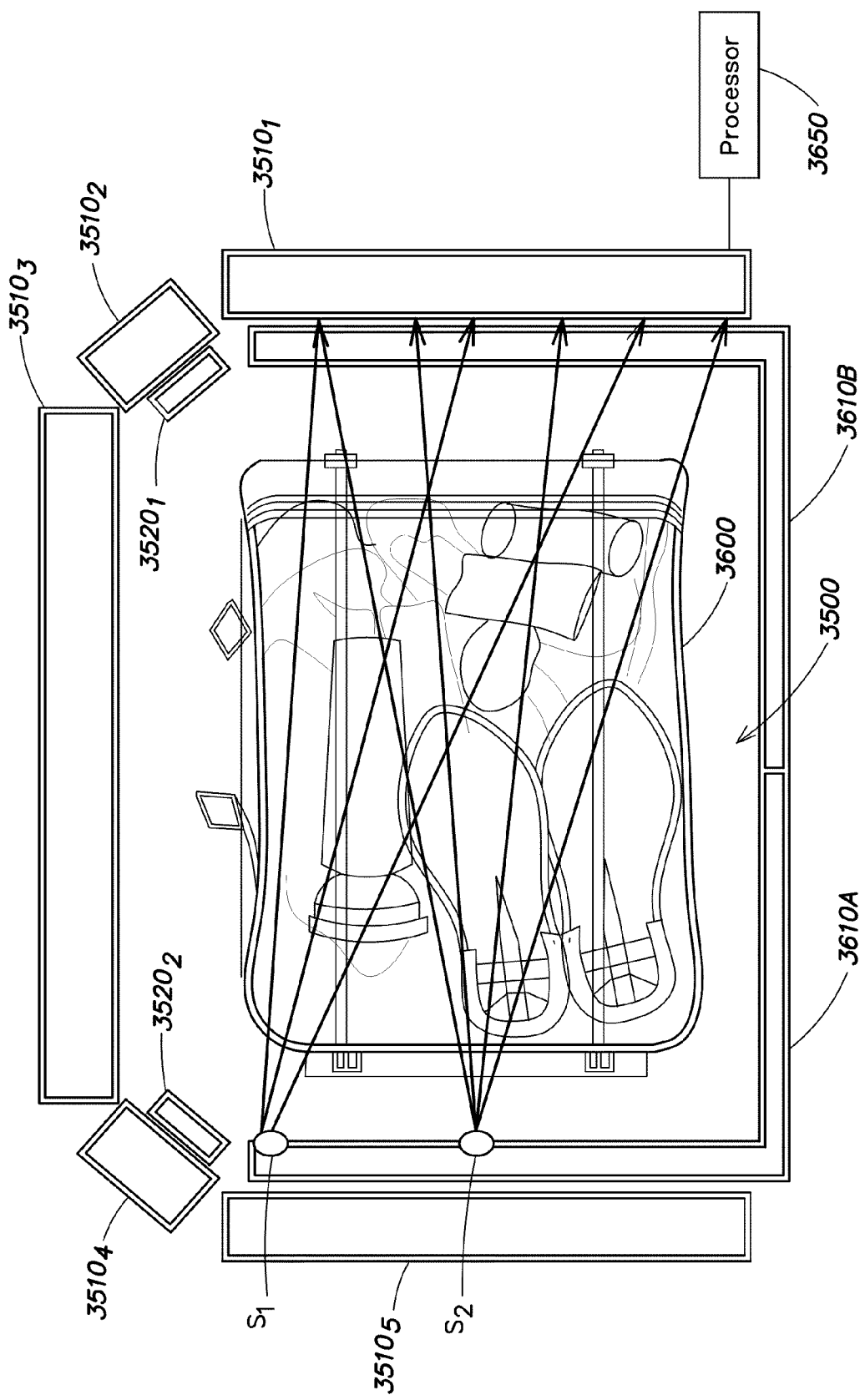
FIG. 36 is a schematic illustration of operation of a system with a detector configuration as illustrated in FIG. 36 during a first phase of inspection.

Regardless of the number and positioning of low energy X-ray detector segments, FIG. 36 illustrates a process by which an inspection machine configured generally as illustrated in FIG. 35 may be operated to perform inspection using dual energy techniques. FIG. 36 illustrates schematically a cross-sectional representation through such an inspection system. An item under inspection 3600 is shown within tunnel 3500. In the illustrated embodiment, high energy X-ray detector segments $3510_1$, $3510_2$ ... $3510_5$ are arrayed generally in a U-shape around sides of tunnel 3500.

Target 3610A and 3610B are also shown. Targets 3610A and 3610B may each form a portion of an X-ray generation subsystem employing a steered electron beam as described above. An electron beam may be steered to multiple scan positions around targets 3610A and 3610B and, at any time during the scan, X-ray radiation will originate from the current scan position.

While the beam scanned across the targets, the outputs of high energy X-ray detector segments may be captured and processed, such as in processor 3650. As illustrated in FIG. 35, at each scan position, such as scan positions $S_1$ and $S_2$, the radiation generated from the targets 3610A and 3610B will travel along multiple rays through item under inspection 3600 to one of the detector segments $3510_1$ ... $3510_5$. As a result, the captured outputs of the X-ray detector segments represent measurements taken from multiple points of view, allowing processor 3650 to compute a volumetric image of item under inspection 3600 as it passes through tunnel 3500 past the X-ray detectors.

In embodiments in which X-ray detector segments $3510_1$ ... $3510_5$ are sensitive to radiation of a particular energy, the formed volumetric image will be a single energy image. It may, for example, contain information about density of objects within item under inspection 3600. However, as a single energy measurement, it will not contain information about atomic number of the materials inside item under inspection 3600. Nonetheless, known single energy volumetric image analysis techniques are capable of identifying boundaries of objects.

Figure 37:
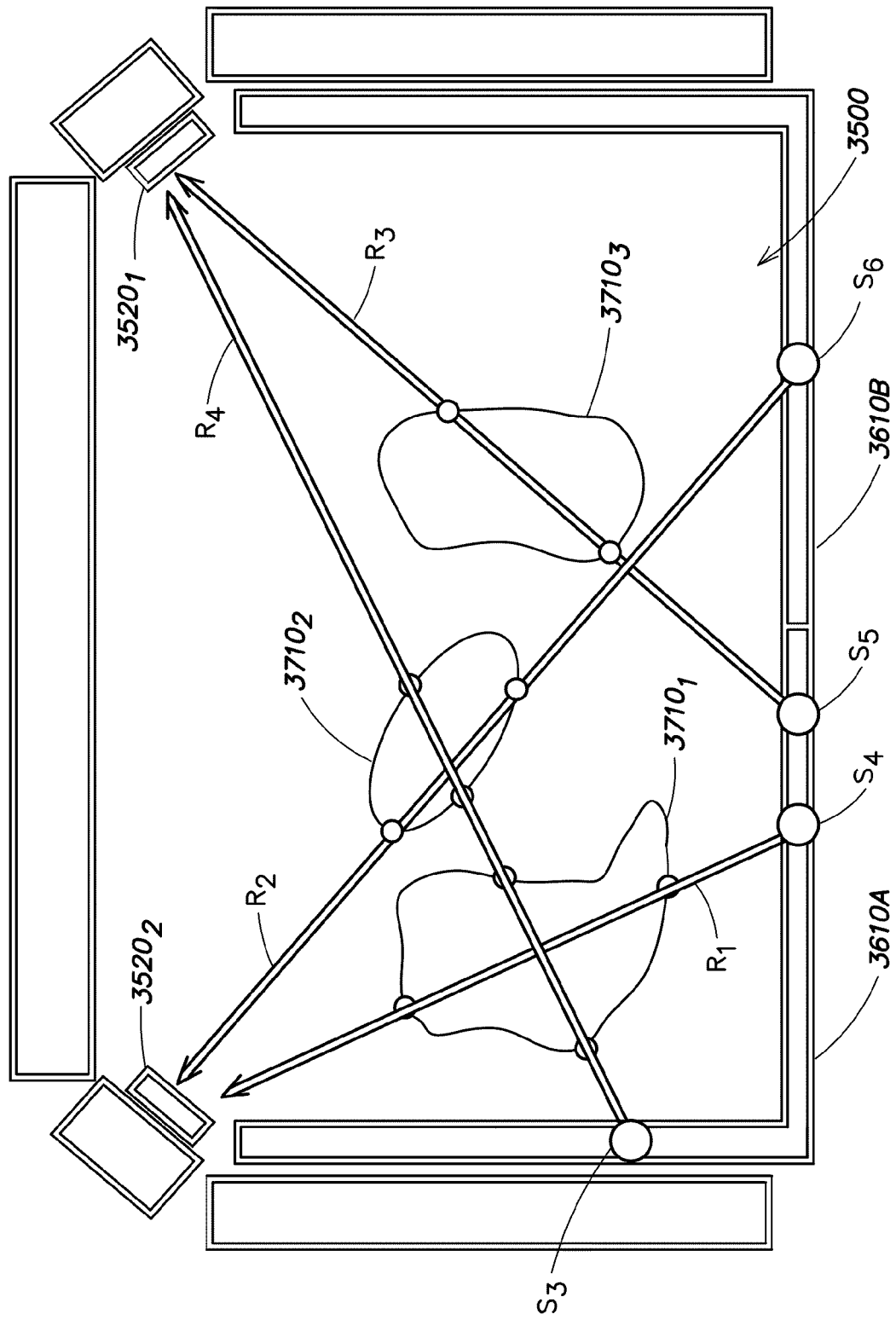
FIG. 37 is a sketch illustrating operation of a system with a detector configuration as illustrated in FIG. 35 during a second phase of operation.

Turning to FIG. 37, a result of the single energy volumetric image is schematically depicted. In the example of FIG. 37, analysis of a single energy volumetric image has resulted in the identification of objects of sufficient density that they are potentially threat objects within item under inspection 3600. For exemplary purposes, FIG. 37 illustrates three such objects identified, objects $3710_1$, $3710_2$ and $3710_3$. In addition to identifying that such objects are present, processing within processor 3650 (FIG. 36) has determined the location within tunnel 3500 of those objects.

Other objects may be present within item under inspection 3600, such objects may be of such low density as to have an insignificant impact on X-rays passing through item under inspection 3600. In the example of a security inspection system, a suitcase may contain clothes, which are relatively low density, and metal objects and plastic objects, which may be of higher density. FIG. 37 illustrates that the higher density objects have been identified for subsequent processing. In some embodiments, lower density objects may be omitted from subsequent analysis without appreciably affecting the results. Though, other embodiments are possible in which even lower density objects are considered or the nature of background material or other characteristics of item under inspection are incorporated into image processing methods.

Regardless of the number or nature of objects identified for further processing, dual energy processing on the identified objects may be performed by selecting outputs of low energy detectors at selected times. FIG. 37 illustrates various possible rays from potential scan positions on targets 3610A and 3610B and low energy detector segments $3520_1$ and $3520_2$. During a scan, such rays will extend from each scan position to each low energy detector.

According to some embodiments of the invention, some such rays are selected to provide a limited amount of low energy data. The selected rays are those that pass through locations within item under inspection 3600 that contain objects identified for further analysis without passing through other objects that could alter low energy radiation passing through item under inspection 3600. In this way, the radiation measured at the low energy detectors provides a reliable indication of the interaction between low energy X-rays and a particular one of the identified objects. This information is adequate to perform dual energy analysis that indicates an atomic number of the object.

For example, FIG. 37 indicates that when an electron beam is focused in scan position $S_4$, ray $R_1$ passes through object $3710_1$ and reaches low energy X-ray detector $3520_2$ without interacting significantly with any other objects within item under inspection 3600. Similarly, when an electron beam is focused on scan position $S_6$, ray $R_2$ passes through object $3710_2$ without interacting with other objects. Similarly, when an electron beam is focused on scan location $S_5$, ray $R_3$ passes through object $3710_3$ on its way to low energy X-ray detector segment $3520_1$ without interacting with other objects. Accordingly, by selecting the output of the low energy detectors when an electron beam is in scan locations $S_4$, $S_5$ and $S_6$, low energy data may be obtained, allowing processor 3650 to compute the atomic number of objects $3710_1$, $3710_2$ and $3710_3$. Based on this computation, processor 3650 may more reliably determine whether any of objects $3710_1$, $3710_2$ or $3710_3$ within the item under inspection constitutes a threat.

Conversely, ray $R_4$ is shown passing through multiple objects, here objects $3710_1$, $3710_2$. Accordingly, when an electron beam is focused on scan location $S_3$, the data recorded at low energy detector segment $3520_1$ reflects a combination of the effects of objects $3710_1$ and $3710_2$. While such a measurement may provide information about both objects $3710_1$ and $3710_2$, it is not directly useful in determining the atomic number of either objects $3710_1$, $3710_2$ as would be the information obtained for measurements based on rays $R_1$ or $R_2$.

Accordingly, processor 3650 may be operated according to a method in which scan locations for performing low energy X-ray measurements are identified and prioritized, with scan locations providing measurements through isolated objects being preferentially selected. When an item under inspection contains too many objects or the objects are positioned in such a fashion that no scan position allows some objects to be isolated, rays that are the least subject to interference as a result of passing through multiple objects are next selected or alternative processing approaches are taken to analyze the content of the item under inspection.

It should be appreciated that FIG. 37 schematically illustrates a processing approach and the data reflected in that figure may be collected in any suitable way. For example, it is not a requirement that the scan locations, $S_4$, $S_5$ and $S_6$ be identified prior to the time at which low energy detector outputs are captured. As an example of one possible implementation, the inspection system illustrated in FIG. 37 could be operated to perform a single scan around targets 3610A and 3610B during which detector outputs of both high energy detector segments and low energy detector segments may be captured. Once processor 3650 completes processing on the outputs of the high energy detector segments, it may identify outputs of the low energy detector segments $3520_1$ and $3520_2$ at times that correspond to rays of interest through the item under inspection 3600. However, the low energy and high energy measurements may be collected at any suitable times in any suitable orders.

Figure 38:
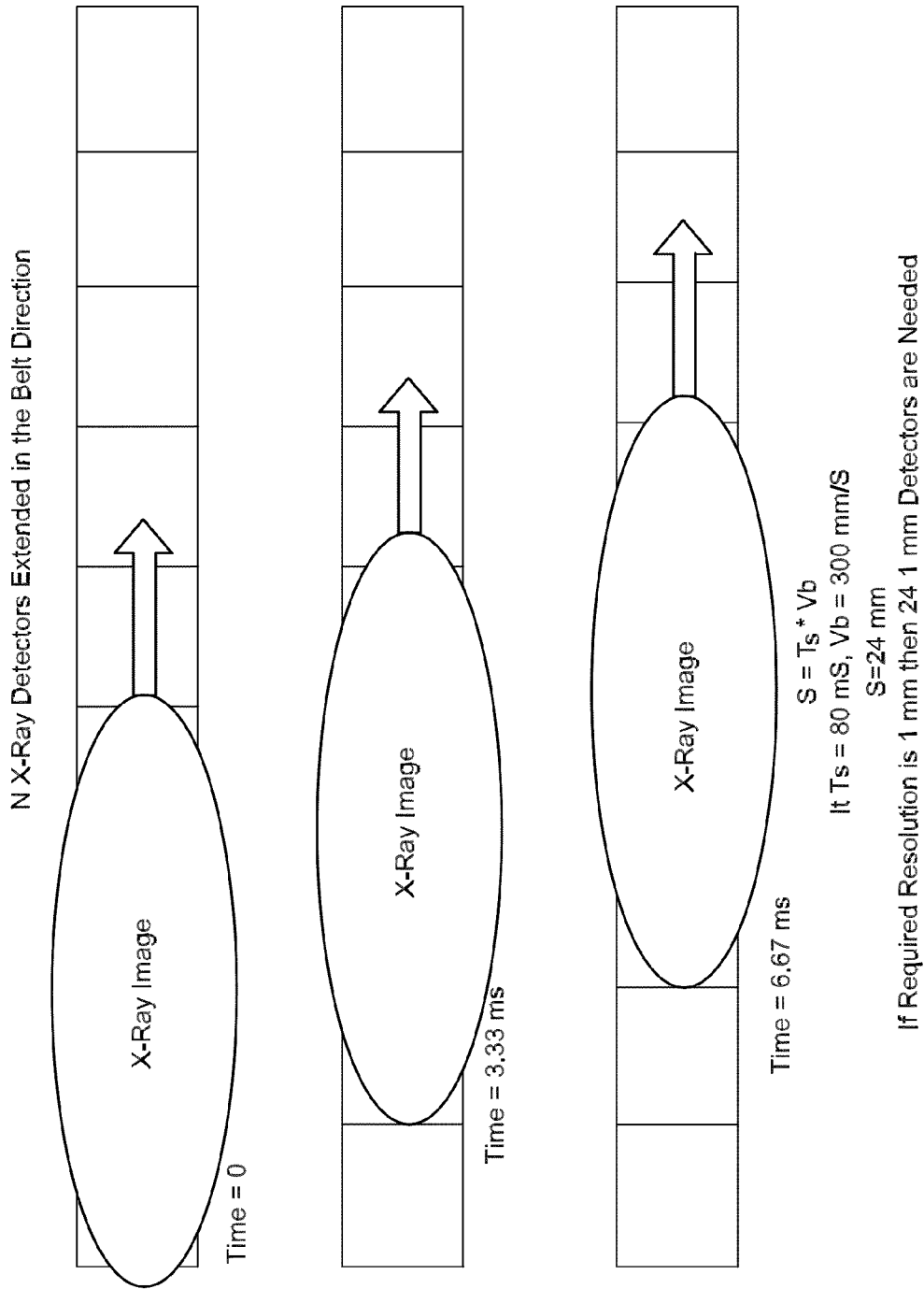
FIG. 38 is a sketch illustrating aspects of the detector arrays illustrated in FIG. 35.

In the example embodiment of FIG. 35, both the high energy detector segments and the low energy detector segments extend a noticeable amount in a direction aligned with the axial dimension of tunnel 3500. The amount by which the detector segments extend in this axial dimension may depend on the speed at which items move through the tunnel relative to the time it takes to complete a scan. FIG. 38 illustrates an approach for determining an extent of each detector segment in the tunnel direction and the selection of specific detector outputs from the detector segment at different times during a scan.

In the illustration provided by FIG. 38, the scan time is 80 milliseconds, meaning that an electron spot will scan fully across all targets, at all desired energy levels, in this total scan time of 80 milliseconds. In the example, the item under inspection is positioned on a conveyor that is moving at a speed of 300 millimeters per second. Accordingly, in the time it takes to complete one scan, the item under inspection will have moved a total of 24 millimeters. Accordingly, the detector arrays must extend in the longitudinal tunnel dimension 24 millimeters to ensure that that the same portions of the item under inspection that are imaged at the beginning of the scan are still being imaged at the end of the scan.

Though, if a single 24 millimeter detector cell were provided, the resolution of the image formed with the inspection system will be relatively poor. Accordingly, FIG. 38 illustrates that according to some embodiments of the invention, each of the detector segments includes multiple smaller detector elements arrayed in the longitudinal direction. At different times, the outputs of different subsets of the detector elements are selected and used for performing an X-ray image.

In the example of FIG. 38, each of the individual elements is approximately one millimeter wide. Accordingly, given the belt speed in the example, after 3.33 milliseconds, a portion of an item under inspection aligned with the first detector element in the array will be aligned with the second detector element of the array. Similarly, after 6.67 milliseconds, that same portion with become aligned with the third detector element of the array. To provide a more accurate X-ray image, throughout a scan, the subset of detector elements selected changes to insure that the same portions of the item under inspection are represented by the captured detector outputs.

Figure 39B:
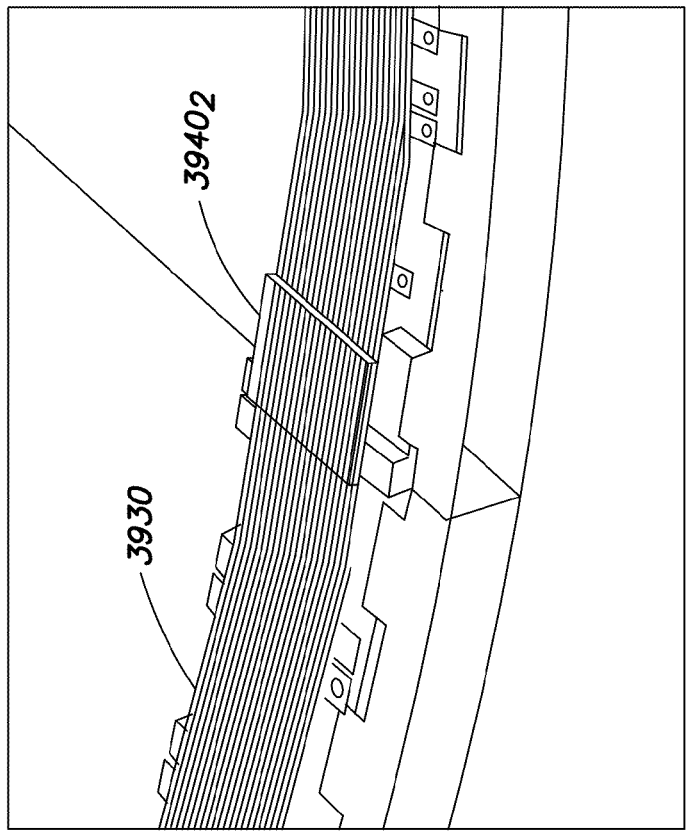
FIG. 39B is an enlarged view of a portion of the system illustrated in FIG. 39A.
Figure 39A:
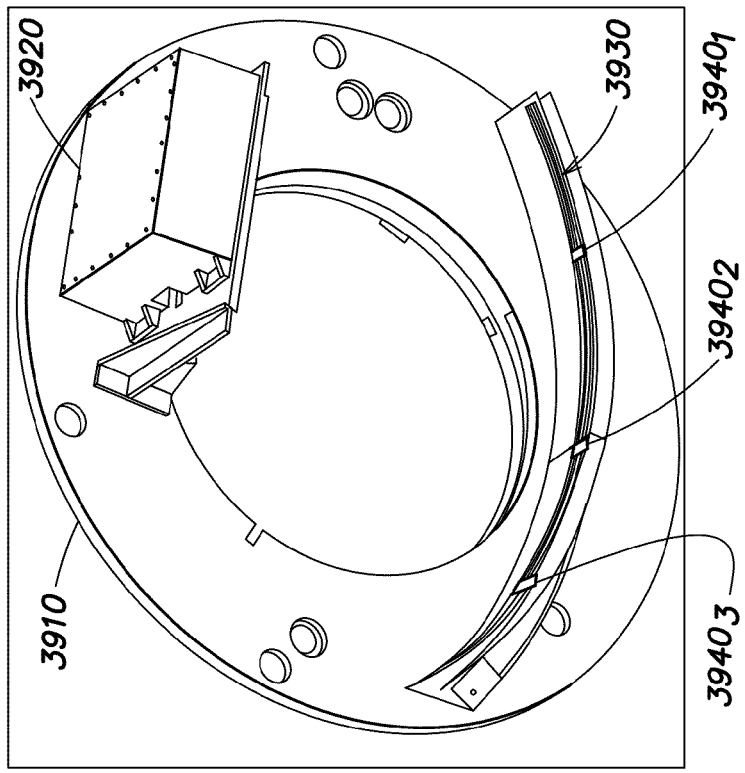
FIG. 39A is a sketch of a volumetric inspection system employing a rotating gantry configured with different numbers of detectors sensitive to X-ray radiation of different energy levels.

FIGS. 35, 36 and 37 illustrate a dual energy measurement technique using a relatively small number of detector segments sensitive to X-rays of a second energy. In that embodiment, rays of radiation passing through an item under inspection are selected based on a point of origin of the radiation relative to the low energy detector segments and objects in the item under inspection. In that embodiment, steering an electron beam to various scan locations on a target is used to provide radiation originating from different locations at different times such that the detector outputs attributable to specific rays can be selected. It is not a requirement of the invention that radiation originating from multiple points be provided by is scanning an electron beam across a target. FIGS. 39A and 39B illustrate an alternative embodiment.

In the embodiment of FIGS. 39A and 39B, mechanical motion of the source relative to the item under inspection is used to generate rays having different points of origin at different times. Accordingly, FIG. 39A shows an X-ray source 3920 mounted on a gantry 3910. Gantry 3910 and source 3920 may be components as are known in the art in a mechanical CT system.

FIG. 39A similarly shows that gantry 3910 includes an opening through which items under inspection may pass. On the opposite side of this opening from source 3920 is a detector array 3930. Detector array 3930 may be mounted to gantry 3910 as in a conventional CT system. In this embodiment, detector array 3930 may comprise detectors that are sensitive to high energy X-rays, similar to detector array segments $3510_1 \ldots 3510_5$ (FIG. 36).

As with the embodiment illustrated in FIG. 35, low energy detector segments $3940_1 \ldots 3940_3$ may be overlaid on high energy detector array 3930. FIG. 39B shows an enlarged view of a portion of detector array 3930 overlaid with a low energy detector segment $3940_2$. Accordingly, a system incorporating the gantry as illustrated in FIG. 39A may collect, as in a conventional CT system, high energy measurements sufficient to compute a volumetric image of an item under inspection. Based on this image, objects may be identified and selected ones of the measurements made with the low energy detector segments $3140_1 \ldots 3140_3$ may be identified to provide dual energy information about specific objects.

Figure 40A:
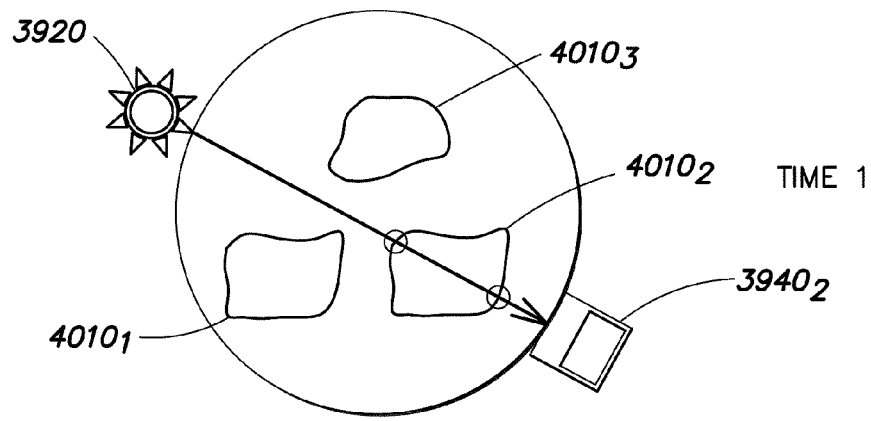
FIGS. 40A, 40B, and 40C are sketches illustrating operation of the system of FIG. 39A.
Figure 40B:
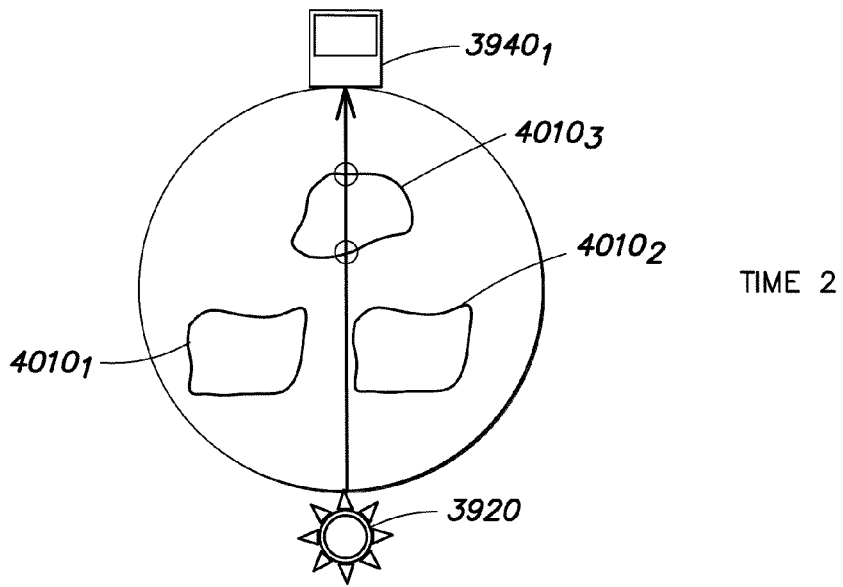
Figure 40C:
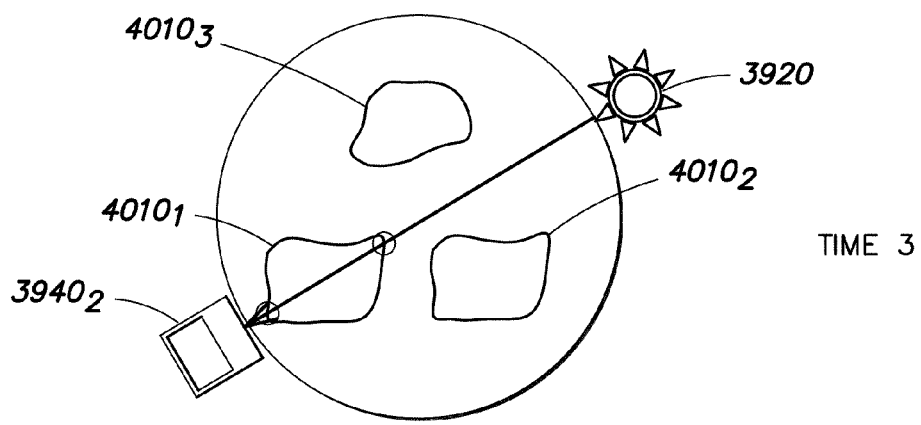

As with the embodiment of FIG. 35, the identified low energy measurements may represent measurements of interactions of X-rays through one or a small number of objects within the item under inspection. FIGS. 40A, 40B and 40C illustrate this approach. FIG. 40A illustrates that objects $3140_1 \ldots 3140_3$ have been identified. At some time, denoted in FIG. 40A as TIME ONE, a ray passing from source 3920 to low energy detector segment $3940_2$ passes through object $410_2$, without being substantially affected by other objects. Accordingly, the output of detector segment $3940_2$ at TIME ONE provides information that may be used, in combination with the output of a high energy detector at the same time, for determining an atomic number of object $4010_2$.

FIG. 40B illustrates a position of the gantry at a TIME TWO. At this time, the gantry is positioned such that array from source 3920 to low energy detector segment $3940_1$ passes through object $4010_3$ without being substantially impacted by other objects in the item under inspection. Accordingly, the outputs of detectors captured at TIME TWO may provide a useful indication of the atomic number of object $4010_3$.

Similarly, FIG. 40C shows a gantry configuration at a TIME THREE. With this configuration, a ray from source 3920 to low energy detector segment $3940_2$ passes through object $4010_1$ without being substantially impacted by other objects in the item under inspection. Accordingly, outputs of the detectors recorded at TIME THREE provide a useful indication of the atomic number of object $4010_1$.

The above described embodiments provide examples of an approach for obtaining atomic number information for multiple objects within an item under inspection using data collected with a limited number of detectors. Specifically, a relatively small number of low energy detectors is included in the system, yet dual energy measurements are possible. The described approach may be applied in other suitable systems in which origin of x-rays may be varied.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. In particular, the various aspects of the invention are not limited for use with any particular type of X-ray scanning device. The aspects of the invention may be used alone or in any combination and are not limited to the combinations illustrated in the embodiments of the foregoing.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

What is claimed is:

1. An inspection system, comprising:
   an inspection area;
   at least one x-ray source adapted to emit x-ray radiation into the inspection area at least a first energy and a second energy;
   a first plurality of detectors that are more sensitive to x-ray radiation at the first energy level than the second energy level, the first plurality of detectors being positioned to receive x-ray radiation from the at least one x-ray source after passing through the inspection area; and
   to a second plurality of detectors that are more sensitive to x-ray radiation at the second energy level than the first energy level, the second plurality of detectors being positioned to receive x-ray radiation from the at least one x-ray source after passing through the inspection area, wherein the second plurality detectors consists of fewer detectors than the first plurality of detectors.

2. The inspection system of claim 1, wherein:
   the inspection system is a computed tomography system; and
   the inspection system further comprises at least one processor adapted to construct a single-energy image of a slice through an item within the inspection area from outputs of the first plurality of detectors when irradiated by the at least one x-ray source.

3. The inspection system of claim 2, wherein the at least one x-ray source, the first plurality of detectors and the second plurality of detectors are mounted on a rotatable gantry.

4. The inspection system of claim 3, wherein:
   the gantry has an opening therethrough;
   the at least one x-ray source comprises an x-ray source mounted on the rotatable gantry on a first side of the opening;
   the first plurality of detectors are arrayed in an arc along a second side of the opening, the second side being opposite the first side; and
   the second plurality of detectors are positioned at discrete locations along the arc.

5. The inspection system of claim 2, wherein:
   the at least one x-ray source comprises a U-shaped target, an electron gun adapted to emit an electron beam and a steering mechanism adapted to steer the electron beam across the target; and
   the first plurality of detectors comprise a U-shaped array of detectors adjacent the inspection area, the U-shaped array comprising detectors each of which is diametric a portion of the target.

6. The inspection system of claim 5, wherein:
   detectors of the second plurality of detectors are positioned a discrete locations along the U-shaped array of the first plurality of detectors.

7. The inspection system of claim 2, wherein the at least one processor is further adapted to:
   based on an object identified in the image of the slice, determine a position of a source of the at least one sources;
   with the source of the at least one source in the determined position, read a value from a detector of the second plurality of detectors; and
   compute, based at least in part on the value read from the detector of the second plurality of detectors and a value read from at least one of the first plurality of detectors, an atomic number of the object.

8. The inspection system of claim 2, wherein:
   the inspection system further comprises a conveyor passing through the inspection area, the conveyor adapted to move along an axis; and
   the slice is perpendicular to the axis.

9. The inspection system of claim 1, wherein the second energy is less than the first energy and each of the second plurality of detectors overlaps a detector of the first plurality of detectors.

10. The inspection system of claim 1, wherein the second plurality detectors occupy a second area that is less than a first area of the first plurality of detectors.

11. The inspection system of claim 10, wherein the second area is less than 1 percent of the first area.

12. A method of operating an inspection system, the method comprising:
   using at least one source and a first plurality of detectors, measuring attenuation of x-rays at a first energy by an object in an inspection area;
   computing an image of a slice through the object based on the measured attenuation at a first energy;
   analyzing the image to determine whether an object of interest is present;
   when an object of interest is present, selecting a source position and a detector of a second plurality of detectors such that a path between the selected source position and selected detector passes through the object of interest;
   determining attenuation of x-rays at a second energy by the object in the inspection area along the path; and computing an atomic number of the object based on the determined attenuation at the second energy and a portion of the measured attenuation at the first energy level.

13. The method of claim 12, wherein:
the at least one source comprises a source mounted on a gantry; and
determining attenuation of x-rays at a second energy comprises measuring attenuation of x-rays at the second energy while rotating the gantry.

14. The method of claim 12, wherein:
determining attenuation of x-rays at the second energy by the object in the inspection area along the path comprises steering an electron beam to a location on a target corresponding to the selected source position.

15. The method of claim 12, wherein:
the first energy is 150 keV or above and the second energy is 120 keV or below.

16. The method of claim 12, wherein selecting a source position and a detector of the second plurality of detectors comprises selecting the path based on positioning of the object of interest relative to other objects within the item under inspection.

17. The method of claim 16, wherein:
the first plurality of detectors are disposed in an array of a first length and detectors of the second plurality of detectors are disposed at discrete locations along the array.

18. The method of claim 12, further comprising making a threat assessment of the item based at least in part on the computed atomic number.

19. The method of claim 12, wherein:
measuring the attenuation of x-rays at the first energy comprises performing a scan of an electron beam over a target to generate the x-rays from each of a plurality of locations on the target at each of a plurality of respective times;
determining attenuation of x-rays at the second energy level comprises selecting an output of the selected detector for a time during the scan when the electron beam strikes the target in a location corresponding to the selected position.

20. A method of operating an inspection system, the method comprising:
during a first phase of a scan cycle:
applying a first voltage to an x-ray source;
steering an electron beam across a target within the x-ray source by applying first control values to control elements within the x-ray source, the first control values being obtained from a first set of stored control values;
during a second phase of the scan cycle:
applying a second voltage to the x-ray source;
steering an electron beam across the target by applying second control values to the control elements within the x-ray source, the second control values being obtained from a second set of stored control values.

21. The method of claim 20, wherein the control elements are coils that steer and shape the electron beam.

22. The method of claim 20, wherein applying a first voltage to the x-ray source comprises applying a voltage of 150 keV or above between a cathode and a target of the x-ray source.

23. The method of claim 20, wherein applying the first control values comprises applying the first control values at periodic intervals.

24. The method of claim 20, wherein:
the x-ray source is a first x-ray source;
the inspection system comprises a second x-ray source;
the method further comprises:
during a third phase of the scan cycle:
applying the first voltage to the second x-ray source;
steering an electron beam across a target within the second x-ray source by applying third control values to control elements within the second x-ray source, the third control values being obtained from a third set of stored control values;
during a fourth phase of the scan cycle:
applying the second voltage to the second x-ray source;
steering an electron beam across the target within the second x-ray source by applying fourth control values to control elements within the second x-ray source, the fourth control values being obtained from a fourth set of stored control values.

25. A system comprising:
an electron beam generator;
a target;
a voltage source coupled to the electron beam generator and the target, the voltage source adapted to output a first voltage and a second voltage;
beam control components adapted to control characteristics of the electron beam as it strikes the target;
computer storage medium adapted to store a first sequence of control values and a second sequence of control values;
a timer adapted to provide an output; and
a selector, coupled to the output of the timer and to the computer storage medium, that, in response to the output of the timer, selects a control value from the first sequence of control values and applies the selected control value to the beam control components to control the beam when the voltage source outputs the first voltage and selects a control value from the second sequence of control values and applies the selected control value to the beam control components to control the beam when the voltage source outputs the second voltage.

26. The system of claim 25, wherein the beam control components comprise a beam shaping component and a beam steering component.

27. The system of claim 26, wherein the first voltage is 150 keV or above and the second voltage is 120 keV or below.

28. The system of claim 27, wherein the target comprises a plurality of L-shaped segments.

29. The system of claim 27, further comprising a first plurality of first detectors and a second plurality of second detectors, the first detectors being preferentially sensitive to radiation emitted from the target at the first voltage and the second detectors being preferentially sensitive to radiation emitted from the target at the second voltage, the first detectors being disposed in a linear array diametric the target and the second detectors being disposed at discrete locations along the linear array.

* * * * *